United States Patent
Wucherer-Plietker et al.

(10) Patent No.: US 8,420,820 B2
(45) Date of Patent: *Apr. 16, 2013

(54) PYRROLOPYRIDINYLPYRIMIDIN-2-YLAMINE DERIVATIVES

(75) Inventors: Margarita Wucherer-Plietker, Messel (DE); David Bruge, Frankfurt am Main (DE); Dirk Finsinger, Darmstadt (DE); Ulrich Graedler, Weinheim (DE); Dieter Dorsch, Ober-Ramstadt (DE); Christina Esdar, Mainz (DE)

(73) Assignee: Merck Patent GmbH, Darmstadt (DE)

( * ) Notice: Subject to any disclaimer, the term of this patent is extended or adjusted under 35 U.S.C. 154(b) by 111 days.

This patent is subject to a terminal disclaimer.

(21) Appl. No.: 13/002,168

(22) PCT Filed: Jun. 4, 2009

(86) PCT No.: PCT/EP2009/004013
§ 371 (c)(1),
(2), (4) Date: Dec. 30, 2010

(87) PCT Pub. No.: WO2010/000364
PCT Pub. Date: Jan. 7, 2010

(65) Prior Publication Data
US 2011/0218198 A1 Sep. 8, 2011

(30) Foreign Application Priority Data
Jul. 3, 2008 (DE) .......................... 10 2008 031 517

(51) Int. Cl.
*C07D 471/02* (2006.01)
*C07D 413/00* (2006.01)

(52) U.S. Cl.
USPC ............................................ 546/113; 544/122

(58) Field of Classification Search .................. 546/113; 544/122
See application file for complete search history.

(56) References Cited

FOREIGN PATENT DOCUMENTS

| WO | 2005095400 A1 | 10/2005 |
|---|---|---|
| WO | WO 2005095400 | * 10/2005 |
| WO | 2006124863 A2 | 11/2006 |
| WO | 2007107221 A1 | 9/2007 |
| WO | 2008155000 A1 | 12/2008 |

OTHER PUBLICATIONS

Fresneda et al., Tetrahedron 57 (2001) 2355-2363.*
World IP Organization. "International Search Report." PCT/EP2009/004013, Applicant: Merck Patent GMBH, Mailed: Aug. 11, 2009.
Bettayeb, Karima et al. "Meriolins, a New Class of Cell Death-Inducing Kinase Inhibitors with Enhanced Selectivity for Cyclin-Dependent Kinases." (Cancer Res), Sep. 1, 2007, pp. 8325-8334, vol. 67, No. 17.

* cited by examiner

*Primary Examiner* — Nizal Chandrakumar
(74) *Attorney, Agent, or Firm* — Millen, White, Zelano & Branigan, P.C.

(57) ABSTRACT

Compounds of the formula I in which X, $R^1$, $R^2$, $R^3$, $R^4$ and $R^6$ have the meanings indicated in claim 1, are inhibitors of cell proliferation/cell vitality and can be employed for the treatment of tumours.

18 Claims, No Drawings

SEQUENCE LISTING

```
<160> NUMBER OF SEQ ID NOS: 3

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val Val Val Pro Pro
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 2

His His His His His His
1               5

<210> SEQ ID NO 3
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (1)..(2)
<223> OTHER INFORMATION: Beta-Ala

<400> SEQUENCE: 3

Ala Ala Lys Thr Phe Cys Gly Thr Pro Glu Tyr Leu Ala Pro Glu Val
1               5                   10                  15

Arg Arg Glu Pro Arg Ile Leu Ser Glu Glu Glu Gln Glu Met Phe Arg
            20                  25                  30

Asp Phe Asp Tyr Ile Ala Asp Trp Cys
            35                  40
```

PYRROLOPYRIDINYLPYRIMIDIN-2-YLAMINE DERIVATIVES

SEQUENCE LISTING

The instant application contains a Sequence Listing which has been submitted in ASCII format via EFS-Web and is hereby incorporated by reference in its entirety. Said ASCII copy, created on Apr. 18, 2011, is named MERCK380.txt and is 1,406 bytes in size.

The invention relates to compounds of the formula I

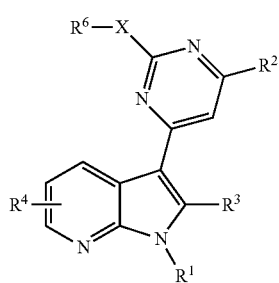

in which
$R^1$ denotes H or A,
$R^2$ denotes A, Hal, CN, $(CH_2)_n CONH(CH_2)_p Ar$, —C(OH)$R^5$—Ar, —$[C(R^5)_2]_n$—Ar, —$[C(R^5)_2]_n$-Het, —$[C(R^5)_2]_n$-cycloalkyl, —$NR^5A$, —$NR^5Ar$, $NR^5Het$, —$[C(R^5)_2]_m N(R^5)_2$, 1-hydroxycyclopentan-1-yl or 1-hydroxycyclohexan-1-yl,
$R^3$ denotes H, $R^5$, —$[C(R^5)_2]_n$—Ar, —$[C(R^5)_2]_n$-Het, —$[C(R^5)_2]_n$-cycloalkyl,
$R^4$ denotes H, Het-, Ar—, —$R^5$, —$OR^5$, —$[C(R^6)_2]_n C(O)N(R^6)_2$, CO-Het or $O(CH_2)_p Het^1$,
$R^5$ denotes H, A or cycloalkyl,
$R^6$ denotes H or A',
A' denotes unbranched or branched alkyl having 1-10 C atoms, in which 1-7 H atoms may be replaced by F,
cycloalkyl denotes cyclic alkyl having 3-7 C atoms, which may additionally be substituted by alkyl having 1-6 C atoms,
A denotes unbranched or branched alkyl having 1-10 C atoms, in which one or two CH and/or $CH_2$ groups may be replaced by N, O, S atoms and/or by —CH=CH— groups and/or in addition 1-7 H atoms may be replaced by F,
X denotes NH, O, S or $SO_2$,
Ar denotes phenyl which is unsubstituted or mono-, di- or tri-substituted by Hal, A, $OR^5$, $N(R^5)_2$, $NO_2$, CN, $COOR^5$, $CON(R^5)_2$, $NR^5COA$, $NR^5SO_2A$, $COR^5$, $SO_2N(R^5)_2$ and/or $S(O)_p A$,
Het denotes a mono- or bicyclic saturated, unsaturated or aromatic heterocycle having 1 to 4 N, and/or O and/or S atoms which is unsubstituted or mono- or disubstituted by Hal, A, $OR^5$, $(CH_2)_p N(R^5)_2$, $NO_2$, CN, $(CH_2)_p COOR^5$, $(CH_2)_p CON(R^5)_2$, $NR^5COA$, $(CH_2)_p Het^1$, $(CH_2)_p CO-Het^1$, $NR^5SO_2A$, $COR^5$, $SO_2NR^5$ and/or $S(O)_p A$,
$Het^1$ denotes a saturated heterocycle having 1 to 4 N, O, and or S atoms which is unsubstituted or mono- or disubstituted by A, $S(O)_p A$ and/or COA,
Hal denotes F, Cl, Br or I,
m denotes 1, 2, 3 or 4,
n denotes 0, 1, 2, 3 or 4,
p denotes 0, 1 or 2,
and pharmaceutically usable salts, tautomers and stereoisomers thereof, including mixtures thereof in all ratios.

In addition, the application relates to a preferred embodiment of the compounds of the formula I

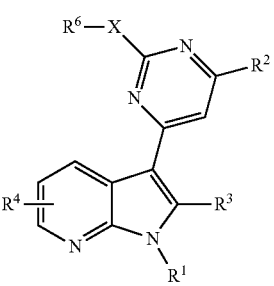

in which
$R^1$ denotes H or A,
$R^2$ denotes Hal, CN, $(CH_2)_n CONH(CH_2)_p Ar$, —C(OH)$R^5$—Ar, —$NR^5A$, —$NR^5Ar$, $NR^5Het$, —$[C(R^5)_2]_m N(R^5)_2$, 1-hydroxycyclopentan-1-yl or 1-hydroxycyclohexan-1-yl,
$R^3$ denotes $R^5$, or A,
$R^4$ denotes Het-, Ar—, —$R^5$, —$OR^5$, —$[C(R^6)_2]_n C(O)N(R^6)_2$, CO-Het or $O(CH_2)_p Het^1$,
$R^5$ denotes A or cycloalkyl,
$R^6$ denotes H or A',
A' denotes unbranched or branched alkyl having 1-10 C atoms, in which 1-7 H atoms may be replaced by F,
cycloalkyl denotes cyclic alkyl having 3-7 C atoms, which may additionally be substituted by alkyl having 1-6 C atoms,
A denotes unbranched or branched alkyl having 1-10 C atoms, in which one or two CH and/or $CH_2$ groups may be replaced by N, O, S atoms and/or by —CH=CH— groups and/or in addition 1-7 H atoms may be replaced by F,
X denotes NH, O, S or $SO_2$,
Ar denotes phenyl which is unsubstituted or mono-, di- or tri-substituted by Hal, A, $OR^5$, $N(R^5)_2$, $NO_2$, CN, $COOR^5$, $CON(R^5)_2$, $NR^5COA$, $NR^5SO_2A$, $COR^5$, $SO_2N(R^5)_2$ and/or $S(O)_p A$,
Het denotes a mono- or bicyclic saturated, unsaturated or aromatic heterocycle having 1 to 4 N, and/or O and/or S atoms which is unsubstituted or mono- or disubstituted by Hal, A, $OR^5$, $(CH_2)_p N(R^5)_2$, $NO_2$, CN, $(CH_2)_p COOR^5$, $(CH_2)_p CON(R^5)_2$, $NR^5COA$, $(CH_2)_p Het^1$, $(CH_2)_p CO-Het^1$, $NR^5SO_2A$, $COR^5$, $SO_2NR^5$ and/or $S(O)_p A$,
$Het^1$ denotes a saturated heterocycle having 1 to 4 N, O, and or S atoms which is unsubstituted or mono- or disubstituted by A, $S(O)_p A$ and/or COA,
Hal denotes F, Cl, Br or I,
m denotes 1, 2, 3 or 4,
n denotes 0, 1, 2, 3 or 4,
p denotes 0, 1 or 2,
and pharmaceutically usable salts, tautomers and stereoisomers thereof, including mixtures thereof in all ratios.

The compounds of the formula I according to the invention also include pharmaceutically usable derivatives and solvates thereof.

The invention was based on the object of finding novel compounds having valuable properties, in particular those which can be used for the preparation of medicaments.

It has been found that the compounds of the formula I and salts and/or solvates thereof have very valuable pharmacological properties while being well tolerated.

In particular, they exhibit a cell proliferation/cell vitality-inhibiting action as antagonists or agonists. The compounds according to the invention can therefore be used for the combating and/or treatment of tumours, tumour growth and/or tumour metastases.

The antiproliferative action can be tested in a proliferation assay/vitality assay.

Other 4-(pyrrolopyridinyl)pyrimidinyl-2-amine derivatives are described, for example, by P. M. Fresneda et al. in Tetrahedron 57 (2001) 2355-2363. Other 4-(pyrrolopyridinyl)pyrimidinyl-2-amine derivatives are also described by A. Karpov in his dissertation, University of Heidelberg, April 2005.

Other aminopyridine derivatives which carry a 2,2,6,6-tetramethylpiperidin-4-yl radical are described in WO 2004/089913 for the treatment of inflammatory and autoimmune diseases.

Accordingly, the compounds according to the invention or a pharmaceutically acceptable salt thereof are administered for the treatment of cancer, including solid carcinomas, such as, for example, carcinomas (for example of the lungs, pancreas, thyroid, bladder or colon), myeloid diseases (for example myeloid leukaemia) or adenomas (for example villous colon adenoma).

The tumours furthermore include monocytic leukaemia, brain, urogenital, lymphatic system, stomach, laryngeal and lung carcinoma, including lung adenocarcinoma and small-cell lung carcinoma, pancreatic and/or breast carcinoma.

The compounds are furthermore suitable for the treatment of immune deficiency induced by HIV-1 (Human Immunodeficiency Virus Type 1).

Cancer-like hyperproliferative diseases are to be regarded as brain cancer, lung cancer, squamous epithelial cancer, bladder cancer, stomach cancer, pancreatic cancer, liver cancer, renal cancer, colorectal cancer, breast cancer, head cancer, neck cancer, oesophageal cancer, gynaecological cancer, thyroid cancer, lymphomas, chronic leukaemia and acute leukaemia. In particular, cancer-like cell growth is a disease which represents a target of the present invention. The present invention therefore relates to compounds according to the invention as medicaments and/or medicament active ingredients in the treatment and/or prophylaxis of the said diseases and to the use of compounds according to the invention for the preparation of a pharmaceutical for the treatment and/or prophylaxis of the said diseases and to a process for the treatment of the said diseases comprising the administration of one or more compounds according to the invention to a patient in need of such an administration.

It can be shown that the compounds according to the invention have an antiproliferative action. The compounds according to the invention are administered to a patient having a hyperproliferative disease, for example to inhibit tumour growth, to reduce inflammation associated with a lymphoproliferative disease, to inhibit transplant rejection or neurological damage due to tissue repair, etc. The present compounds are suitable for prophylactic or therapeutic purposes. As used herein, the term "treatment" is used to refer to both the prevention of diseases and the treatment of pre-existing conditions. The prevention of proliferation/vitality is achieved by administration of the compounds according to the invention prior to the development of overt disease, for example for preventing tumour growth. Alternatively, the compounds are used for the treatment of ongoing diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of a human disease.

The susceptibility of a particular cell to treatment with the compounds according to the invention can be determined by in vitro testing. Typically, a culture of the cell is incubated with a compound according to the invention at various concentrations for a period of time which is sufficient to allow the active agents to induce cell death or to inhibit cell proliferation, cell vitality or migration, usually between about one hour and one week. In vitro testing can be carried out using cultivated cells from a biopsy sample. The amount of cells remaining after the treatment are then determined.

The dose varies depending on the specific compound used, the specific 10, disease, the patient status, etc. A therapeutic dose is typically sufficient considerably to reduce the undesired cell population in the target tissue, while the viability of the patient is maintained. The treatment is generally continued until a considerable reduction has occurred, for example an at least about 50% reduction in the cell burden, and may be continued until essentially no more undesired cells are detected in the body.

There are many diseases associated with deregulation of cell proliferation and cell death (apoptosis). The conditions of interest include, but are not limited to, the following. The compounds according to the invention are suitable for the treatment of various conditions where there is proliferation and/or migration of smooth muscle cells and/or inflammatory cells into the intimal layer of a vessel, resulting in restricted blood flow through that vessel, for example in the case of neointimal occlusive lesions. Occlusive graft vascular diseases of interest include atherosclerosis, coronary vascular disease after grafting, vein graft stenosis, perianastomatic prosthetic restenosis, restenosis after angioplasty or stent placement, and the like.

The compounds of the formula I, also act as regulators, modulators or inhibitors of protein kinases, in particular of the serine/threonine kinase type, which include, inter alia, phosphoinositide-dependent kinase 1 (PDK 1). The compounds according to the invention exhibit a certain action in the inhibition of serine/threonine kinase PDK1.

PDK1 phosphorylates and activates a sub-group of the AGC protein kinase family, comprising PKB, SGK, S6K and PKC isoforms. These kinases are involved in the PI3K signal transduction pathway and control basic cellular functions, such as survival, growth and differentiation. PDK1 is thus an important regulator of diverse metabolic, proliferative and life-sustaining effects.

Diseases caused by protein kinases are characterised by anomalous activity or hyperactivity of such protein kinases. Anomalous activity relates either to: (1) the expression in cells which do not usually express these protein kinases; (2) increased kinase expression which results in undesired cell proliferation, such as cancer; (3) increased kinase activity which results in undesired cell proliferation, such as cancer, and/or in hyperactivity of the corresponding protein kinases. Hyperactivity relates either to amplification of the gene which encodes a certain protein kinase or the generation of an activity level which can be correlated with a cell proliferation disease (i.e. the severity of one or more symptoms of the cell proliferation disease increases with increasing kinase level) the bioavailability of a protein kinase can also be influenced by the presence or absence of a set of binding proteins of this kinase.

The most important types of cancer that can be treated using a compound according to the invention include colorectal cancer, small-cell lung cancer, non-small-cell lung cancer, multiple myeloma as well as renal cell carcinoma and endometrium carcinoma, particularly also types of cancer in which PTEN is mutated, inter alia breast cancer, prostate cancer and glioblastoma.

In addition, the compounds according to the invention can be used to achieve additive or synergistic effects in certain existing cancer chemotherapies and radiotherapies and/or to restore the efficacy of certain existing cancer chemotherapies and radiotherapies.

The invention also relates to the optically active forms (stereoisomers), salts, the enantiomers, the racemates, the diastereomers and the hydrates and solvates of these compounds. The term solvates of the compounds is taken to mean adductions of inert solvent molecules onto the compounds which form owing to their mutual attractive force. Solvates are, for example, mono- or dihydrates or alkoxides.

The term pharmaceutically usable derivatives is taken to mean, for example, the salts of the compounds according to the invention and also so-called prodrug compounds.

The term prodrug derivatives is taken to mean compounds of the formula I which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:
improved treatment, healing, prevention or elimination of a disease, syndrome, condition, complaint, disorder or side effects or also the reduction in the advance of a disease, condition or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The invention relates to the compounds of the formula I and salts thereof and to a process for the preparation of compounds of the formula I according to Claims 1-12 and pharmaceutically usable salts, tautomers and stereoisomers thereof, characterised in that a) a compound of the formula II

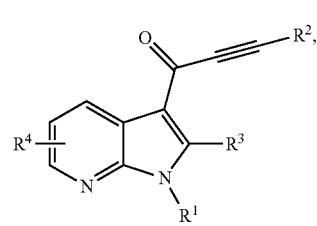

in which $R^1$ denotes an indole-protecting group,
$R^2$, $R^3$ and $R^4$ have the meanings indicated in Claim 1,
is reacted with guanidine,
and the indole-protecting group is simultaneously or subsequently cleaved off,
or
b) a radical $R^2$ in a compound of the formula I is converted into another $R^2$
by
i) cleaving off an amino-protecting group,
ii) cleaving an imide to give an amine,
iii) carrying out an alkylation,
and/or a base or acid of the formula I is converted into one of its salts.

Above and below, the radicals $R^1$, $R^2$, $R^3$. $R^4$ and $R^6$ have the meanings indicated for the formula I, unless expressly indicated otherwise.

A denotes alkyl, is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

One or two CH and/or $CH_2$ groups in A may also be replaced by N, O or S atoms and/or by —CH=CH— groups. A thus also denotes, for example, 2-methoxyethyl.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-trifluoromethylphenyl, o-, m- or p-fluorophenyl, o-, m- or p-bromophenyl, o-, m- or p-chlorophenyl, o-, m- or p-hydroxyphenyl, o-, m- or p-methoxyphenyl, o-, m- or p-methylsulfonylphenyl, o-, m- or p-nitrophenyl, o-, m- or p-aminophenyl, o-, m- or p-methylaminophenyl, o-, m- or p-dimethylaminophenyl, o-, m- or p-aminosulfonylphenyl, o-, m- or p-methylaminosulfonylphenyl, o-, m- or p-aminocarbonylphenyl, o-, m- or p-carboxyphenyl, o-, m- or p-methoxycarbonylphenyl, o-, m- or p-ethoxycarbonylphenyl, o-, m- or p-acetylphenyl, o-, m- or p-formylphenyl, o-, m- or p-cyanophenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3,4-, 2,3,5-, 2,3,6-, 2,4,6- or 3,4,5-trichlorophenyl, p-iodophenyl, 4-fluoro-3-chlorophenyl, 2-fluoro-4-bromophenyl, 2,5-difluoro-4-bromophenyl or 2,5-dimethyl-4-chlorophenyl.

Ar particularly preferably denotes phenyl which is unsubstituted or mono-, di- or trisubstituted by $N(R^5)_2$, Hal, and/or $CON(R^5)_2$.

Irrespective of further substitutions, Het denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 2-, 3-, 4-, 5-, 6- or 7-indazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals may also be partially or fully hydrogenated.

Unsubstituted Het can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy) phenyl, 2,3-dihydrobenzofuran-5- or 6-yl, 2,3-dihydro-(2-oxomethylenedioxy)phenyl or also 3,4-dihydro-2H-1,5-benzodioxepin-6- or -7-yl, furthermore preferably 2,3-dihydrobenzofuranyl or 2,3-dihydro-2-oxofuranyl.

Het furthermore preferably denotes a mono- or bicyclic saturated, unsaturated or aromatic heterocycle having 1 to 3 N and/or O atoms which is unsubstituted or mono- or disubstituted by $OR^5$, $(CH_2)_pN(R^5)_2$, $NO_2$, CN, $(CH_2)_pCOOR^5$, $(CH_2)_pCON(R^5)_2$, $NR^5COA$, $(CH_2)_pHet^1$, $(CH_2)_pCOHet^1$, $NR^5SO_2A$, $COR^5$, $SO_2NR^5$ or $S(O)_pA$, OH, A, Hal, and/or =O (carbonyl oxygen);

furthermore particularly preferably dihydropyrrolyl, pyrrolidinyl, tetrahydroimidazolyl, dihydropyrazolyl, tetrahydropyrazolyl, dihydropyridyl, tetrahydropyridyl, piperidinyl, morpholinyl, hexahydropyridazinyl, hexahydro-pyrimidinyl, piperazinyl, 1,2,3,4-tetrahydroquinolyl, 1,2,3,4-tetrahydroisoquinolyl, 3,4-dihydrobenzo-1,4-oxazinyl, 2,3-dihydroisoindolyl, 2,3-dihydroindolyl, oxazolidinyl, isoxazolidinyl, oxadiazolidinyl, thiazolidinyl, furyl, thienyl, pyrrolyl, imidazolyl, pyrazolyl, oxazolyl, isoxazolyl, thiazolyl, pyridyl, pyrimidinyl, triazolyl, tetrazolyl, thiadiazole, pyridazinyl, pyrazinyl, indolyl, isoindolyl, benzimidazolyl, indazolyl, quinolyl or 1,3-benzodioxolyl, each of which is unsubstituted or mono-, di or trisubstituted by A, OH, OA, Hal, $CON(R^5)_2$, $N(R^5)_2$ and/or =O.

Het very particularly preferably denotes dihydropyrrolyl, pyrrolidinyl, tetrahydroimidazolyl, dihydropyrazolyl, tetrahydropyrazolyl, dihydropyridyl, tetrahydropyridyl, piperidinyl, morpholinyl, piperazinyl, imidazolyl, pyrazolyl, oxazolyl, isoxazolyl, pyridyl, pyrimidinyl or triazolyl, hexahydropyridazinyl, hexahydropyrimidinyl, 1,2,3,4-tetrahydroquinolyl, 1,2,3,4-tetrahydroisoquinolyl, 3,4-dihydrobenzo-1,4-oxazinyl, 2,3-dihydroisoindolyl or 2,3-dihydroindolyl, pyrazolyl, pyridyl, furyl or isooxazole, each of which is unsubstituted or mono- or di or trisubstituted by A, $CON(R^5)_2$, $N(R^5)_2$ or F and/or =O.

$Het^1$ preferably denotes tetrahydrofuranyl, piperidinyl, piperazinyl, pyrrolidinyl, or morpholinyl, where the radicals may be monosubstituted by A, CO, or $S(O)_pA$.

$R^1$ preferably denotes H.

$R^2$ denotes A, Hal, CN, $(CH_2)_nCONH(CH_2)_pAr$, —C(OH) $R^5$—Ar, $—[C(R^5)_2]_n$—Ar, $—[C(R^5)_2]_n$-Het, $—[C(R^5)_2]_n$-cycloalkyl, $—NR^5A$, $—NR^5Ar$, $NR^5Het$, $—[C(R^5)_2]_mN(R^5)_2$, 1-hydroxycyclopentan-1-yl or 1-hydroxycyclohexan-1-yl.

Hal preferably denotes F, Cl or Br, but also I, particularly preferably F or Cl.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to Il, which conform to the formula I and in which the radicals not designated in greater detail have the meaning indicated for the formula I, but in which in Ia $R^1$ denotes H;

in Ib $R^2$ denotes ethyl, aminopropyl, morpholin-4-ylmethyl, piperazin-1-ylmethyl, dimethylaminomethyl, methylaminomethyl, 3-dimethylaminopropyl, 3-methylaminopropyl, 1-hydroxycyclopentan-1-yl, 1-hydroxycyclohexan-1-yl, morpholin-4-ylpropyl, 1-(morpholin-4-yl)-1-oxopropanyl, 1-[(2-dimethylaminoethyl)amino]-1-oxopropanyl, 3-aminopropanyl, 1hydroxybutyl, 1-[(3,4-difluorobenzyl)amino]-1-oxopropanyl, methylamino, 3-acetamidopropyl, 2-(dimethylaminocarbonyl)ethyl, 1-hydroxy-2-methylpropyl, 1-hydroxypropyl, 1-hydroxy-3-methylbutyl, cyclohexyl, propyl, butyl, 3-imidazolepropyl, 2-imidazolethyl, 1-(benzyloxycarbonyl)-4-hydroxypiperidin-4-yl, 1-isopropyl-4-hydroxypiperidin-4-ylm, 1-hydroxy-1-phenylmethyl, 1-[2-(4-fluorophenyl)ethyl]-4-hydroxypiperidin-4-yl, 4-hydroxypiperidin-4-yl or 1-phenyl-1-hydroxypropyl, in Ic $R^3$ denotes H;

in Id $R^4$ denotes H, 1-(tetrahydrofuran-2-ylmethyl)-1H-pyrazolyl, methyl-(2-pyrazol-1-ylethyl)amino, dimethyl-(3-pyrazol-1-ylpropyl)amino, dimethyl-(2-pyrazol-1-ylethyl)amino, 1-methyl-4-pyrazol-1-ylpiperidinyl, 4-pyrazol-1-ylpiperidinyl, 1-phenylpiperazinyl, 1-(2-pyrrolidin-1-ylethyl)-1H-pyrazolyl, 4-(2-pyrazol-1-ylethyl) morpholinyl, 1-pyrrolidin-3-ylmethyl-1H-pyrazolyl, 3-[N-(2-dimethylaminoethyl)aminocarbonyl]phenyl, 4-methylpiperazine-1-carbonyl, morpholine-4-carbonyl, N-(4-dimethylaminobutyl)aminocarbonyl, 2-dimethylaminoethoxy, piperidin-4-ylmethoxy, C-piperidin-4-ylmethylamino, CH₃NH(CH₂)₄NH—, (CH₃)₂N(CH₂)₄NH—, 2-(tetrahydrofuran-2-ylmethyl)oxazolyl, 2-(tetrahydrofuran-2-ylmethyl)-1H-imidazolyl, 1-(tetrahydrofuran-2-ylmethyl)-1H-imidazolyl, 1-benzyl-1H-1,2,3-triazolyl 5-phenyloxazolyl, 4-aminomethylphenyl, 1-(1-acetylpiperidin-4-yl)pyrazol-4-yl, 1-piperidin-4-ylpyrazol-4-yl), 1-(2-hydroxyethyl)pyrazol-4-yl), 1-(1-methylpiperidin-4-yl)pyrazol-4-yl, 2-isopropylpyrazol-4-yl, 1-(2-oxo-2-methylaminoethyl)pyrazol-4-yl, 1-[2-dimethylaminoethyl]pyrazol-4-yl, pyrazolyl, 1-methylpyrazol-4-yl, 1-(3-fluorobenzyl)pyrazol-4-yl, 1-(3,4-difluorobenzyl)pyrazol-4-y, 1-[1-(piperidin-1-yl)acetyl]pyrazol-4-yl, 1-[1-(pyrrolidin-1-yl)acetyl]-pyrazol-4-yl, 1-[3-(indol-5-ylamino)-3-oxopropan-2-yl]pyrazol-4yl or 1-(3,4-dihydro-2H-quinolin-1-yl-carbonylmethyl)pyrazol-4-yl, in Ie A denotes unbranched or branched alkyl having 1-8 C atoms, in which one or two CH and/or CH₂ groups may be replaced by N, or O atoms and/or by —CH=CH— groups and/or in addition 1-7 H atoms may be replaced by F in If Ar denotes phenyl which is unsubstituted or mono- di- or trisubstituted by $N(R^5)_2$, Hal or $CON(R^5)_2$;

in Ig Het denotes a mono- or bicyclic saturated, unsaturated or aromatic heterocycle having 1 to 3 N and/or O atoms which is unsubstituted or mono- or di- or trisubstituted by $OR^5$, $(CH_2)_pN(R^5)_2$, $NO_2$, CN, $(CH_2)_pCOOR^5$, $(CH_2)_pCON(R^5)_2$, $NR^5COA$, $(CH_2)_pHet^1$, $(CH_2)_pCOHet^1$, $NR^5SO_2A$, $COR^5$, $SO_2NR^5$ or $S(O)_pA$, A, $(CH_2)_pHet^1$, OH, OA, Hal, and/or =O (carbonyl oxygen);

in Ih Het denotes dihydropyrrolyl, pyrrolidinyl, tetrahydroimidazolyl, dihydropyrazolyl, tetrahydropyrazolyl, morpholinyl, piperazinyl, imidazolyl, pyrazolyl, oxazolyl, isoxazolyl, pyridyl, pyrimidinyl or triazolyl, dihydropyridyl, tetrahydropyridyl, piperidinyl, hexahydropyridazinyl, hexahydropyrimidinyl, piperazinyl, 1,2,3,4-tetrahydroquinolyl, 1,2,3,4-tetrahydroisoquinolyl, 3,4-dihydrobenzo-1,4-oxazinyl, 2,3-dihydroisoindolyl, 2,3-dihydroindolyl, pyrazolyl, pyridyl, furyl or isooxazyl, each of which is unsubstituted or mono- or di- or trisubstituted by A, $(CH_2)_pHet^1$, $(CH_2)_pN(R^5)_2$, $NO_2$, CN, $(CH_2)_pCOOR^5$, $(CH_2)_pCON(R^5)_2$, $NR^5COA$, $(CH_2)_pCOHet^1$, F and/or =O, in Ii Het denotes morpholinyl, piperazinyl, imidazolyl, pyrazolyl, oxazolyl, isoxazolyl, pyridyl, pyrimidinyl or triazolyl, in Ij Het denotes dihydropyrrolyl, pyrrolidinyl, tetrahydroimidazolyl, dihydropyrazolyl, tetrahydropyrazolyl, dihydropyridyl, tetrahydropyridyl, piperidinyl, morpholinyl, hexahydropyridazinyl, hexahydropyrimidinyl, piperazinyl, 1,2,3,4-tetrahydroquinolyl, 1,2,3,4-tetrahydroisoquinolyl, 3,4-dihydrobenzo-1,4-oxazinyl, 2,3-dihydroisoindolyl, 2,3-dihydroindolyl, oxazolidinyl, isoxazolidinyl, oxadiazolidinyl, thiazolidinyl, furyl, thienyl, pyrrolyl, imidazolyl, pyrazolyl, oxazolyl, isoxazolyl, thiazolyl, pyridyl, pyrimidinyl, triazolyl, tetrazolyl, thiadiazole, pyridazinyl, pyrazinyl, indolyl, isoindolyl, benzimidazolyl, indazolyl, quinolyl or 1,3-benzodioxolyl, each of which is unsubstituted or mono- or di-, or trisubstituted by A, Ar, $(CH_2)_pHet^1$, OH, OA, Hal, $(CH_2)_pN(R^5)_2$, $NO_2$, CN, $(CH_2)_pCOOR^5$, $(CH_2)_pCON(R^5)_2$, $NR^5COA$, $(CH_2)_pCOHet^1$, F and/or =O, in Ik $Het^1$ denotes tetrahydrofuranyl, piperidinyl, piperazinyl, pyrrolidinyl, or morpholinyl, each of which is unsubstituted or monosubstituted by A, COA or $S(O)_pA$ and in Il $R^1$ denotes H, $R^2$ denotes ethyl, aminopropyl, morpholin-4-ylmethyl, piperazin-1-ylmethyl, dimethylaminomethyl, methylaminomethyl, 3-dimethylaminopropyl, 3-methylaminopropyl, 1-hydroxycyclopentan-1-yl, 1-hydroxycyclohexan-1-y, morpholin-4-ylpropyl, 1-(morpholin-4-yl)-1-oxopropanyl, 1-[(2-dimethylaminoethyl)amino]-1-oxopropanyl, 3-aminopropanyl, 1hydroxybutyl, 1-[(3,4-difluorobenzyl)amino]-1-oxopropanyl, methylamino, 3-acetamidopropyl, 2-(dimethylaminocarbonyl)ethyl, 1-hydroxy-2-methylpropyl, 1-hydroxypropyl, 1-hydroxy-3-methylbutyl, cyclohexyl, propyl, butyl, 3-imidazolepropyl, 2-imidazolethyl, 1-(benzyloxycarbonyl)-4-hydroxypiperidin-4-yl, 1-isopropyl-4-hydroxypiperidin-4-ylm, 1-hydroxy-1-phenylmethyl, 1-[2-(4-fluorophenyl)ethyl]-4-hydroxypiperidin-4-yl, 4-hydroxypiperidin-4-yl or 1-phenyl-1-hydroxypropyl, $R^3$ denotes H, $R^4$ denotes H, 1-(tetrahydrofuran-2-ylmethyl)-1H-pyrazolyl, methyl-(2-pyrazol-1-ylethyl)amino, dimethyl (3-pyrazol-1-ylpropyl)amino, dimethyl-(2-pyrazol-1-ylethyl)amino, 1-methyl-4-pyrazol-1-ylpiperidinyl, 4-pyrazol-1-ylpiperidinyl, 1-phenylpiperazinyl, 1-(2-pyrrolidin-1-ylethyl)-1H-pyrazolyl, 4-(2-pyrazol-1-ylethyl)morpholinyl, 1-pyrrolidin-3-ylmethyl-1H-pyrazolyl, 3-[N-(2-dimethylaminoethyl)aminocarbonyl]phenyl, 4-methylpiperazine-1-carbonyl, morpholine-4-carbonyl, N-(4-dimethylaminobutyl)aminocarbonyl, 2-dimethylaminoethoxy, piperidin-4-ylmethoxy, C-piperidin-4-ylmethylamino, CH₃NH(CH₂)₄NH—, (CH₃)₂N(CH₂)₄NH—, 2-(tetrahydrofuran-2-ylmethyl)oxazolyl, 2-(tetrahydrofuran-2-ylmethyl)-1H-imidazolyl, 1-(tetrahydrofuran-2-ylmethyl)-1H-imidazolyl, 1-benzyl-1H-1,2,3-triazolyl 5-phenyloxazolyl, 4-aminomethylphenyl, 1-(1-acetylpiperidin-4-yl)pyrazol-4-yl, 1-piperidin-4-ylpyrazol-4-yl), 1-(2-hydroxyethyl)pyrazol-4-yl), 1-(1-methylpiperidin-4-yl)pyrazol-4-yl, 2-isopropylpyrazol-4-yl, 1-(2-oxo-2-methylaminoethyl)pyrazol-4-yl, 1-[2-dimethylaminoethyl]pyrazol-4-yl, pyrazolyl, 1-methylpyrazol-4-yl, 1-(3-fluorobenzyl)pyrazol-4-yl, 1-(3,4-difluorobenzyl)pyrazol-4-y, 1-[1-(piperidin-1-yl)acetyl]pyrazol-4-yl, 1-[1-(pyrrolidin-1-yl)acetyl]pyrazol-4-yl, 1-[3-(indol-5-ylamino)-3-oxopropan-2-yl]pyrazol-4-yl or 1-(3,4-dihydro-2H-quinolin-1-ylcarbonylmethyl)pyrazol-4-yl, A denotes unbranched or branched alkyl having 1-6 C atoms, in which one or two CH₂ groups may be replaced by oxygen and/or in addition 1-7 H atoms may be replaced by F, Ar denotes phenyl which is unsubstituted or mono- di- or trisubstituted by $N(R^5)_2$, Hal or $CON(R^5)_2$ Het denotes dihydropyrrolyl, pyrrolidinyl, tetrahydroimidazolyl, dihydropyrazolyl, tetrahydropyrazolyl, morpholinyl, piperazinyl, imidazolyl, pyrazolyl, oxazolyl, isoxazolyl, pyridyl, pyrimidinyl or triazolyl, dihydropyridyl, tetrahydropyridyl, piperidinyl, hexahydropyridazinyl, hexahydropyrimidinyl, piperazinyl, 1,2,3,4-tetrahydroquinolyl, 1,2,3,4-tetrahydroisoquinolyl, 3,4-dihydrobenzo-1,4-oxazinyl, 2,3-dihydroisoindolyl, 2,3-dihydroindolyl, pyrazolyl, pyridyl, furyl or isooxazole, each of which is unsubstituted or mono-, di- or trisubstituted by A, $(CH_2)_pHet^1$, $(CH_2)_pN(R^5)_2$, $NO_2$, CN, $(CH_2)_pCOOR^5$, $(CH_2)_pCON(R^5)_2$, $NR^5COA$, $(CH_2)_pCOHet^1$, F and/or =O, n denotes 0, 1, 2, 3 or 4 and

Het$^1$ denotes tetrahydrofuranyl, piperidinyl, piperazinyl, pyrrolidinyl, or morpholinyl, each of which is unsubstituted or monosubstituted by A, COA or S(O)$_p$A and pharmaceutically usable salts, tautomers and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

Compounds of the formula I can preferably be obtained by reacting compounds of the formula II and with a guanidine salt, such as, for example, guanidinium carbonate.

The compounds of the formula II are generally known. If they are novel, however, they can be prepared by methods known per se.

The reaction is carried out in an inert solvent and is generally carried out in the presence of an acid-binding agent, preferably an organic base, such as DIPEA, triethylamine, dimethylaniline, pyridine or quinoline.

The addition of an alkali or alkaline-earth metal hydroxide, carbonate or bicarbonate or another salt of a weak acid of the alkali or alkaline-earth metals, preferably of potassium, sodium, calcium or caesium, may also be favourable.

Depending on the conditions used, the reaction time is between a few minutes and 14 days, the reaction temperature is between about −15° and 150°, normally between 40° and 130°, particularly preferably between 60° and 110° C.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to glycol ethers, such as ethylene glycol monomethyl ether, THF, dichloromethane and/or DMF.

Preferred indole-protecting groups are, for example, sulfonyl-protecting groups, such as tosyl or mesyl, furthermore protecting groups such as, for example, BOC.

The cleavage of an ether is carried out by methods as are known to the person skilled in the art.

A standard method of ether cleavage, for example of a methyl ether, is the use of boron tribromide.

Hydrogenolytically removable groups, for example the cleavage of a benzyl ether, can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar.

Esters can be saponified, for example, using acetic acid or using NaOH or KOH in water, water/THF or water/dioxane, at temperatures between 0 and 100°.

Alkylations on the nitrogen are carried out under standard conditions, as are known to the person skilled in the art.

The compounds of the formulae I can furthermore be obtained by liberating them from their functional derivatives by solvolysis, in particular hydrolysis, or by hydrogenolysis.

Preferred starting materials for the solvolysis or hydrogenolysis are those which contain corresponding protected amino and/or hydroxyl groups instead of one or more free amino and/or hydroxyl groups, preferably those which carry an amino-protecting group instead of an H atom bonded to an N atom, for example those which conform to the formula I, but contain an NHR' group (in which R' denotes an amino-protecting group, for example BOC or CBZ) instead of an NH$_2$ group.

Preference is furthermore given to starting materials which carry a hydroxyl-protecting group instead of the H atom of a hydroxyl group, for example those which conform to the formula I, but contain an R"O-phenyl group (in which R" denotes a hydroxyl-protecting group) instead of a hydroxyphenyl group.

It is also possible for a plurality of—identical or different—protected amino and/or hydroxyl groups to be present in the molecule of the starting material. If the protecting groups present are different from one another, they can in many cases be cleaved off selectively.

The expression "amino-protecting group" is known in general terms and relates to groups which are suitable for protecting (blocking) an amino group against chemical reactions, but are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size is furthermore not crucial; however, preference is given to those having 1-20, in particular 1-8, C atoms. The expression "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl, butyryl; aralkanoyl, such as phenylacetyl; aroyl, such as benzoyl, tolyl; aryloxyalkanoyl, such as POA; alkoxycarbonyl, such as methoxycarbonyl, ethoxycarbonyl, 2,2,2-trichloroethoxycarbonyl, BOC, 2-iodoethoxycarbonyl; aralkoxycarbonyl, such as CBZ ("carbobenzoxy"), 4-methoxybenzyloxycarbonyl, FMOC; arylsulfonyl, such as Mtr, Pbf, Pmc. Preferred amino-protecting groups are BOC and Mtr, furthermore CBZ, Fmoc, benzyl and acetyl.

The expression "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups is not crucial since they are removed again after the desired chemical reaction or reaction sequence; preference is given to groups having 1-20, in particular 1-10, C atoms. Examples of hydroxyl-protecting groups are, inter alia, tert-butoxycarbonyl, benzyl, p-nitrobenzoyl, p-toluenesulfonyl, tert-butyl and acetyl, where benzyl and tert-butyl are particularly preferred. The COOH groups in aspartic acid and glutamic acid are preferably protected in the form of their tert-butyl esters (for example Asp(OBut)).

The compounds of the formula I are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, OBut, Pbf, Pmc and Mtr groups can, for example, preferably be cleaved off using TFA in dichloromethane or using approximately 3 to 5 N HCl in dioxane at 15-30°, the FMOC group can be cleaved off using an approximately 5 to 50% solution of dimethylamine, diethylamine or piperidine in DMF at 15-30°.

Hydrogenolytically removable protecting groups (for example CBZ or benzyl) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar. Hydrogenolysis of the CBZ group succeeds well, for example, on 5 to 10% Pd/C in methanol or using ammonium formate (instead of hydrogen) on Pd/C in methanol/DMF at 20-30°.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline-earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline-earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di($C_1-C_4$) alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl($C_1-C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline-earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The invention furthermore relates to medicaments comprising at least one compound of the formula I and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, can likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, solvates and physiologically functional derivatives thereof can also be delivered using monoclonal anti-bodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986). Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound of the formula I and/or pharmaceutically usable derivatives, solvates and stereoisomers thereof, including mixtures thereof in all ratios, and at least one further medicament active ingredient.

In particular, the invention relates to the group of the following compounds and pharmaceutically usable derivatives, solvates and stereoisomers thereof, including mixtures thereof in all ratios:

4-{5-[1-(2-dimethylaminoethyl)-1H-pyrazol-4-yl]-1H-pyrrolo[2,3-b]pyridin-3-yl}-6-ethylpyrimidin-2-ylamine ("A1"),
4-ethyl-6-{5-[1-(tetrahydrofuran-2-ylmethyl)-1H-pyrazol-4-yl]-1H-pyrrolo[2,3-b]pyridin-3-yl}pyrimidin-2-ylamine ("A2"),
4-ethyl-6-{5-[1-(2-methylaminoethyl)-1H-pyrazol-4-yl]-1H-pyrrolo-[2,3-b]pyridin-3-yl}pyrimidin-2-yl, ("A3"),
4-{5-[1-(3-dimethylaminopropyl)-1H-pyrazol-4-yl]-1H-pyrrolo[2,3-b]-pyridin-3-yl}-6-ethylpyrimidin-2-ylamine ("A4"),
4-ethyl-6-{5-[1-(1-methylpiperidin-4-yl)-1H-pyrazol-4-yl]-1H-pyrrolo-[2,3-b]pyridin-3-yl}pyrimidin-2-ylamine ("A5"),
4-ethyl-6-[5-(1-piperidin-4-yl-1H-pyrazol-4-yl)-1H-pyrrolo[2,3-b]pyridin-3-yl]pyrimidin-2-ylamine ("A6"),
4-ethyl-6-{5-[1-(2-pyrrolidin-1-ylethyl)-1H-pyrazol-4-yl]-1H-pyrrolo-[2,3-b]pyridin-3-yl}pyrimidin-2-ylamine ("A7"),
4-ethyl-6-{5-[1-(2-morpholin-4-ylethyl)-1H-pyrazol-4-yl]-1H-pyrrolo-[2,3-b]pyridin-3-yl}pyrimidin-2-ylamine ("A8"),
4-ethyl-6-[5-(1-pyrrolidin-3-yl 1H-pyrazol-4-yl)-1H-pyrrolo[2,3-b]pyridin-3-yl]pyrimidin-2-ylamine ("A9"),
4-ethyl-6-[5-(6-piperazin-1-ylpyridin-3-yl)-1H-pyrrolo[2,3-b]pyridin-3-yl]-pyrimidin-2-ylamine ("A10"),
3-[3-(2-amino-6-ethylpyrimidin-4-yl)-1H-pyrrolo[2,3-b]pyridin-5-yl]-N-(2-dimethylaminoethyl)benzamide ("A11"),
[3-(2-amino-6-ethylpyrimidin-4-yl)-1H-pyrrolo[2,3-b]pyridin-5-yl]-(4-methylpiperazin-1-yl)methanone ("A12"),
[3-(2-amino-6-ethylpyrimidin-4-yl)-1H-pyrrolo[2,3-b]pyridin-5-yl]morpholin-4-ylmethanone ("A13"),
N-(4-dimethylaminobutyl)-3-(2-amino-6-ethylpyrimidin-4-yl)-1H-pyrrolo[2,3-b]pyridin-5-carboxamide ("A14"),
4-[5-(2-dimethylaminoethoxy)-1H-pyrrolo[2,3-b]pyridin-3-yl]-6-ethylpyrimidin-2-ylamine ("A15"),
4-ethyl-6-[5-(piperidin-4-ylmethoxy)-1H-pyrrolo[2,3-b]pyridin-3-yl]pyrimidin-2-ylamine ("A16"),
[3-(2-amino-6-ethylpyrimidin-4-yl)-1H-pyrrolo[2,3-b]pyridin-5-yl]piperidin-4-ylmethylamine ("A17"),
N-[3-(2-amino-6-ethylpyrimidin-4-yl)-1H-pyrrolo[2,3-b]pyridin-5-yl]-N'-methylbutane-1,4-diamine ("A18"),
N-[3-(2-amino-6-ethylpyrimidin-4-yl)-1H-pyrrolo[2,3-b]pyridin-5-yl]-N',N'-dimethylbutane-1,4-diamine ("A19"),
4-(3-aminopropyl)-6-{5-[1-(2-pyrrolidin-1-ylethyl)-1H-pyrazol-4-yl]-1H-pyrrolo[2,3-b]pyridin-3-yl}pyrimidin-2-ylamine ("A20"),
4-(3-aminopropyl)-6-{5-[1-(2-morpholin-4-ylethyl)-1H-pyrazol-4-yl]-1H-pyrrolo[2,3-b]pyridin-3-yl}pyrimidin-2-ylamine ("A21"),
4-morpholin-4-ylmethyl-6-{5-[1-(2-pyrrolidin-1-ylethyl)-1H-pyrazol-4-yl]-1H-pyrrolo[2,3-b]pyridin-3-yl}pyrimidin-2-ylamine ("A22"),
4-piperazin-1-ylmethyl-6-{5-[1-(2-pyrrolidin-1-ylethyl)-1H-pyrazol-4-yl]-1H-pyrrolo[2,3-b]pyridin-3-yl}pyrimidin-2-ylamine ("A23"),
4-ethyl-6-{5-[1-(tetrahydrofuran-2-ylmethyl)-1H-imidazol-4-yl]-1H-pyrrolo[2,3-b]pyridin-3-yl}pyrimidin-2-ylamine (A"24"),
4-[5-(1-benzyl-1H-1,2,3-triazol-4-yl)-1H-pyrrolo[2,3-b]pyridin-3-yl]-6-ethylpyrimidin-2-ylamine (A"25"),
4-(3-dimethylaminopropyl)-6-{5-[1-(2-pyrrolidin-1-ylethyl)-1H-pyrazol-4-yl]-1H-pyrrolo[2,3-b]pyridin-3-yl}pyrimidin-2-ylamine ("A26"),
4-ethyl-6-[5-(5-phenyloxazol-2-yl)-1H-pyrrolo[2,3-b]pyridin-3-yl]pyrimidin-2-ylamine ("A27"),
2-{4-[3-(2-amino-6-ethylpyrimidin-4-yl)-1H-pyrrolo[2,3-b]pyridin-5-yl]-pyrazol-1-yl}-1-(4-methylpiperazin-1-yl)ethanone ("A29"),
2-{4-[3-(2-amino-6-ethylpyrimidin-4-yl)-1H-pyrrolo[2,3-b]pyridin-5-yl]-pyrazol-1-yl}-N-(1-methylpiperidin-4-yl)acetamide ("A30"),
{4-[3-(2-amino-6-ethylpyrimidin-4-yl)-1H-pyrrolo[2,3-b]pyridin-5-yl]-pyrazol-1-yl}acetylic acid ("A31"),
2-{4-[3-(2-amino-6-ethylpyrimidin-4-yl)-1H-pyrrolo[2,3-b]pyridin-5-yl]-pyrazol-1-yl}-1-morpholin-4-ylethanone ("A32"),
2-{4-[3-(2-amino-6-ethylpyrimidin-4-yl)-1H-pyrrolo[2,3-b]pyridin-5-yl]-pyrazol-1-yl}ethanol ("A33"),
2-{4-[3-(2-amino-6-ethylpyrimidin-4-yl)-1H-pyrrolo[2,3-b]pyridin-5-yl]-pyrazol-1-yl}-N,N-dimethylacetamide ("A34"),
1-{2-amino-6-[5-(1-isopropyl-1H-pyrazol-4-yl)-1H-pyrrolo[2,3-b]pyridin-3-yl]pyrimidin-4-yl}butan-1-ol ("A35"),
1-{2-amino-6-[5-(1-isopropyl-1H-pyrazol-4-yl)-1H-pyrrolo[2,3-b]pyridin-3-yl]pyrimidin-4-yl}propan-2-ol ("A36"),
4-[5-(5-chlorothiophen-2-yl)-1H-pyrrolo[2,3-b]pyridin-3-yl]-6-ethylpyrimidin-2-ylamine ("A37"),
3-{2-amino-6-[5-(1-isopropyl-1H-pyrazol-4-yl)-1H-pyrrolo[2,3-b]pyridin-3-yl]pyrimidin-4-yl}propan-1-ol ("A38"),
4-{2-amino-6-{5-[1-(2-dimethylaminoethyl)-1H-pyrazol-4-yl]-1H-pyrrolo[2,3-b]pyridin-3-yl}pyrimidin-4-yl)butan-1-ol ("A39"),
4-{2-amino-6-[5-(1-isopropyl-1H-pyrazol-4-yl)-1H-pyrrolo[2,3-b]pyridin-3-yl]pyrimidin-4-yl}butan-1-ol ("A40"),
4-{5-[1-(2-dimethylaminoethyl)-1H-pyrazol-4-yl]-1H-pyrrolo[2,3-b]pyridin-3-yl}-6-[2-(4-methylpiperazin-1-yl)ethyl]pyrimidin-2-ylamine ("A41"),
4-{5-[5-(3-aminophenyl)oxazol-2-yl]-1H-pyrrolo[2,3-b]pyridin-3-yl}-6-ethylpyrimidin-2-ylamine ("A42"),
4-[5-(1-isopropyl-1H-pyrazol-4-yl)-1H-pyrrolo[2,3-b]pyridin-3-yl]-6-[2-(4-methylpiperazin-1-yl)ethyl]pyrimidin-2-ylamine ("A43"),
4-ethyl-6-{5-[1-(1-methanesulfonylpiperidin-4-yl)-1H-pyrazol-4-yl]-1H-pyrrolo[2,3-b]pyridin-3-yl}pyrimidin-2-ylamine (A"44"),
4-[2-amino-6-(1H-pyrrolo[2,3-b]pyridin-3-yl)pyrimidin-4-yl]butan-1-ol ("A45"),
1-(4-{4-[3-(2-amino-6-ethylpyrimidin-4-yl)-1H-pyrrolo[2,3-b]pyridin-5-yl]pyrazol-1-yl}piperidin-1-yl)ethanone ("A46"),
3-[2-amino-6-(1H-pyrrolo[2,3-b]pyridin-3-yl)pyrimidin-4-yl]-N-(3,4-difluorobenzyl)propionamide ("A47"), 1-[2-amino-6-(1H-pyrrolo[2,3-b]pyridin-3-yl)pyrimidin-4-yl]butan-1-ol ("A48"), 4-(2-morpholin-4-ylethyl)-6-(1H-pyrrolo[2,3-b]pyridin-3-yl)pyrimidin-2-ylamine ("A49"), 4-[2-(4-methylpiperazin-1-yl)ethyl]-6-(1H-pyrrolo[2,3-b]pyridin-3-yl)pyrimidin-2-ylamine ("A50"), 2-{4-[3-(2-amino-6-ethylpyrimidin-4-yl)-1H-pyrrolo[2,3-b]pyridin-5-yl]-pyrazol-1-yl}-N-methylacetamide ("A51"), 2-{4-[3-(2-amino-6-ethylpyrimidin-4-yl)-1H-pyrrolo[2,3-b]pyridin-5-yl]-pyrazol-1-yl}-N-cyclopropylacetamide "A52"), 1-{2-amino-6-[5-(1-isopropyl-1H-pyrazol-4-yl)-1H-pyrrolo[2,3-b]pyridin-3-yl]pyrimidin-4-yl}cyclohexanol ("A53"), 1-{2-amino-6-[5-(1-isopropyl-1H-pyrazol-4-yl)-1H-pyrrolo[2,3-b]pyridin-3-yl]pyrimidin-4-yl}cyclopentanol ("A54"), 1-{2-amino-6-[5-(1-isopropyl-1H-pyrazol-4-yl)-1H-pyrrolo[2,3-b]pyridin-3-yl]pyrimidin-4-yl}-1-phenylethanol ("A55"), 4-methylaminomethyl-6-{5-[1-(2-pyrrolidin-1-ylethyl)-1H-pyrazol-4-yl]-1H-pyrrolo[2,3-b]pyridin-3-yl}pyrimidin-2-ylamine ("A56");

4-(3-methylaminopropyl)-6-{5-[1-(2-pyrrolidin-1-ylethyl)-1H-pyrazol-4-yl]-1H-pyrrolo[2,3-b]pyridin-3-yl}pyrimidin-2-ylamine ("A57"), 2-{4-[3-(2-amino-6-butylpyrimidin-4-yl)-1H-pyrrolo[2,3-b]pyridin-5-yl]-pyrazol-1-yl}-1-piperidin-1-ylethanone ("A58"), 1-{2-amino-6-[5-(1-isopropyl-1H-pyrazol-4-yl)-1H-pyrrolo[2,3-b]pyridin-3-yl]pyrimidin-4-yl}-1-phenylpropan-1-ol ("A59"), {4-ethyl-6-[5-(1-isopropyl-1H-pyrazol-4-yl)-1H-pyrrolo[2,3-b]pyridin-3-yl]pyrimidin-2-yl}methylamine ("A60"), (4-{5-[1-(2-dimethylaminoethyl)-1H-pyrazol-4-yl]-1H-pyrrolo[2,3-b]pyridin-3-yl}-6-ethylpyrimidin-2-yl)methylamine ("A61"), {4-ethyl-6-[5-(1H-pyrazol-4-yl)-1H-pyrrolo[2,3-b]pyridin-3-yl]pyrimidin-2-yl}methylamine ("A62"), {4-ethyl-6-[5-(1-methyl-1H-pyrazol-4-yl)-1H-pyrrolo[2,3-b]pyridin-3-yl]-pyrimidin-2-yl}methylamine "A63", {4-ethyl-6-[5-(1-piperidin-4-yl-1H-pyrazol-4-yl)-1H-pyrrolo[2,3-b]pyridin-3-yl]pyrimidin-2-yl}methylamine ("A64"), 2-{4-[3-(6-ethyl-2-methylaminopyrimidin-4-yl)-1H-pyrrolo[2,3-b]pyridin-5-yl]pyrazol-1-yl}-1-piperidin-1-ylethanone ("A65"), 2-{4-[3-(6-ethyl-2-methylaminopyrimidin-4-yl)-1H-pyrrolo[2,3-b]pyridin-5-yl]pyrazol-1-yl}-1-pyrrolidin-1-ylethanone ("A66"), 2-{4-[3-(6-butyl-2-methylaminopyrimidin-4-yl)-1H-pyrrolo[2,3-b]pyridin-5-yl]pyrazol-1-yl}ethanol ("A67"), 2-{4-[3-(6-ethyl-2-methylaminopyrimidin-4-yl)-1H-pyrrolo[2,3-b]pyridin-5-yl]pyrazol-1-yl}ethanol ("A68"), (4-ethyl-6-{5-[1-(1-methylpiperidin-4-yl)-1H-pyrazol-4-yl]-1H-pyrrolo-[2,3-b]pyridin-3-yl}pyrimidin-2-yl)methylamine ("A69"), {4-butyl-6-[5-(1-piperidin-4-yl-1H-pyrazol-4-yl)-1H-pyrrolo[2,3-b]pyridin-3-yl]pyrimidin-2-yl}methylamine ("A70"), (4-butyl-6-{5-[1-(1-methylpiperidin-4-yl)-1H-pyrazol-4-yl]-1H-pyrrolo-[2,3-b]pyridin-3-yl}pyrimidin-2-yl)methylamine ("A71"), 2-{4-[3-(6-ethyl-2-methylaminopyrimidin-4-yl)-1H-pyrrolo[2,3-b]pyridin-5-yl]pyrazol-1-yl}-N-(1H-indol-5-yl)propionamide ("A72"), 1-(3,4-dihydro-2H-quinolin-1-yl)-2-{4-[3-(6-ethyl-2-methylaminopyrimidin-4-yl)-1H-pyrrolo[2,3-b]pyridin-5-yl]pyrazol-1-yl}ethanone ("A73"), 3-(6-benzyl-2-methoxypyrimidin-4-yl)-5-(1-isopropyl-1H-pyrazol-4-yl)-1H-pyrrolo[2,3-b]pyridine ("A74"), 3-(6-ethyl-2-methoxypyrimidin-4-yl)-5-(1-isopropyl-1H-pyrazol-4-yl)-1H-pyrrolo[2,3-b]pyridine ("A75"), 3-(6-ethyl-2-methanesulfonylpyrimidin-4-yl)-5-(1-isopropyl-1H-pyrazol-4-yl)-1H-pyrrolo[2,3-b]pyridine ("A76"), 3-(6-ethyl-2-methylsulfanylpyrimidin-4-yl)-1H-pyrrolo[2,3-b]pyridine ("A77"), 4-[5-(4-aminomethylphenyl)-1H-pyrrolo[2,3-b]pyridin-3-yl]-6-ethylpyrimidin-2-ylamine ("A81"), 3-[2-amino-6-(1H-pyrrolo[2,3-b]pyridin-3-yl)pyrimidin-4-yl]-1-morpholin-4-ylpropan-1-one ("A82"), 3-[2-amino-6-(1H-pyrrolo[2,3-b]pyridin-3-yl)pyrimidin-4-yl]-N-(2-dimethylaminoethyl)propionamide ("A83"), 4-(3-aminopropyl)-6-[5-(1-isobutyl-1H-pyrazol-4-yl)-1H-pyrrolo[2,3-b]-pyridin-3-yl]pyrimidin-2-ylamine ("A84"), 4-butyl-6-{5-[1-(2-dimethylaminoethyl)-1H-pyrazol-4-yl]-1H-pyrrolo-[2,3-b]pyridin-3-yl}pyrimidin-2-ylamine ("A85"), 1-(4-{4-[3-(2-amino-6-butylpyrimidin-4-yl)-1H-pyrrolo[2,3-b]pyridin-5-yl]pyrazol-1-yl}piperidin-1-yl)ethanone ("A86"), 4-butyl-6-[5-(1-piperidin-4-yl-1H-pyrazol-4-yl)-1H-pyrrolo[2,3-b]pyridin-3-yl]pyrimidin-2-ylamine ("A87"), 2-{4-[3-(2-amino-6-butylpyrimidin-4-yl)-1H-pyrrolo[2,3-b]pyridin-5-yl]-pyrazol-1-yl}ethanol ("A88"), 4-butyl-6-{5-[1-(1-methylpiperidin-4-yl)-1H-pyrazol-4-yl]-1H-pyrrolo-[2,3-b]pyridin-3-yl}pyrimidin-2-ylamine ("A89"), (S)-1-{2-amino-6-[5-(1-isopropyl-1H-pyrazol-4-yl)-1H-pyrrolo[2,3-b]-pyridin-3-yl]pyrimidin-4-yl}butan-1-ol ("A90"), R)-1-{2-amino-6-[5-(1-isopropyl-1H-pyrazol-4-yl)-1H-pyrrolo[2,3-b]-pyridin-3-yl]pyrimidin-4-yl}butan-1-ol ("A91"), 2-{4-[3-(2-amino-6-ethylpyrimidin-4-yl)-1H-pyrrolo[2,3-b]pyridin-5-yl]-pyrazol-1-yl}-N-methylacetamide ("A92"), N-(3-{2-amino-6-[5-(1-isopropyl-1H-pyrazol-4-yl)-1H-pyrrolo[2,3-b]pyridin-3-yl]pyrimidin-4-yl}propyl)acetamide ("A97"), 4-ethyl-6-{5-[1-(3-fluorobenzyl)-1H-pyrazol-4-yl]-1H-pyrrolo[2,3-b]pyridin-3-yl}pyrimidin-2-ylamine ("A98"), 4-{5-[1-(3,4-difluorobenzyl)-1H-pyrazol-4-yl]-1H-pyrrolo[2,3-b]pyridin-3-yl}-6-ethylpyrimidin-2-ylamine ("A99"), 3-{2-amino-6-[5-(1-isopropyl-1H-pyrazol-4-yl)-1H-pyrrolo[2,3-b]pyridin-3-yl]pyrimidin-4-yl}-N,N-dimethylpropionamide ("A101"), 1-{2-amino-6-[5-(1-isopropyl-1H-pyrazol-4-yl)-1H-pyrrolo[2,3-b]pyridin-3-yl]pyrimidin-4-yl}-2-methylpropan-1-ol ("A102"), 1-{2-amino-6-[5-(1-isopropyl-1H-pyrazol-4-yl)-1H-pyrrolo[2,3-b]pyridin-3-yl]pyrimidin-4-yl}propan-1-ol ("A103"), 1-{2-amino-6-[5-(1-isopropyl-1H-pyrazol-4-yl)-1H-pyrrolo[2,3-b]pyridin-3-yl]pyrimidin-4-yl}-3-methylbuta n–1-ol ("A104"), 4-cyclohexyl-6-(1H-pyrrolo[2,3-b]pyridin-3-yl)pyrimidin-2-ylamine ("A105"), 2-{4-[3-(2-amino-6-butylpyrimidin-4-yl)-1H-pyrrolo[2,3-b]pyridin-5-yl]-pyrazol-1-yl}-1-pyrrolidin-1-ylethanone ("A106"), 4-(3-imidazol-1-ylpropyl)-6-[5-(1-isopropyl-1H-pyrazol-4-yl)-1H-pyrrolo-[2,3-b]pyridin-3-yl]pyrimidin-2-ylamine ("A108"), 4-(2-imidazol-1-ylethyl)-6-[5-(1-isopropyl-1H-pyrazol-4-yl)-1H-pyrrolo-[2,3-b]pyridin-3-yl]pyrimidin-2-ylamine ("A110"), 4-cyclohexyl-6-[5-(1-isopropyl-1H-pyrazol-4-yl)-1H-pyrrolo[2,3-b]pyridin-3-yl]pyrimidin-2-ylamine ("A111"), 4-[2-amino-6-(1H-pyrrolo[2,3-b]pyridin-3-yl)pyrimidin-4-yl]-4-hydroxypiperidine-1-carboxylic acid benzyl ester ("A113"), 4-{2-amino-6-[5-(1-isopropyl-1H-pyrazol-4-yl)-1H-pyrrolo[2,3-b]pyridin-3-yl]pyrimidin-4-yl}-1-isopropylpiperidin-4-ol ("A114"), {2-amino-6-[5-(1-isopropyl-1H-pyrazol-4-yl)-1H-pyrrolo[2,3-b]pyridin-3-yl]pyrimidin-4-yl}phenylmethanol ("A115"), 4-{2-amino-6-[5-(1-isopropyl-1H-pyrazol-4-yl)-1H-pyrrolo[2,3-b]pyridin-3-yl]pyrimidin-4-yl}-1-[2-(4-fluorophenyl)ethyl]piperidin-4-ol ("A116"), 2-{4-[3-(2-amino-6-ethylpyrimidin-4-yl)-1H-pyrrolo[2,3-b]pyridin-5-yl]-pyrazol-1-yl}-N-(1H-indol-5-yl)propionamide ("A121"), 4-{2-amino-6-[5-(1-isopropyl-1H-pyrazol-4-yl)-1H-pyrrolo[2,3-b]pyridin-3-yl]pyrimidin-4-yl}-4-hydroxypiperidine-1-carboxylic acid benzyl ester ("A122"), (R)-1-{2-amino-6-[5-(1-isopropyl-1H-pyrazol-4-yl)-1H-pyrrolo[2,3-b]-pyridin-3-yl]pyrimidin-4-yl}-1-phenylethanol ("A123"), (S)-1-{2-amino-6-[5-(1-isopropyl-1H-pyrazol-4-yl)-1H-pyrrolo[2,3-b]-pyridin-3-yl]pyrimidin-4-yl}-1-phenylethanol ("A124"), 4-{2-amino-6-[5-(1-isopropyl-1H-pyrazol-4-yl)-1H-pyrrolo[2,3-b]pyridin-3-yl]pyrimidin-4-yl}piperidin-4-ol ("A125")

or

2-{4-[3-(2-amino-6-ethylpyrimidin-4-yl)-1H-pyrrolo[2,3-b]pyridin-5-yl]-pyrazol-1-yl}-1-(3,4-dihydro-2H-quinolin-1-yl)ethanone ("A128"), The invention also relates to a set (kit) consisting of separate packs of (a) an effective amount of a compound of the formula I and/or pharmaceutically usable derivatives, solvates and stereoisomers thereof, including mixtures thereof in all ratios, and (b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically usable derivatives, solvates and stereoisomers thereof, including mixtures thereof in all ratios, and an effective amount of a further medicament active ingredient in dissolved or lyophilised form.

Use

The present compounds are suitable as pharmaceutical active ingredients for mammals, especially for humans, in the treatment and control of cancer diseases.

The present invention encompasses the use of the compounds of the formula I and/or physiologically acceptable salts and solvates thereof for the preparation of a medicament for the treatment or prevention of cancer. Preferred carcinomas for the treatment originate from the group cerebral carcinoma, urogenital tract carcinoma, carcinoma of the lymphatic system, stomach carcinoma, laryngeal carcinoma and lung carcinoma bowel cancer. A further group of preferred forms of cancer are monocytic leukaemia, lung adenocarcinoma, small-cell lung carcinomas, pancreatic cancer, glioblastomas and breast carcinoma.

Also encompassed is the use of the compounds of the formula I and/or physiologically acceptable salts and solvates thereof for the preparation of a medicament for the treatment and/or control of a tumour-induced disease in a mammal, in which to this method a therapeutically effective amount of a compound according to the invention is administered to a sick mammal in need of such treatment. The therapeutic amount varies according to the particular disease and can be determined by the person skilled in the art without undue effort.

Particular preference is given to the use for the treatment of a disease, where the disease is a solid tumour.

The solid tumour is preferably selected from the group of tumours of the squamous epithelium, the bladder, the stomach, the kidneys, of head and neck, the oesophagus, the cervix, the thyroid, the intestine, the liver, the brain, the prostate, the urogenital tract, the lymphatic system, the stomach, the larynx and/or the lung.

The solid tumour is furthermore preferably selected from the group lung adenocarcinoma, small-cell lung carcinomas, pancreatic cancer, glioblastomas, colon carcinoma and breast carcinoma.

Preference is furthermore given to the use for the treatment of a tumour of the blood and immune system, preferably for the treatment of a tumour selected from the group of acute myeloid leukaemia, chronic myeloid leukaemia, acute lymphatic leukaemia and/or chronic lymphatic leukaemia.

The invention furthermore relates to the use of the compounds according to the invention for the treatment of bone pathologies, where the bone pathology originates from the group osteosarcoma, osteoarthritis and rickets.

The compounds of the formula I may also be administered at the same time as other well-known therapeutic agents that are selected for their particular usefulness against the condition that is being treated.

The present compounds are also suitable for combination with known anti-cancer agents. These known anti-cancer agents include the following: oestrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors and further angiogenesis inhibitors. The present compounds are particularly suitable for administration at the same time as radiotherapy.

"Oestrogen receptor modulators" refers to compounds which interfere with or inhibit the binding of oestrogen to the receptor, regardless of mechanism. Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]phenyl 2,2-dimethylpropanoate, 4,4'-dihydroxybenzophenone-2,4-dinitrophenylhydrazone and SH646.

"Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cis-retinoic acid, 9-cis-retinoic acid, a-difluoromethylornithine, ILX23-7553, trans-N-(4'-hydroxyphenyl)retinamide and N-4-carboxyphenylretinamide.

"Cytotoxic agents" refers to compounds which result in cell death primarily through direct action on the cellular function or inhibit or interfere with cell myosis, including alkylating agents, tumour necrosis factors, intercalators, microtubulin inhibitors and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cisaminedichloro(2-methylpyridine)platinum, benzylguanine, glufosfamide, GPX100, (trans,trans,trans)bis-mu-(hexane-1,6-diamine)-mu-[diamineplatinum(III)]bis[diamine(chloro)platinum(II)]tetrachloride, diarisidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755 and 4-demethoxy-3-deamino-3-aziridinyl-4-methylsulfonyldaunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzenesulfonamide, anhydrovinblastine, N,N-dimethyl-L-valyl-L-valyl-N-methyl-L-valyl-L-prolyl-L-proline-t-butylamide,(SEQ ID NO: 1), TDX258 and BMS188797.

Topoisomerase inhibitors are, for example, topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4':b,7]indolizino[1,2b]quinoline-10,13(9H, 15H)-dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxyetoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]phenanthridinium, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7 H-indeno[2,1-c]quinolin-7-one and dimesna.

"Antiproliferative agents" include antisense RNA and DNA oligonucleotides such as G3139, ODN698, RVASK-RAS, GEM231 and INX3001 and anti-metabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, neizarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N'-[4-deoxy-4-[N2-[2(E),4(E)-tetradecadienoyl]glycylamino]-L-g lycero-B-L-mannoheptopyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,1'-diazatetracyclo(7.4.1.0.0)tetradeca-2, 4,6-trien-9-yiacetic acid ester, swainsonine, lometrexol, dexrazoxane, methioninase, 2'-cyano-2'-deoxy-N4-palmitoyl-1-B-Darabinofuranosyl cytosine and 3-aminopyridine-2-carboxaldehyde thiosemicarbazone. "Antiproliferative agents" also include monoclonal antibodies to growth factors other than those listed under "angiogenesis inhibitors", such as trastuzumab, and tumour suppressor genes, such as p53, which can be delivered via recombinant virus-mediated gene transfer (see U.S. Pat. No. 6,069,134, for example).

Evidence of the Action of Pharmacological Inhibitors on the Proliferation/Vitality of Tumour Cells in vitro 1. Background In the present experiment description, the inhibition of tumour cell proliferation/tumour cell vitality by active ingredients is described.

The cells are sown in a suitable cell density in microtitre plates (96-well format) and the test substances are added in the form of a concentration series. After four further days of cultivation in serum-containing medium, the tumour cell proliferation/tumour cell vitality can be determined by means of an Alamar Blue test system.

2. Experimental Procedure 2.1 Cell Culture

For example commercially available colon carcinoma cell lines, ovary cell lines, prostate cell lines or breast cell lines, etc.

The cells are cultivated in medium. At intervals of several days, the cells are detached from the culture dishes with the aid of trypsin solution and sown in suitable dilution in fresh medium. The cells are cultivated at 37° Celsius and 10% $CO_2$.

2.2. Sowing of the Cells

A defined number of cells (for example 2000 cells) per culture/well in a volume of 180 µl of culture medium are sown in microtitre plates (96 well cell-culture plates) using a multichannel pipette. The cells are subsequently cultivated in a CO2 incubator (37° C. and 10% CO2).

2.3. Addition of the Test Substances

The test substances are dissolved, for example, in DMSO and subsequently employed in corresponding concentration (if desired in a dilution series) in the cell culture medium. The dilution steps can be adapted depending on the efficiency of the active ingredients and the desired spread of the concentrations. Cell culture medium is added to the test substances in corresponding concentrations. The addition of the test substances to the cells can take place on the same day as the sowing of the cells. To this end, in each case 20 µl of substance solution from the predilution plate are added to the cultures/wells. The cells are cultivated for a further 4 days at 37° Celsius and 10% $CO_2$.

2.4. Measurement of the Colour Reaction

In each case, 20 µl of Alamar Blue reagent are added per well, and the microtitre plates are incubated, for example, for a further seven hours in a CO2 incubator (at 37° C. and 10% CO2). The plates are measured in a reader with a fluorescence filter at a wavelength of 540 nm. The plates can be shaken gently immediately before the measurement.

3. Evaluation

The absorbance value of the medium control (no cells and test substances used) is subtracted from all other absorbance values. The controls (cells without test substance) are set equal to 100 percent, and all other absorbance values are set in relation thereto (for example in % of control):

Calculation:

$$100 * \frac{\text{(value with cells and test substance} - \text{value of medium control)}}{\text{(value with cells} - \text{value of medium control)}}$$

$IC_{50}$ values (50% inhibition) are determined with the aid of statistics programs, such as, for example, RS1.

$IC_{50}$ data for compounds according to the invention are shown in Table 1.

4. Test for the Inhibition of PDK1

The experimental batches are carried out in a flashplate system with 384 wells/microtitration plate.

In each case, the PDK1 sample $His_6$-PDK1(SEQ ID NO: 2)(1-50)(3.4 nM), the PDK1 substrate biotin-bA-bA-KT-FCGTPEYLAPEVRREPRILSEEEQEMFRDFDYIADWC (SEQ ID NO: 3) (400 nM), 4 μM ATP (with 0.2 μCi of $^{33}$P-ATP/well) and the test substance in 50 μl of conventional experimental solution per well are incubated at 30° C. for 60 min. The test substances are employed in corresponding concentrations (if desired in a dilution series). The control is carried out without test substance. The reaction is stopped using standard methods and washed. The activity of the kinase is measured via the incorporated radioactivity in top count. In order to determine the non-specific kinase reaction (blank value), the experimental batches are carried out in the presence of 100 nM staurosporin.

5. Evaluation

The radioactivity (decompositions per minute) of the blank value (no use of test substance in the presence of staurosporin) is subtracted from all other radioactivity values. The controls (kinase activity without test substance) are set equal to 100 percent and all other radioactivity values (after subtracting the blank value) are expressed set in relation thereto (for example in % of the control).

Calculation:

$$100 * \frac{\text{(value of the kinase activity with test substance} - \text{blank value)}}{\text{(value of the control} - \text{blank value)}} = \% \text{ of the control}$$

$IC_{50}$ values (50% inhibition) are determined with the aid of statistics programmes, such as, for example, RS1. $IC_{50}$ data of compounds according to the invention are indicated in Table 1.

| Material | Order No. | Manufacturer |
|---|---|---|
| Microtitre plates for cell culture (Nunclon Surface 96-well plate) | | 167008 Nunc |
| DMEM | P04-03550 | Pan Biotech |
| PBS (10x) Dulbecco | 14200-067 | Gibco |

-continued

| Material | Order No. | Manufacturer |
|---|---|---|
| 96-well plates (polypropylene) | | 267334 Nunc |
| AlamarBlue ™ | BUF012B | Serotec |
| FCS | 1302 | Pan Biotech GmbH |
| Trypsin/EDTA solution 10x | L 2153 | Biochrom AG |
| 75 cm² culture bottles | 353136 | BD Falcon |
| A2780 | 93112519 | ECACC |
| Colo205 | CCL222 | ATCC |
| MCF7 | HTB22 | ATCC |
| PC3 | CRL-1435 | ATCC |
| 384-well flash plates | SMP410A001PK | Perkin Elmer |

APCI-MS (atmospheric pressure chemical ionisation-mass spectrometry) $(M+H)^+$.

HPLC Gradient System

Column:

RP-select B (Merck KGaA, Cat. 1.050981)

Eluents:

Eluent A: water+0.01% of TFA

Eluent B: acetonitrile+0.01% of TFA

Flow rate: 1.5 ml/min

Injection volume: 10 μl

Gradient:

0 min 20% of B 6 min 100% of B 7 min 100% of B 158 min 20% of B 9 min 20% of B

EXAMPLE 1

The preparation of 4-{5-[1-(2-dimethylaminoethyl)-1H-pyrazol-4-yl]-1H-pyrrolo[2,3-b]pyridin-3-yl}-6-ethylpyrimidin-2-ylamine ("A1") is carried out analogously to the following scheme

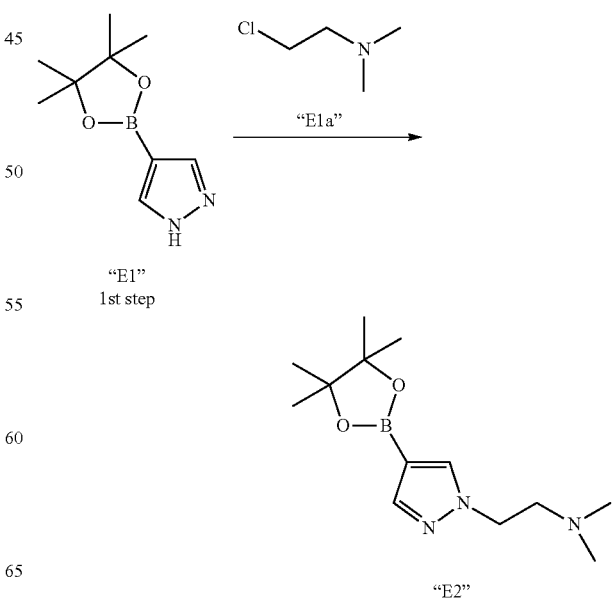

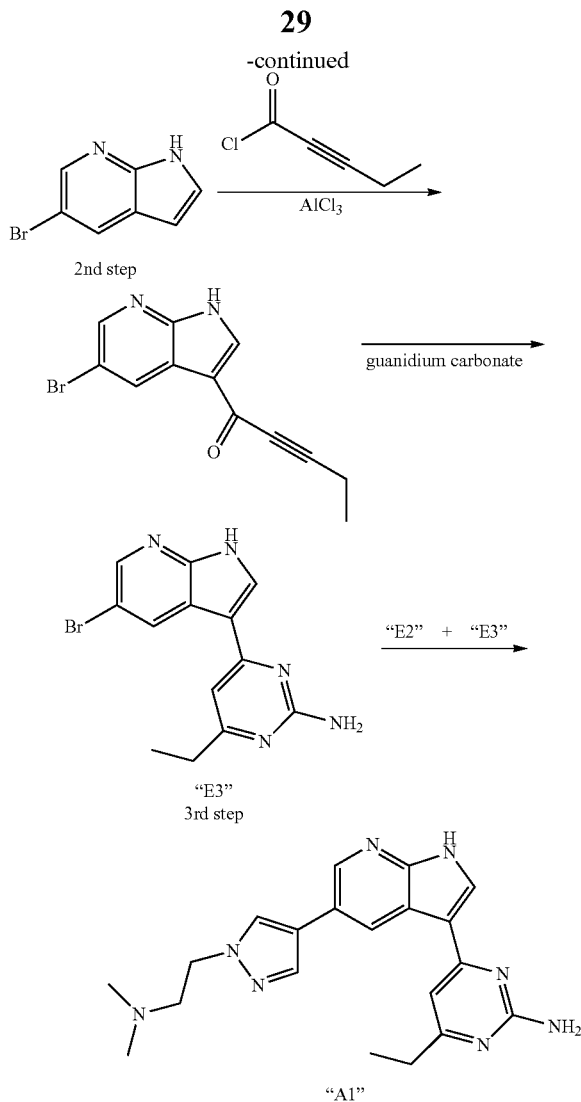

1.1 For the preparation of "E2", a suspension of 5.94 g (30 mmol) of pyrazole-4-boronic acid and "E1" 19.55 g (60 mmol) of caesium carbonate in 60 ml of acetonitrile is stirred at room temperature for 15 minutes. 6.48 g (45 mmol) of 2-dimethylaminoethyl chloride hydrochloride ("E1a") are added, and the mixture is stirred at room temperature for 2 days, filtered off with suction and rinsed with acetonitrile. The filtrate is evaporated, and a saturated NaCl solution is added, and the mixture is extracted three times with ethyl acetate. The organic phase is washed with water, dried over sodium sulfate and evaporated: 3.5 g of yellowish, gradually crystallising oil is obtained. According to NMR, it was essentially a mixture of product and pinacol in the ratio 1:1. This gives a content of about 64% (yield 21%)

1.2 For the preparation of "E2", a suspension of 2 g (10.15 mmol) of 5-bromo-7-azaindole and 6.77 g (50.75 mmol) of aluminium chloride in 174 ml of dichloromethane is stirred at room temperature for 2 h. A solution of 13.19 mmol of 2-pentynoyl chloride in dichloromethane (prepared from 1.29 g (13.19 mmol) of 2-pentynoic acid dissolved in 70 ml of dichloromethane and treated at 0° C. with stirring with 1.36 ml of oxalyl chloride and 1 drop of N,N-dimethylformamide and stirred at room temperature for a further 2 h) is slowly added dropwise to the red suspension. The reaction mixture is stirred overnight and neutralised using a saturated sodium hydrogencarbonate solution. The precipitated aluminium hydroxide is filtered off with suction, and the filtrate is transferred into a separating funnel. The dichloromethane phase is subsequently separated off and washed once with water and once again with the sodium hydrogencarbonate solution, dried over sodium sulfate, filtered and evaporated. The solid residue is digested with ethyl acetate and petroleum ether and filtered off with suction, giving 1.44 g of product as brown crystals (45% yield).

1.3 For the preparation of "E3", a suspension of 1.44 g (5.2 mmol) of intermediate 1, 1.875 g (10.4 mmol) of guanidinium carbonate and 1.8 g (13 mmol) of potassium carbonate in 30 ml of ethylene glycol monomethyl ether is refluxed for 4 h. The undissolved potassium carbonate is filtered off with suction and slurried a number of times with ethyl acetate and filtered off with suction. The combined organic phase is diluted with ethyl acetate, washed twice with water, dried over sodium sulfate, filtered and evaporated. The solid residue is digested with ethyl acetate and petroleum ether and filtered off with suction. The product is obtained as orange crystals (857 mg, 48% yield).

1.4 For the preparation of "A1", a mixture of 100 mg (0.315 mmol) of "E3", 1.8 equivalent of boronic acid "E2", 36.4 mg (0.032 mmol) of tetrakis(triphenylphosphine)palladium(0) and 0.9 ml of a 2 molar sodium carbonate solution in 1.2 ml of N,N-dimethylformamide is degassed with nitrogen for 2 min and subsequently heated at 120° C. for 30 min in a microwave synthesiser (CEM, Discover). The reaction mixture is diluted with ethyl acetate and water and filtered off. The filtrate is transferred into a separating funnel, and the phases are separated. The aqueous phase is extracted a further twice with ethyl acetate. The organic phase is dried using sodium sulfate, filtered and evaporated. The residue is dissolved in 1 ml of N,N-dimethylformamide and purified via a reversed phase chromatography column. The fractions are combined, rendered basic using a concentrated sodium hydroxide solution and extracted 3 times with ethyl acetate. The organic phase is dried over sodium sulfate, filtered and evaporated. The product was lyophilised, giving 28 mg of "A1" in the form of white crystals (24% yield).

Solid; ESI 376.

$^1$H-NMR (d$_6$-DMSO, 500 MHz): δ=1.24 (t, J=7.65 Hz, 3H), 2.21 (s, 6H), 2.53 (q, J=7.61 Hz, 2H), 2.73 (t, J=6.65 Hz, 2H), 4.24 (t, J=6.63 Hz, 2H), 6.48 (s, 2H), 6.99 (s, 1H), 8.07 (s, 1H), 8.31 (s, 2H), 8.55 (d, J=2.17 Hz, 1H), 9.03 (d, J=2.20 Hz, 1H), 12.09 (s, 1H) ppm.

EXAMPLE 2

Preparation of 2-{4-[3-(2-amino-6-butylpyrimidin-4-yl)-1H-pyrrolo[2,3-b]pyridin-5-yl]pyrazol-1-yl}-1-piperidin-1-yl-et Hanone ("A58")

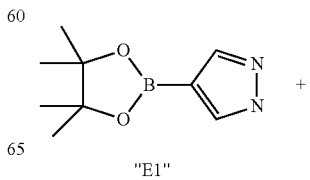

-continued

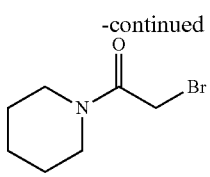

"E4"

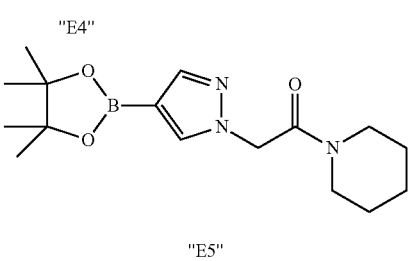

"E5"

A suspension of 4-(4,4,5,5-tetramethyl-1,3,2-dioxaborolan-2-yl)-1H-pyrazole (3.5 g, 18 mmol) and caesium carbonate (14.25 g, 43.7 mmol) in acetonitrile (50 ml) is stirred at room temperature for 30 min. 2-Bromo-1-piperidin-1-ylethanone (4.5 g, 21.8 mmol) dissolved in acetonitrile (20 ml) is subsequently added dropwise and stirred at room temperature for 18 h. The solid was filtered off, the residue was washed with acetonitrile, and the filtrate was evaporated in vacuo. The oily residue is taken up in dichloromethane and extracted with sat. NaCl soln. The organic phase is dried over MgSO4, filtered and re-evaporated, giving E5 (3.56 g, 11.1 mmol) as an oily residue in 62% yield.

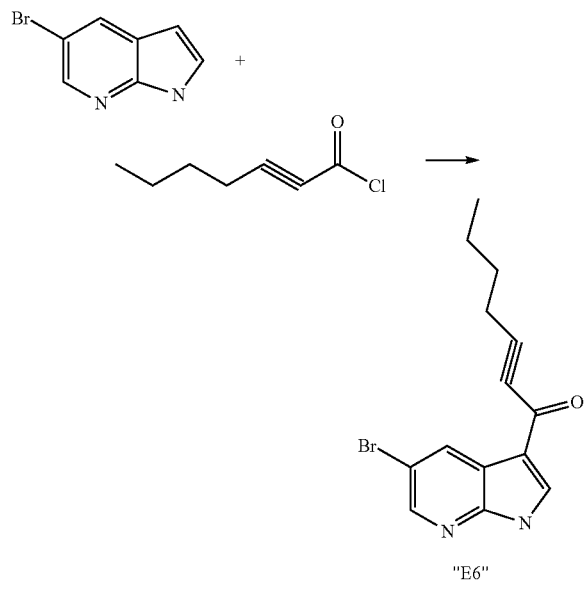

"E6"

5-Bromo-1H-pyrrolo (2,3)pyridine (1.702 g, 8.64 mmol) and aluminium chloride (5.76 g, 43.2 mmol) were suspended in dichloromethane (100 ml) and stirred at room temperature for 2 h. A solution of the alkynylic acid chloride (1.5 g, 10.3 mmol) in dichloromethane (5 ml) was slowly added dropwise to the red suspension. The reaction mixture was stirred overnight.

The reaction was carefully neutralised using sat. NaHCO3 soln. with ice-cooling. The aqueous phase was separated off, and the organic phase was washed a further 2× with water, dried using sodium sulfate and distilled off to a residue in a Rotavapor.

Ethyl acetate/hexane was added to the crude mixture, and the precipitate was filtered off with suction, giving E6 as a pale-grey solid (1.2 g, 3.93 mmol) in 46% yield.

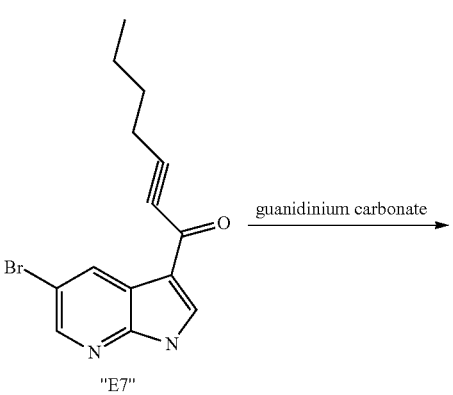

"E7"

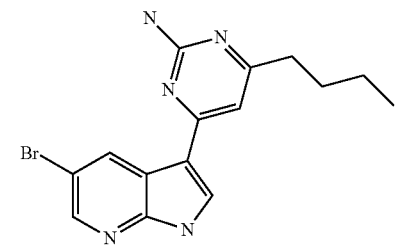

"E8"

Ethylene glycol monomethyl ether was added to E7, guanidinium carbonate and potassium carbonate were added, and the mixture was stirred under reflux overnight.

Water was added to the reaction, and the mixture was extracted by shaking 2× with ethyl acetate. The combined organic phases were washed 3× with water, dried using sodium sulfate and evaporated to dryness in a Rotavapor, giving "E8" as a grey solid residue. The crude mixture is immediately reacted further.

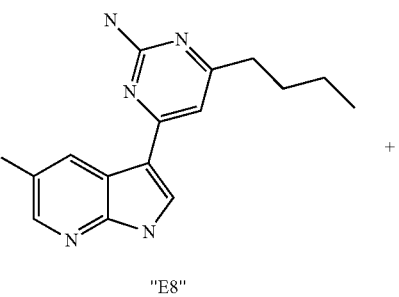

"E8"

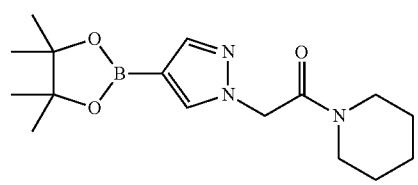

"E5"

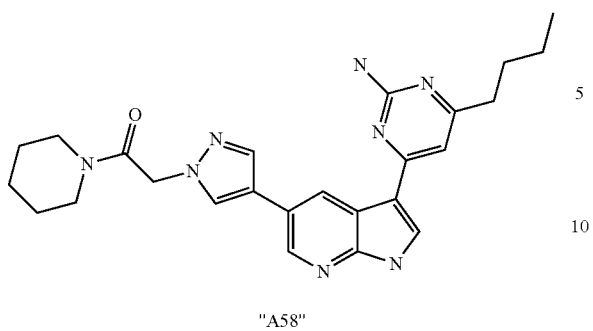

"A58"

"E8" "E5" "A58" "E8" (100 mg, 0.289 mmol), "E5" (330 mg, 0.517 mmol), Pd(PPh₃)₄ (17 mg), 2N aqueous Na₂CO₃ solution (800 µl) and DMF (1.6 ml) are suspended in a microwave vessel. The mixture is flushed with nitrogen and subsequently stirred at 120° C. for 30 min in a microwave (Biotage). The solid is filtered off, and the residue is washed with MeOH. The filtrate is evaporated in vacuo, and the residue is purified by preparative HPLC. Yield: 41 mg (0.083 mmol), 29%.

EXAMPLE 3

Preparation of 1-{2-amino-6-[5-(1-isopropyl-1H-pyrazol-4-yl)-1H-pyrrolo-[2,3-b]pyridin-3-yl]pyrimidin-4-yl}butan-1-ol ("A35")

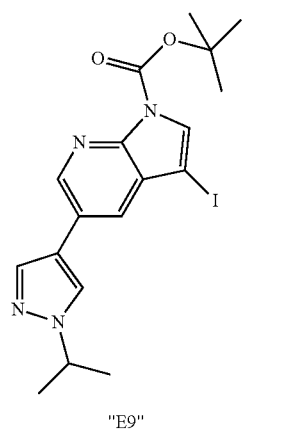

"E9"

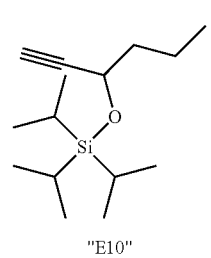

"E10"

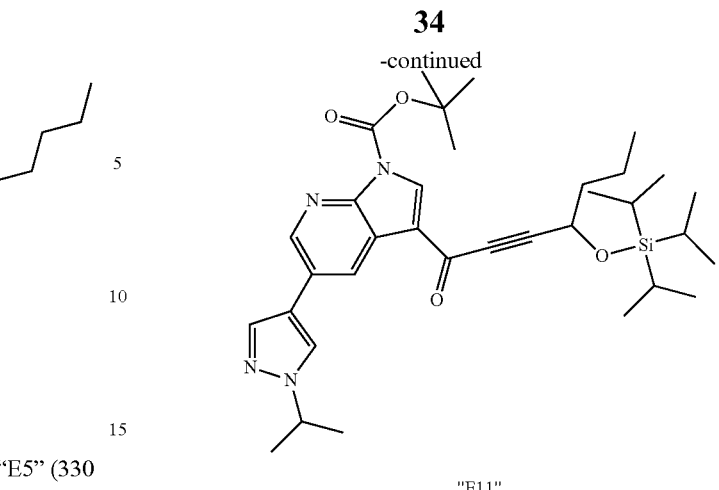

"E11"

The starting materials and reagents are combined in the following sequence: the solids caesium carbonate (1.206 g, 3.70 mmol), CuI (5.642, 0.03 mmol), Pd(OAc)₂ ( ) 16 mg), Mo(CO)₆, (0.586 g, 2.222 mmol) followed by "E9" dissolved in acetonitrile (2.5 ml) and "E10" dissolved in toluene (2.5 ml), as THE final starting material P(Bu)₃ (112 µl, 0.444 mmol). The mixture is stirred at 80° C. for 5 min.

The reaction mixture was evaporated in a rotary evaporator below 30° C. and chromatographed (RediSep column: 40 g of silica, detection wavelength (red): 254 nm, flow rate: 40 ml/min, conditioning volume: 240.0 ml, run time 32.0 min, eluent A: L1 pet ether; eluent B: B1 ethyl acetate). The fractions containing the product are evaporated below 30° C., giving "E11" as yellow oil (390 mg, 0.64 mmol) in 43% yield.

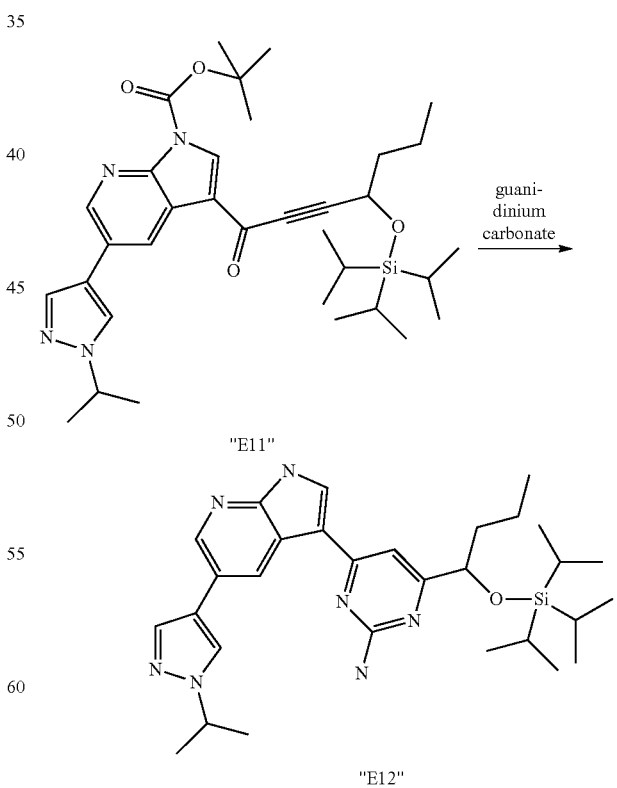

"E11"

guanidinium carbonate →

"E12"

"E11" (390 mg, 0.643 mmol), guanidinium carbonate (173.67 mg, 0.964 mmol) and potassium carbonate (444.08 mg, 3.213 mmol) are suspended in ethylene glucol monomethyl ether (3 ml) and heated at 120° C. for 3 days. The reaction mixture is extracted 3 times with ethyl acetate and water. The organic phases are combined, dried over sodium sulfate and evaporated, giving E12 (318 mg, 0.337 mmol) in 52% yield. "E12" is reacted further without purification.

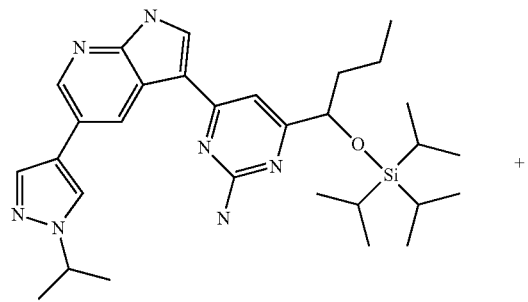

"E12"

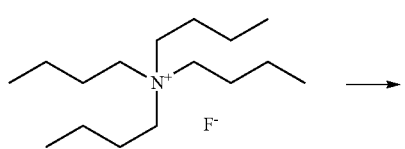

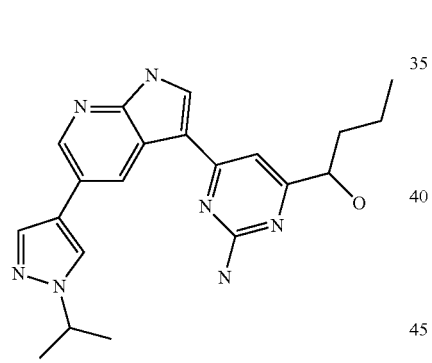

"A35"

TBAF (1.347 ml, 1.34 mmol as 1 M soln. in THF) is added to a solution of "E12" (318 mg, 0.337 mmol) in THF (2.5 ml), and the mixture is stirred at room temperature for 18 h. The reaction mixture is evaporated in a Rotavapor. The residue is dissolved in 2 ml of MeOH and chromatographed via prep HPLC. The fractions are combined, rendered basic using conc. NaOH and extracted 3 times with EA. The organic phases are combined, dried over sodium sulfate and evaporated. The crystals are digested with PE/EA, giving "A35" as yellow crystals (62.6 mg, 48%).

1H-NMR (d6-DMSO, 400 MHz): δ=0.74 (t, J=7.3 Hz, 3H), 1.26 (m, 2H), 1.32 (d, J=6.6 Hz, 6H), 1.41 (m, 1H), 1.55 (m, 1H), 4.15 (q, J=3.9 Hz, 1H), 4.37 (m, 1H), 5.05 (s, 1H), 6.39 (s, 2H), 6.97 (s, 1H), 7.89 (s, 1H), 8.13 (m, 2H), 8.41 (d, J=1.9 Hz, 1H), 8.87 (d, J=1.8 Hz, 1H), 11.93 (s, 1H) ppm.

EXAMPLE 4

Preparation of 1-{2-amino-6-[5-(1-isopropyl-1H-pyrazol-4-yl)-1H-pyrrolo-[2,3-b]pyridin-3-yl]pyrimidin-4-yl}-1-phenylpropan-1-ol ("A57")

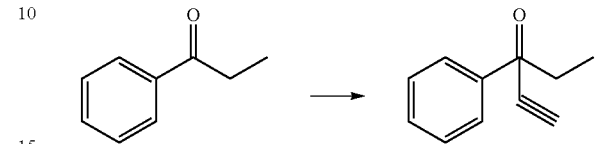

A solution of propiophenone in THF (0.2 ml, 1.505 mmol) is slowly added dropwise at room temperature with stirring to a solution of ethynylmagnesium bromide (4 ml, 2.0 mmol, 0.5 M in THF) in THF (5 ml). The slightly yellow reaction solution was stirred at RT for 1 h. The reaction mixture is acidified using 1N HCl, during which a turbidity initially formed which disappeared with an increase in the pH into the acidic region. Diethyl ether was added to the solution, the aqueous phase was separated off, and the organic phase was extracted once with water. The organic phase was dried using sodium sulfate, filtered off and evaporated to dryness, giving 3-phenylpent-1-yn-3-ol (233 mg, 0.001 mol) in 65% yield. The crude mixture is reacted further without further purification.

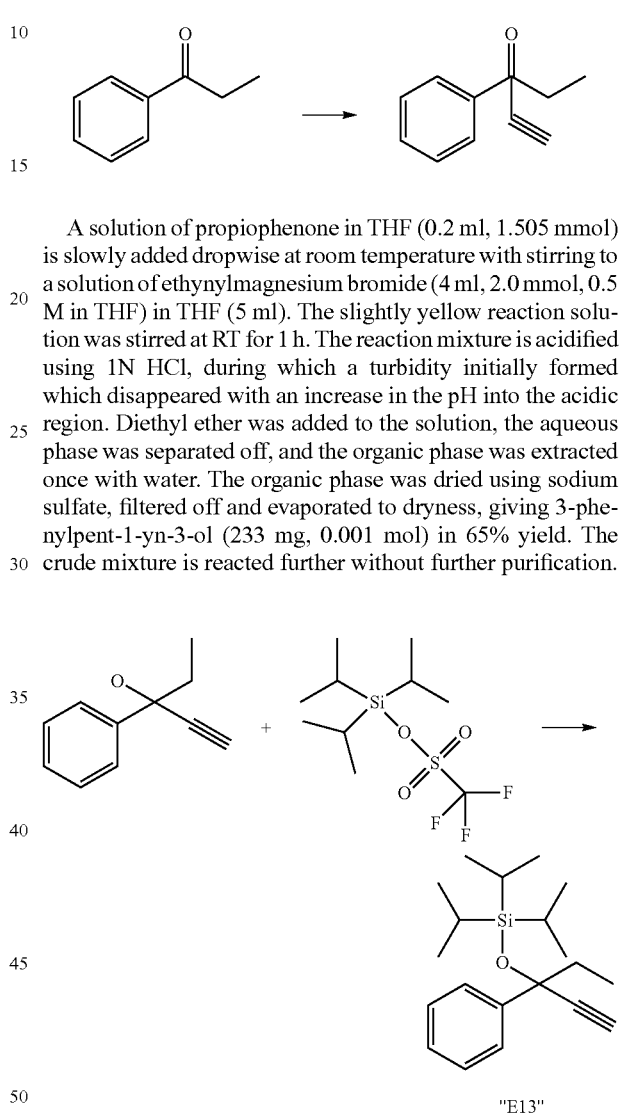

"E13"

2,6-Dimethylpyridine (4.950 ml, 45.5 mmol) is added to a solution of 3-phenylpent-1-yn-3-ol (3.4 g, 21.2 mmol) in dichloromethane (80 ml). The mixture is cooled to 0° C., and TIPS triflate (8.5 ml, 31.9 mmol) is then slowly added. The mixture is warmed to room temperature and left to stir for a further 18 h. Sat. ammonium chloride soln. is added to the reaction mixture, the organic phase is separated off, and the aqueous phase is extracted twice with dichloromethane. The combined organic phases are dried over magnesium sulfate, the solid is filtered off and evaporated to dryness. The residue is chromatographed with heptane (Companion, RediSep column 330 g, run duration 30.0 min, detection wavelength 254 nm, flow rate: 100 ml/min). The product is obtained as oil (880 mg, 5.879 mmol) in 28% yield.

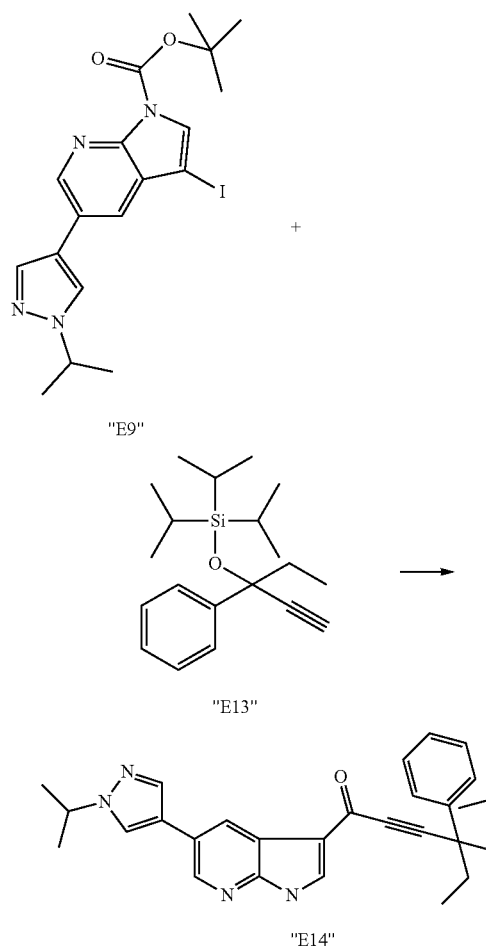

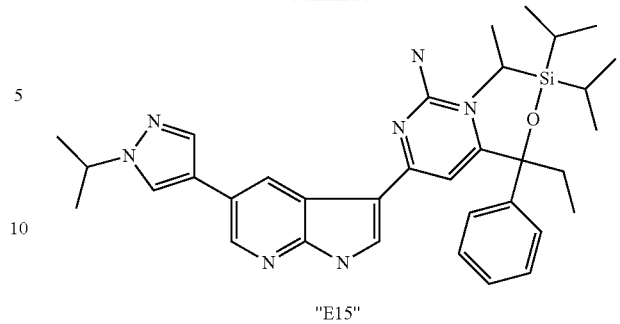

"E14" (280 mg, 0.492 mmol), guanidinium carbonate (140 mg, 0.777 mmol) and potassium carbonate (350 mg, 2.532 mmol) are suspended in ethylene glucol monomethyl ether (4 ml) and heated at 120° C. for 3 days. The reaction mixture is extracted 3 times with ethyl acetate and water. The organic phases are combined, dried over sodium sulfate and evaporated, giving "E15" (24 mg, 0.039 mmol) in 8% yield. "E15" is reacted further without purification.

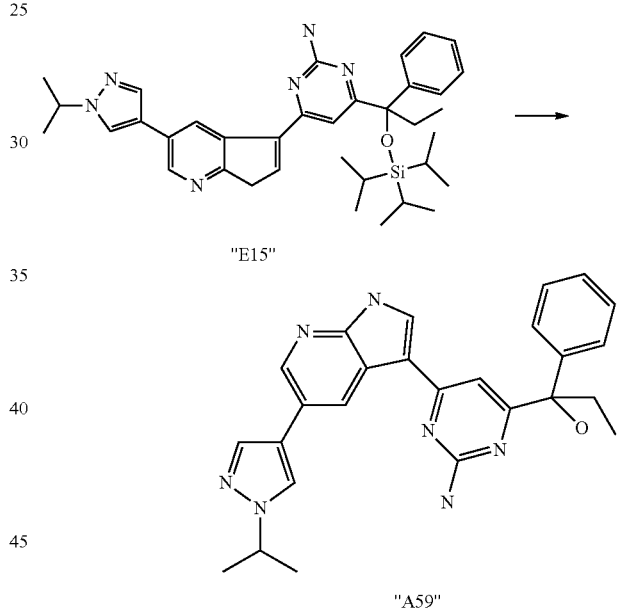

The starting materials are combined in the following sequence: the solids caesium carbonate (0.900 g, 2.762 mmol), CuI (5 mg), Pd(OAc)$_2$ (13 mg), Mo(CO)$_6$, (0.440 g, 1.667 mmol) followed by "E9" (500 mg, 1.105 mmol) dissolved in acetonitrile (2.5 ml) and "E13" (525 mg, 1.658 mmol) dissolved in toluene (2.5 ml), as the final starting material P(tert-Bu)$_3$ (140 µl, 0.551 mmol). The mixture is stirred at 80° C. for 10 min.

The reaction mixture was evaporated in a rotary evaporator below 30° C. and chromatographed (RediSep column: 40 g of silica, detection wavelength (red): 254 nm, flow rate: 40 ml/min, conditioning volume: 240.0 ml, run time 32.0 min, eluent A: L1 pet ether; eluent B: B1 ethyl acetate). The fractions containing the product are evaporated below 30° C., giving "E14" as yellow oil (280 mg, 0.391 mmol) in 35% yield.

TBAF (0.2 ml, 0.2 mmol as 1 M soln. in THF) is added to a solution of "E15" (24 mg, 0.039 mmol) in THF (0.3 ml), and the mixture is stirred at room temperature for 18 h.

The reaction mixture is evaporated in a Rotavapor. The residue is dissolved in 20 ml of ethyl acetate, and the organic phase is extracted 3 times with 1N sodium hydroxide solution. The organic phases are combined, dried using sodium sulfate and evaporated. The product is purified by means of preparative HPLC, giving "A59" as solid (15.2 mg, 85%).

EXAMPLE 5-16

Carrying out the process in accordance with Example 1, but with 2-chloromethyltetrahydrofuran as "E1a", gives the compound 4-ethyl-6-{5-[1-(tetrahydrofuran-2-ylmethyl)-1H-pyrazol-4-yl]-1H-pyrrolo[2,3-b]pyridin-3-yl}-pyrimidin-2-ylamine ("A2"), ESI [M+H]$^+$=390.

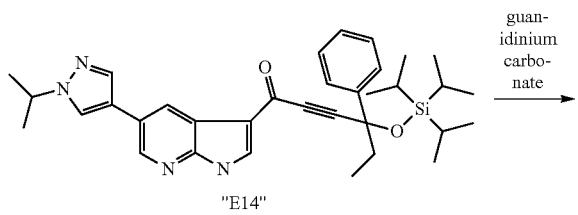

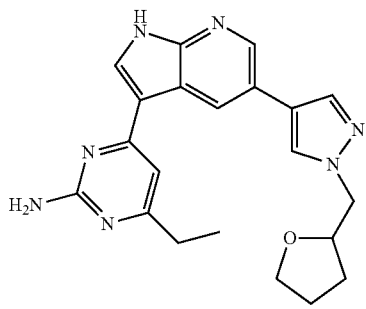

"A2"

Carrying out the process in accordance with Example 1, but with 2-chloroethylmethylamine as "E1a", gives the compound 4-ethyl-6-{5-[1-(2-methylaminoethyl)-1H-pyrazol-4-yl]-1H-pyrrolo[2,3-b]pyridin-3-yl}pyrimidin-2-yl, ("A3"), ESI [M+H]$^+$=363.

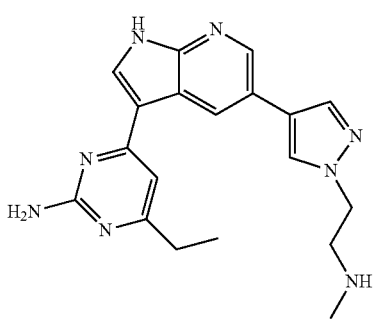

"A3"

Carrying out the process in accordance with Example 1, but with 2-chloropropylmethyldimethylamine as "E1a", gives the compound 4-{5-[1-(3-dimethylaminopropyl)-1H-pyrazol-4-yl]-1H-pyrrolo[2,3-b]pyridin-3-yl}-6-ethylpyrimidin-2-ylamine ("A4"), ESI [M+H]=391.

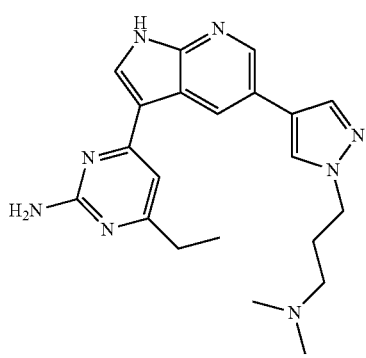

"A4"

Carrying out the process in accordance with Example 1, but with 2-chloro-1-methylpiperidine as "E1a", gives the compound 4-ethyl-6-{5-[1-(1-methylpiperidin-4-yl)-1H-pyrazol-4-yl]-1H-pyrrolo[2,3-b]pyridin-3-yl}-pyrimidin-2-ylamine ("A5"), ESI [M+H]$^+$=403.

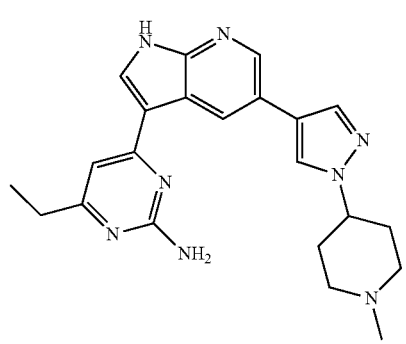

"A5"

Carrying out the process in accordance with Example 1, but with 4-chloropiperidine as "E1a", gives the compound 4-ethyl-6-[5-(1-piperidin-4-yl-1H-pyrazol-4-yl)-1H-pyrrolo[2,3-b]pyridin-3-yl]pyrimidin-2-ylamine ("A6"), ESI [M+H]=389.2.

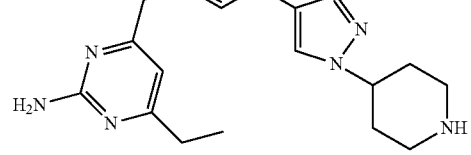

"A6"

Carrying out the process in accordance with Example 1, but with 1-(2-chloroethyl)pyrrolidine as "E1a", gives the compound 4-ethyl-6-{5-[1-(2-pyrrolidin-1-ylethyl)-1H-pyrazol-4-yl]-1H-pyrrolo[2,3-b]pyridin-3-yl}pyrimidin-2-ylamine ("A7"), ESI [M+H]=403.

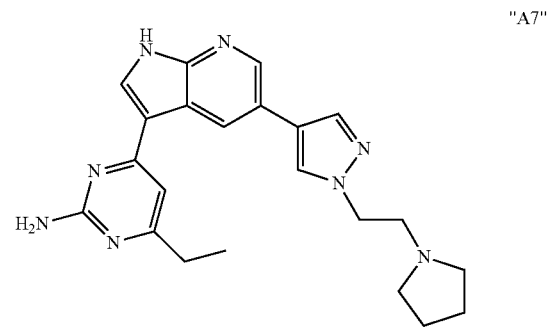 [SMILES: CCc1cc(-c2c[nH]c3ncc(-c4cnn(CCN5CCCC5)c4)cc23)nc(N)n1]

"A7"

Carrying out the process in accordance with Example 1, but with 1-(2-chloroethyl)morpholine as "E1a", gives the compound 4-ethyl-6-{5-[1-(2-morpholin-4-ylethyl)-1H-pyrazol-4-yl]-1H-pyrrolo[2,3-b]pyridin-3-yl}pyrimidin-2-ylamine ("A8"), ESI 418.

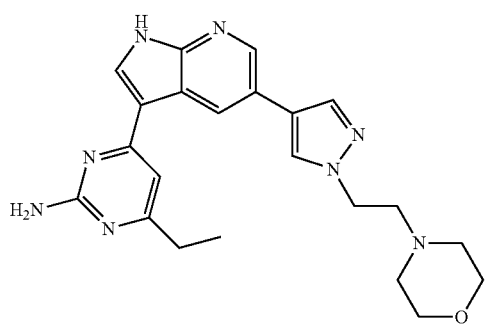
"A8"

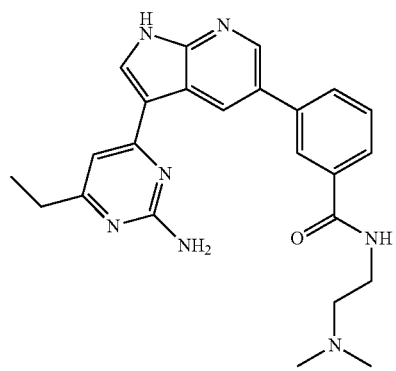
"A11"

Carrying out the process in accordance with Example 1, but with 3-chloromethylpyrrolidine as "E1a", gives the compound 4-ethyl-6-[5-(1-pyrrolidin-3-yl 1H-pyrazol-4-yl)-1H-pyrrolo[2,3-b]pyridin-3-yl]pyrimidin-2-ylamine ("A9"), ESI [M+H]$^+$=389.3.

Carrying out the process in accordance with Example 1, but with 4-(4,4,5,5-tetramethyl-1,3,2-dioxaborolan-2-yl)-1H-imidazole as "E1" and 2-chloromethyltetrahydrofuran as "E1a", gives the compound 4-ethyl-6-{5-[1-(tetrahydrofuran-2-ylmethyl)-1H-imidazol-4-yl]-1H-pyrrolo[2,3-b]pyridin-3-yl}pyrimidin-2-ylamine (A"24").

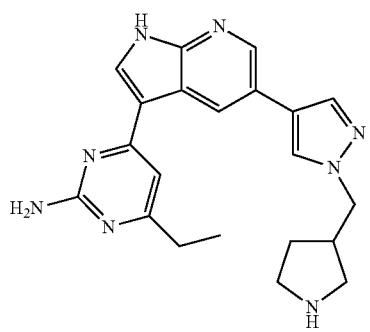
"A9"

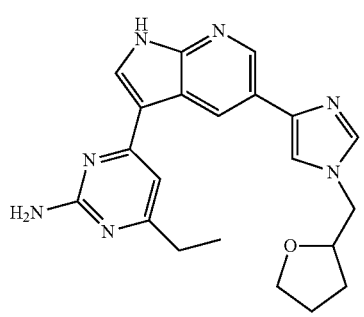
"A24"

Carrying out the process in accordance with Example 1, but with pyridine-4-boronic acid and as "E1" and 1-chloropiperazine as "E1a", gives the compound 4-ethyl-6-[5-(6-piperazin-1-ylpyridin-3-yl)-1H-pyrrolo[2,3-b]pyridin-3-yl]pyrimidin-2-ylamine ("A10"), ESI [M+H]$^+$=401.2.

Formula A25 can be prepared as follows:

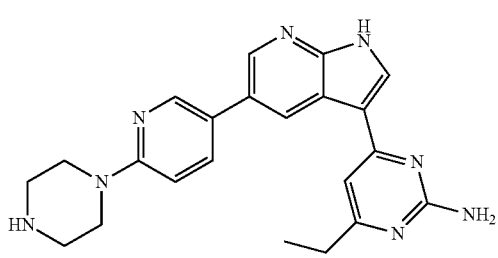
"A10"

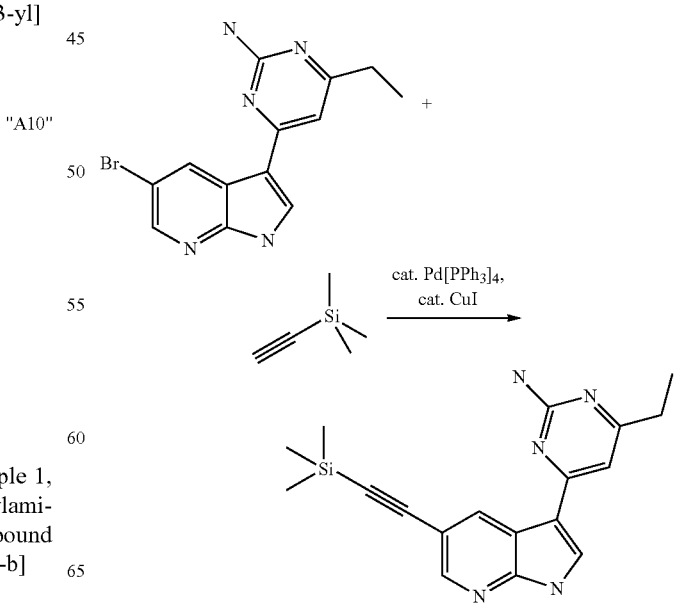

Carrying out the process in accordance with Example 1, but with toluene-4-boronic acid as "E1" and (2-dimethylaminoethyl)carbamoyl chloride as "E1a", gives the compound 3-[3-(2-amino-6-ethylpyrimidin-4-yl)-1H-pyrrolo-[2,3-b]pyridin-5-yl]-N-(2-dimethylaminoethyl)benzamide ("A11"), ESI 430.

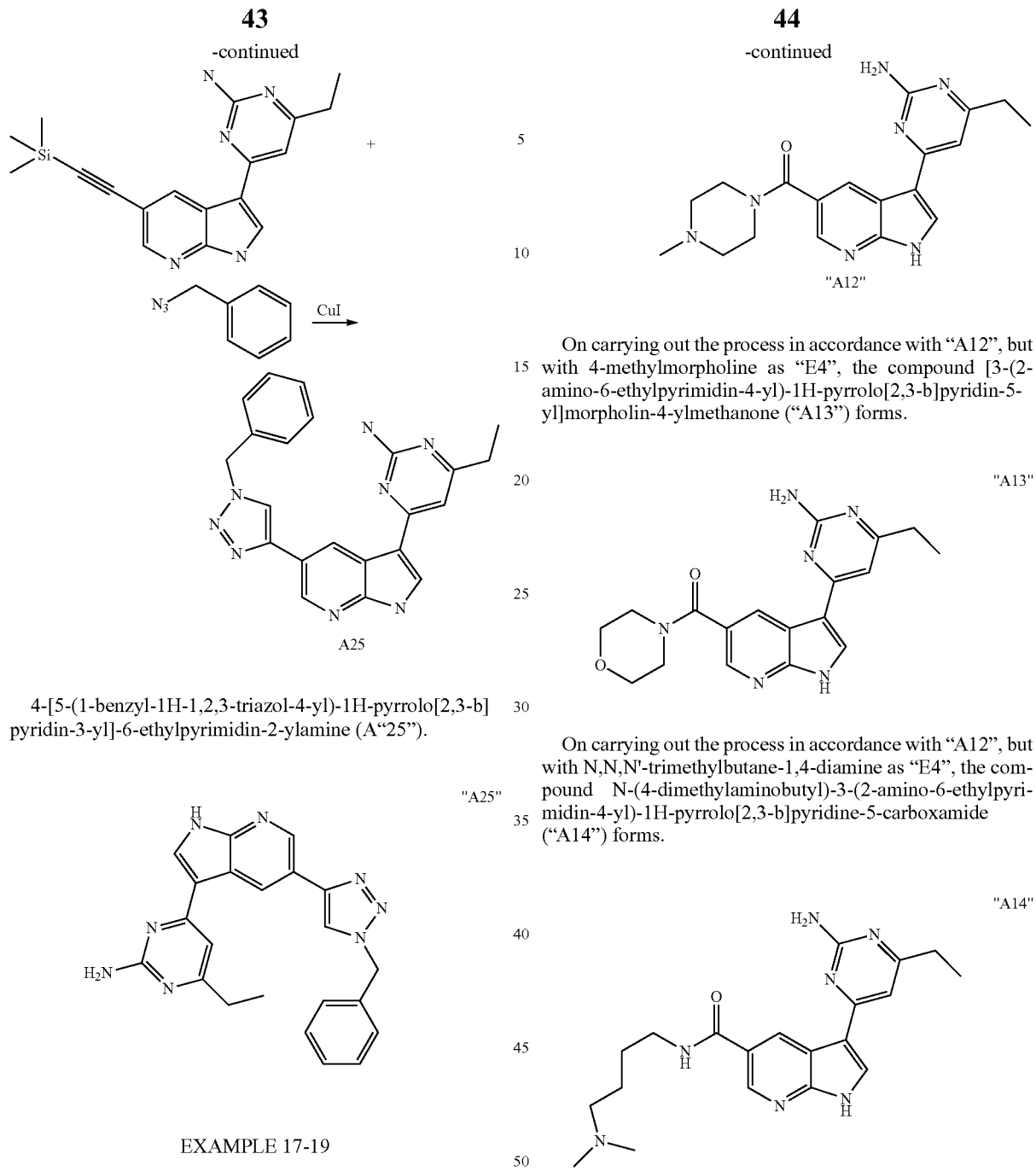

4-[5-(1-benzyl-1H-1,2,3-triazol-4-yl)-1H-pyrrolo[2,3-b]pyridin-3-yl]-6-ethylpyrimidin-2-ylamine (A"25").

EXAMPLE 17-19

The preparation of [3-(2-amino-6-ethylpyrimidin-4-yl)-1H-pyrrolo[2,3-b]pyridin-5-yl]-(4-methylpiperazin-1-yl)methanone ("A12") is carried out analogously to the following scheme by carrying out the 3rd step from Example 1 as follows:

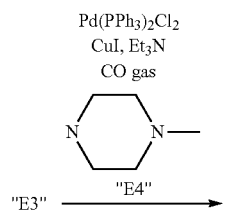

On carrying out the process in accordance with "A12", but with 4-methylmorpholine as "E4", the compound [3-(2-amino-6-ethylpyrimidin-4-yl)-1H-pyrrolo[2,3-b]pyridin-5-yl]morpholin-4-ylmethanone ("A13") forms.

On carrying out the process in accordance with "A12", but with N,N,N'-trimethylbutane-1,4-diamine as "E4", the compound N-(4-dimethylaminobutyl)-3-(2-amino-6-ethylpyrimidin-4-yl)-1H-pyrrolo[2,3-b]pyridine-5-carboxamide ("A14") forms.

EXAMPLE 20-24

The preparation of 4-[5-(2-dimethylaminoethoxy)-1H-pyrrolo[2,3-b]pyridin-3-yl]-6-ethylpyrimidin-2-ylamine ("A15") is carried out analogously to the following scheme, where K+ is a potassium salt.

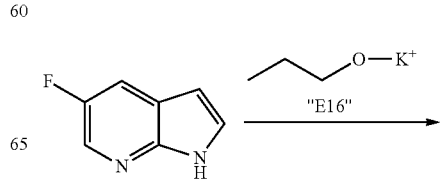

-continued

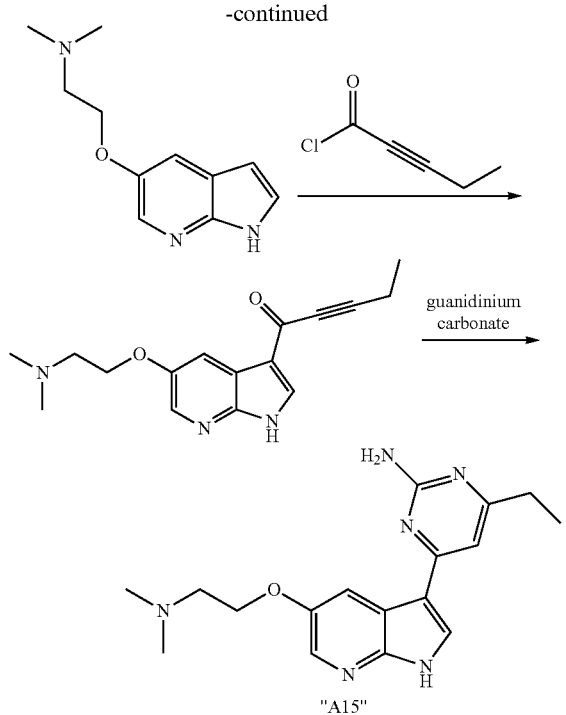

"A15"

On carrying out the process in accordance with "A15", but with 4-methoxymethylpiperidine as "E16", the compound 4-ethyl-6-[5-(piperidin-4-ylmethoxy)-1H-pyrrolo[2,3-b]pyridin-3-yl]pyrimidin-2-ylamine ("A16") forms.

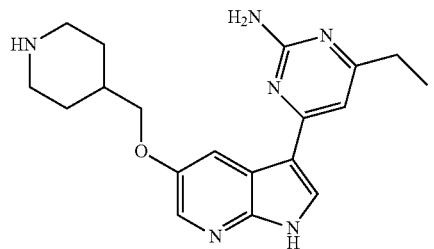

"A16"

The preparation of 4[3-(2-amino-6-ethylpyrimidin-4-yl)-1H-pyrrolo[2,3-b]-pyridin-5-yl]piperidin-4-ylmethylamine ("A17") is carried out analogously to the following scheme:

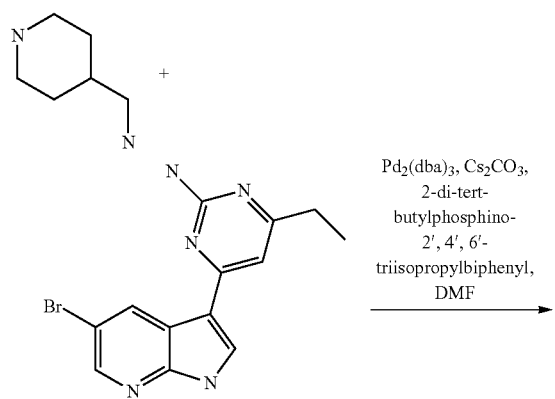

-continued

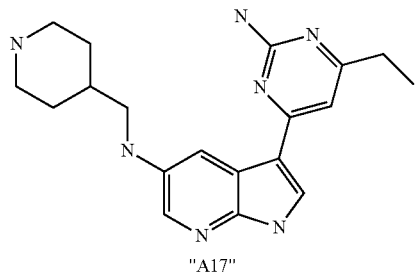

"A17"

On carrying out the process in accordance with "A17", but with N,N'-dimethylbutane-1,4-diamine as "E16", the compound N-[3-(2-amino-6-ethylpyrimidin-4-yl)-1H-pyrrolo[2,3-b]pyridin-5-yl]-N'-methylbutane-1,4-diamine ("A18") forms.

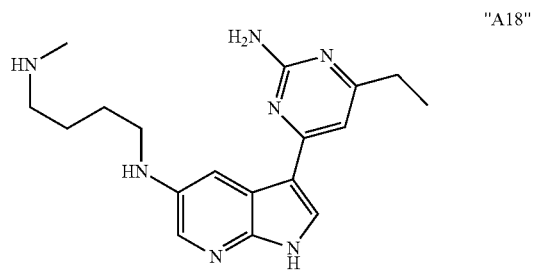 [SMILES: CCc1cc(-c2c[nH]c3ncc(NCCCCNC)cc23)nc(N)n1]

"A18"

On carrying out the process in accordance with "A15", but with N,N'-trimethylbutane-1,4-diamine as "E15", the compound N-[3-(2-amino-6-ethylpyrimidin-4-yl)-1H-pyrrolo[2,3-b]pyridin-5-yl]-N',N'-dimethylbutane-1,4-diamine ("A19") forms.

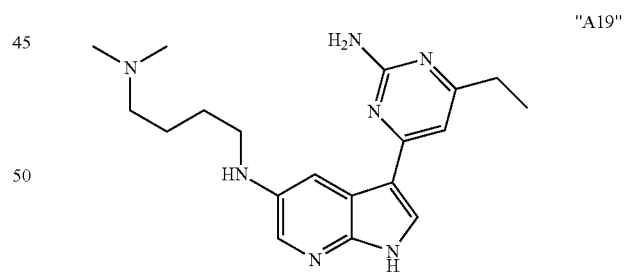

"A19"

EXAMPLE 25-32

The preparation of 4-(3-aminopropyl)-6-{5-[1-(2-pyrrolidin-1-ylethyl)-1H-pyrazol-4-yl]-1H-pyrrolo[2,3-b]pyridin-3-yl}pyrimidin-2-ylamine ("A20") is carried out analogously to the following scheme:

The preparation is carried out in accordance with the experimental procedure as described in WO2008/155000.

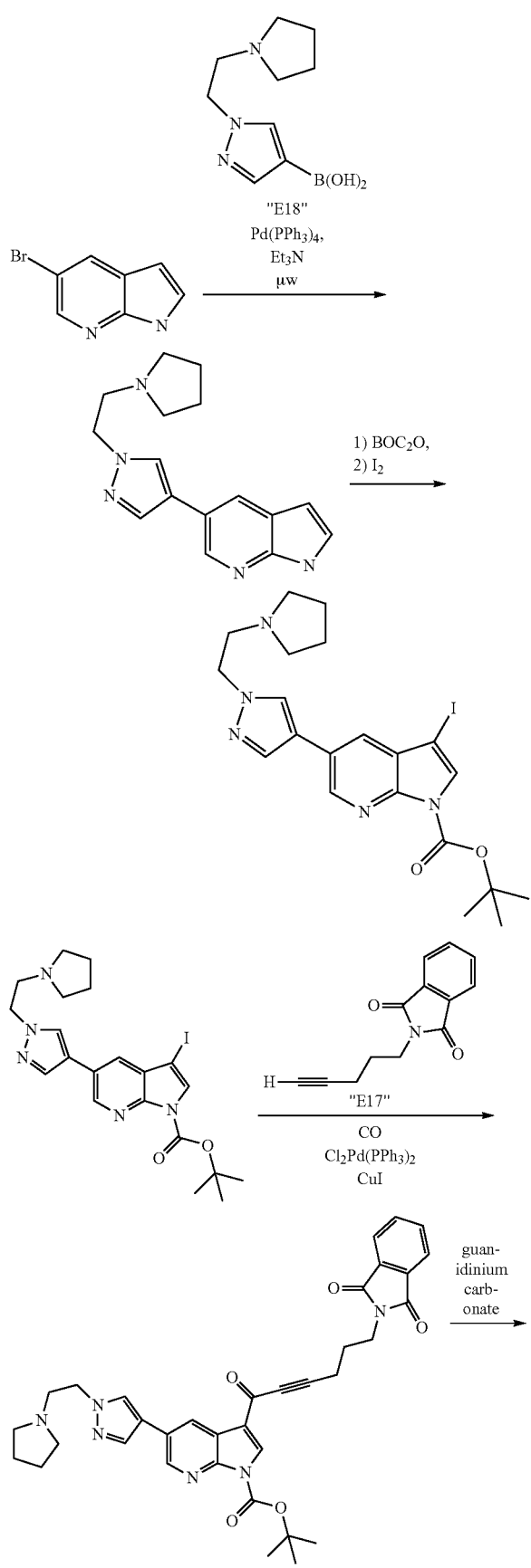

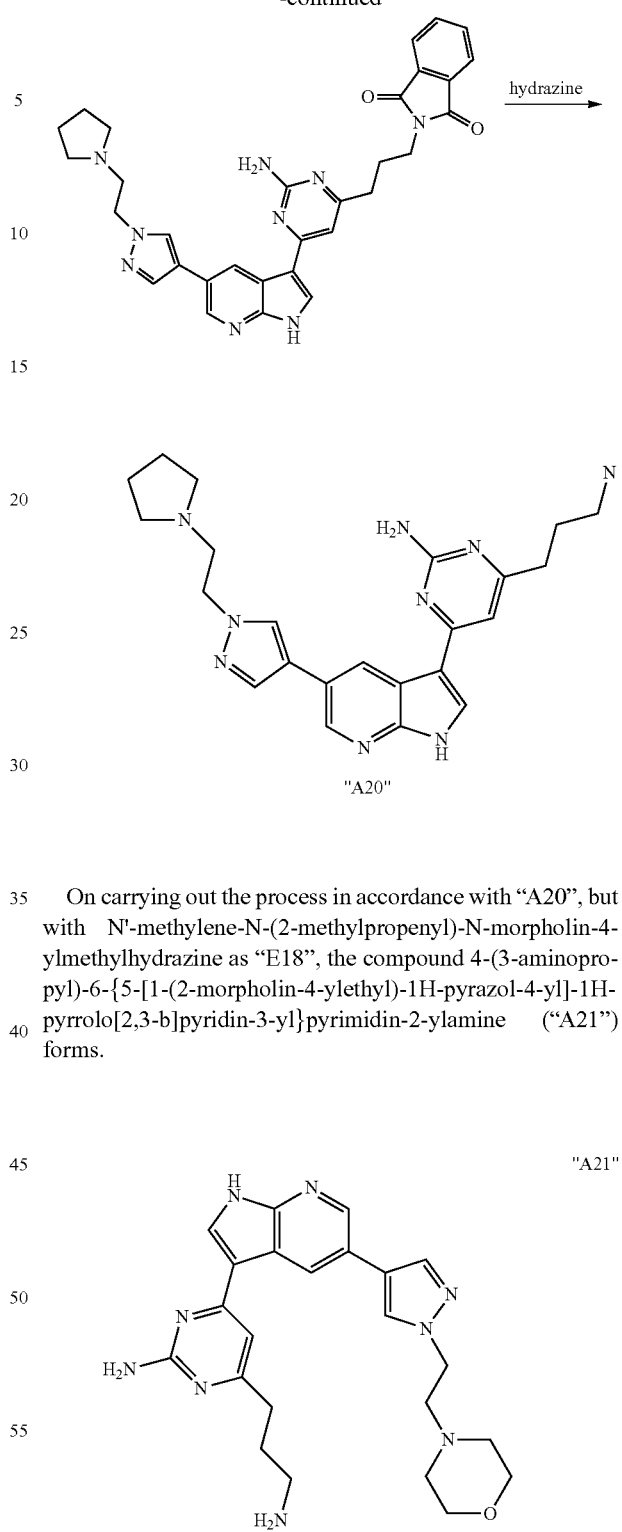

On carrying out the process in accordance with "A20", but with N'-methylene-N-(2-methylpropenyl)-N-morpholin-4-ylmethylhydrazine as "E18", the compound 4-(3-aminopropyl)-6-{5-[1-(2-morpholin-4-ylethyl)-1H-pyrazol-4-yl]-1H-pyrrolo[2,3-b]pyridin-3-yl}pyrimidin-2-ylamine ("A21") forms.

On carrying out the process in accordance with "A20", but with 4-prop-2-ynylmorpholine as "E7", the compound 4-morpholin-4-ylmethyl-6-{5-[1-(2-pyrrolidin-1-ylethyl)-1H-pyrazol-4-yl]-1H-pyrrolo[2,3-b]pyridin-3-yl}pyrimidin-2-ylamine ("A22") forms.

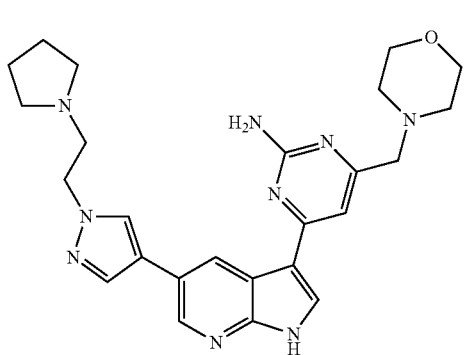

"A22"

On carrying out the process in accordance with "A20", but with tert-butyl 4-prop-2-ynylpiperazine-1-carboxylate as "E18", the compound 4-piperazin-1-ylmethyl-6-{5-[1-(2-pyrrolidin-1-ylethyl)-1H-pyrazol-4-yl]-1H-pyrrolo[2,3-b]-pyridin-3-yl}pyrimidin-2-ylamine ("A23") forms.

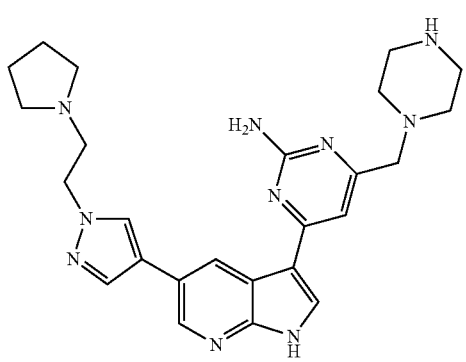

"A23"

On carrying out the process in accordance with "A20", but with methylprop-2-ynylamine as "E18", the compound 4-methylaminomethyl-6-{5-[1-(2-pyrrolidin-1-ylethyl)-1H-pyrazol-4-yl]-1H-pyrrolo[2,3-b]pyridin-3-yl}pyrimidin-2-ylamine ("A56") forms.

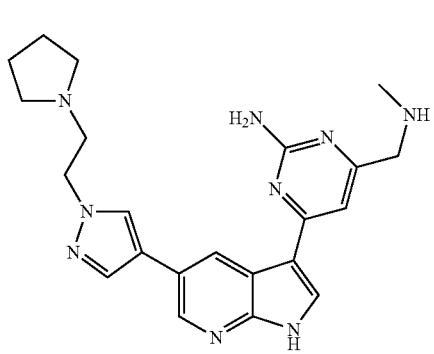

"A56"

On carrying out the process in accordance with "A20", but with methylpent-4-ynylamine as "E18", the compound 4-(3-methylaminopropyl)-6-{5-[1-(2-pyrrolidin-1-ylethyl)-1H-pyrazol-4-yl]-1H-pyrrolo[2,3-b]pyridin-3-yl}pyrimidin-2-ylamine ("A57") forms.

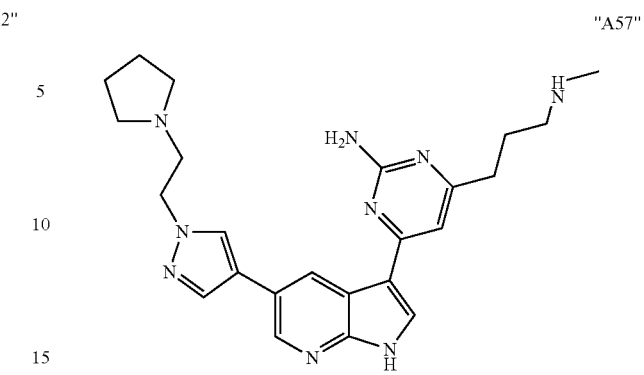

"A57"

On carrying out the process in accordance with "A20", but with dimethylpent-4-ynylamine as "E18", the compound 4-(3-dimethylaminopropyl)-6-{5-[1-(2-pyrrolidin-1-yl-ethyl)-1H-pyrazol-4-yl]-1H-pyrrolo[2,3-b]pyridin-3-yl}-pyrimidin-2-ylamine ("A26") forms

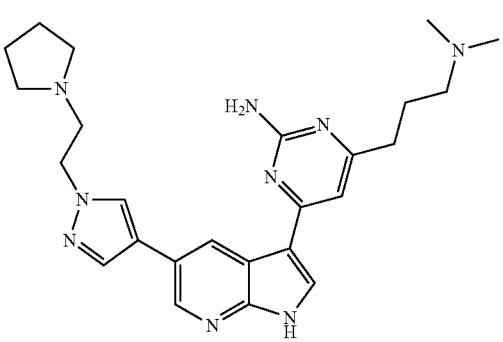

"A26"

4-Ethyl-6-[5-(5-phenyloxazol-2-yl)-1H-pyrrolo[2,3-b]pyridin-3-yl]pyrimidin-2-ylamine ("A27") can be prepared in accordance with the following scheme:

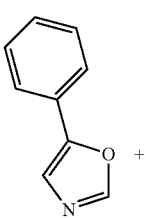

+

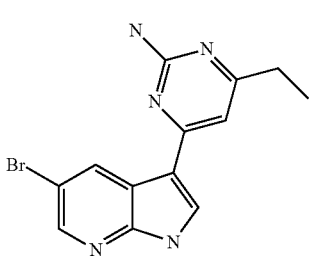

5 mol % of Pd(OAc)2
1 eq of CuI
2 eq of K2CO3
DMF, μw, 150° C.

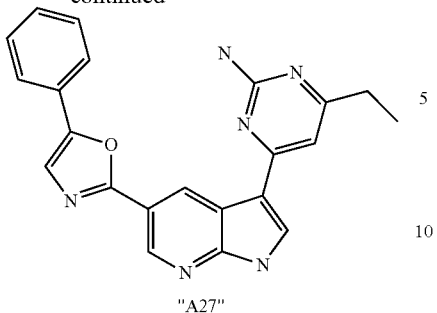

"A27"

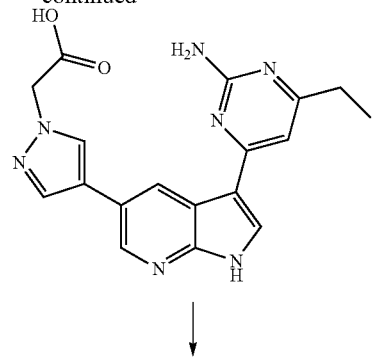

EXAMPLE 33-39

The following substances can be prepared using corresponding starting materials in accordance with Example 2 or in accordance with the following general scheme.

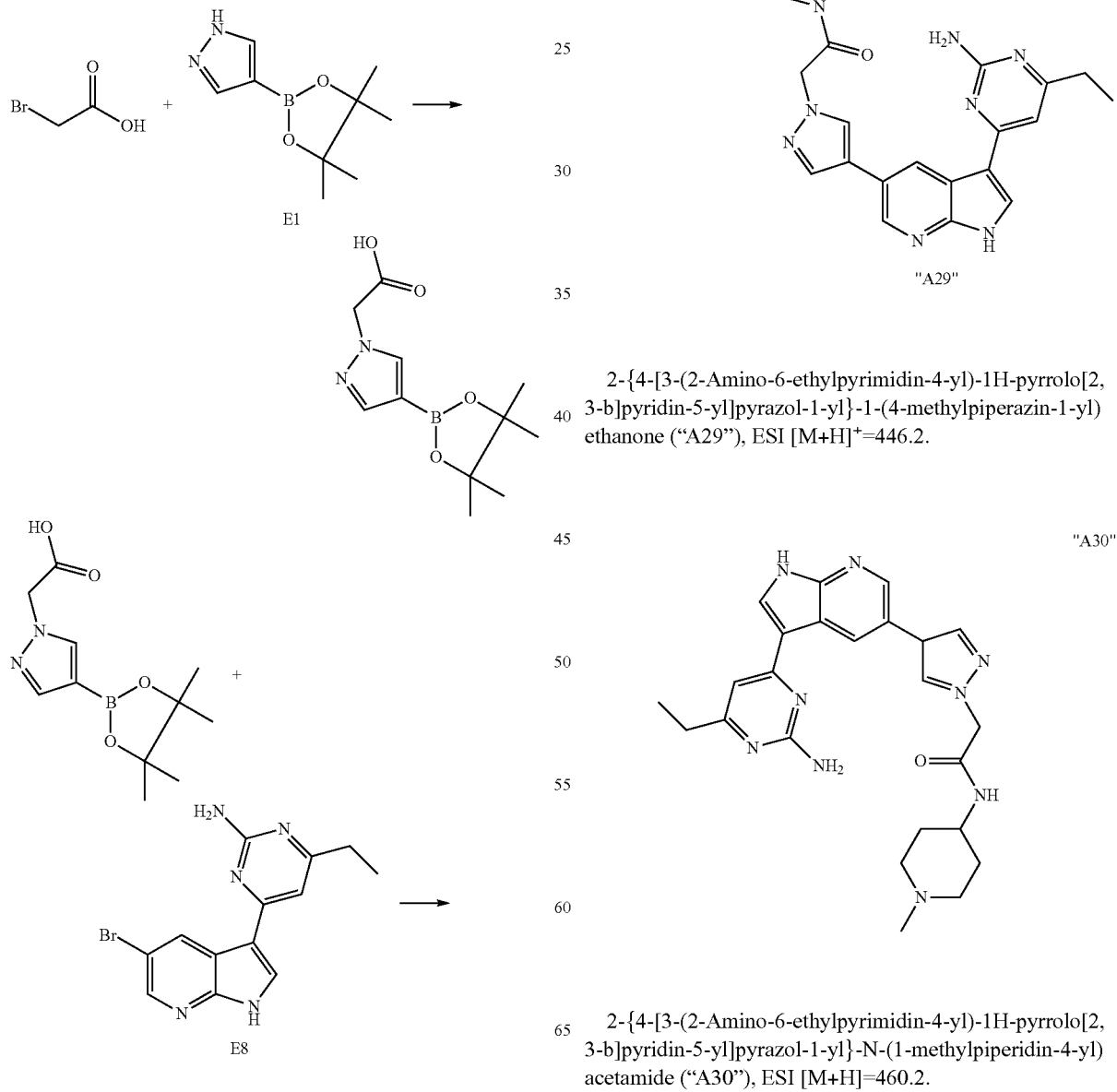

2-{4-[3-(2-Amino-6-ethylpyrimidin-4-yl)-1H-pyrrolo[2,3-b]pyridin-5-yl]pyrazol-1-yl}-1-(4-methylpiperazin-1-yl)ethanone ("A29"), ESI [M+H]⁺=446.2.

2-{4-[3-(2-Amino-6-ethylpyrimidin-4-yl)-1H-pyrrolo[2,3-b]pyridin-5-yl]pyrazol-1-yl}-N-(1-methylpiperidin-4-yl)acetamide ("A30"), ESI [M+H]=460.2.

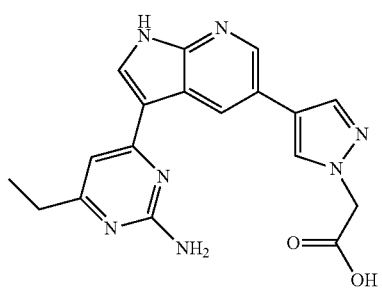

"A31"

{4-[3-(2-Amino-6-ethylpyrimidin-4-yl)-1H-pyrrolo[2,3-b]pyridin-5-yl]pyrazol-1-yl}acetylic acid ("A31"), ESI [M+H]$^+$=364.2.

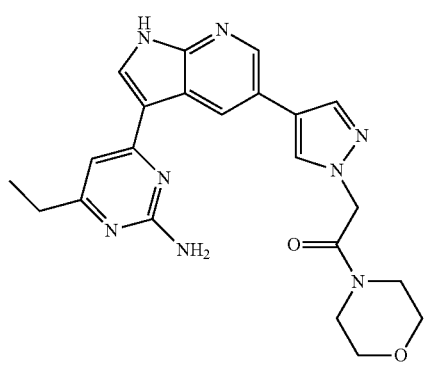

"A32"

2-{4-[3-(2-Amino-6-ethylpyrimidin-4-yl)-1H-pyrrolo[2,3-b]pyridin-5-yl]pyrazol-1-yl}-1-morpholin-4-ylethanone ("A32"), ESI [M+H]$^+$=433.2.

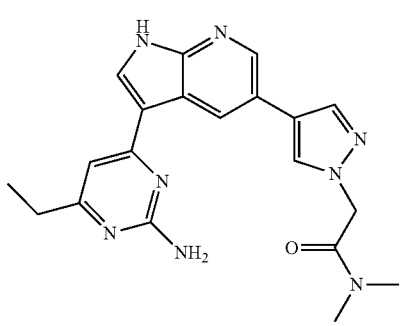

"A34"

2-{4-[3-(2-Amino-6-ethylpyrimidin-4-yl)-1H-pyrrolo[2,3-b]pyridin-5-yl]pyrazol-1-yl}-N,N-dimethylacetamide ("A34"), ESI [M+H]$^+$=391.2.

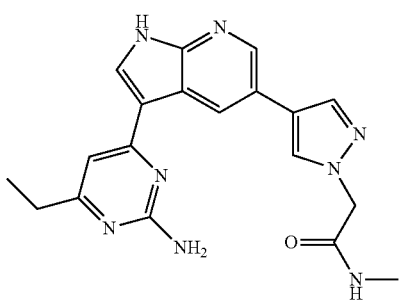

"A51"

2-{4-[3-(2-Amino-6-ethylpyrimidin-4-yl)-1H-pyrrolo[2,3-b]pyridin-5-yl]pyrazol-1-yl}-N-methylacetamide ("A51"), ESI [M+H]$^+$=377.2.

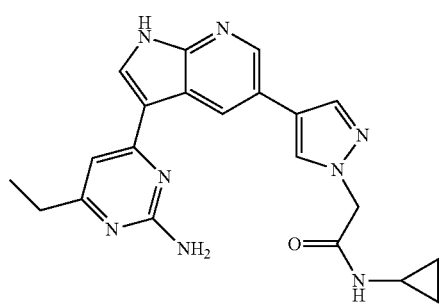

"A52"

2-{4-[3-(2-Amino-6-ethylpyrimidin-4-yl)-1H-pyrrolo[2,3-b]pyridin-5-yl]pyrazol-1-yl}-N-cyclopropylacetamide ("A52"). ESI [M+H]=403.2

1H-NMR (d6-DMSO, 500 MHz): δ=0.51 (m, 2H), 0.69 (m, 2H), 1.35 (t, J=7 Hz, 3H), 2.59-2.73 (m, 3H), 4.85 (s, 2H), 7.45 (s, 1H), 8.25 (s, 1H), 8.41 (s, 1H), 8.65 (d, J=1 Hz, 1H), 8.95 (d, J=1 Hz, 1H), 9.25 (s, 1H) ppm

EXAMPLE 40-59

The following substances can be prepared using corresponding starting materials in accordance with the following general scheme, Examples 1 or 3, where OTIPS stands for O trisisopropyl silyl, which is a protecting group, and TBAF denotes tert-butyl amonium fluoride.

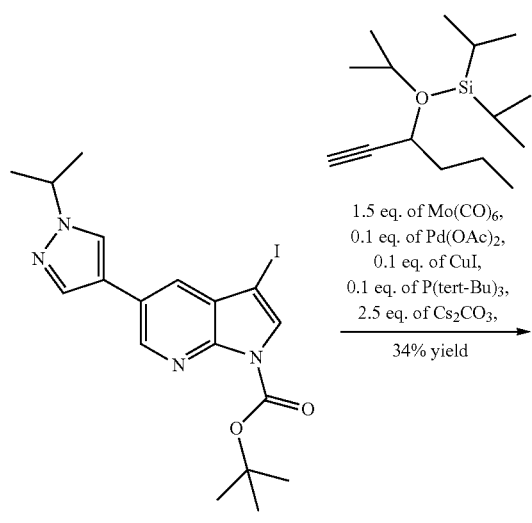

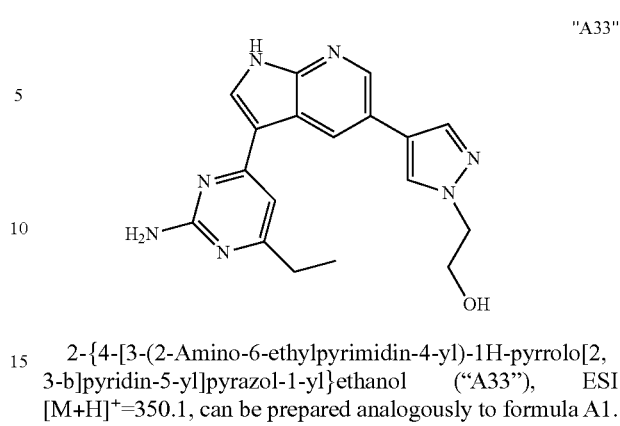

2-{4-[3-(2-Amino-6-ethylpyrimidin-4-yl)-1H-pyrrolo[2,3-b]pyridin-5-yl]pyrazol-1-yl}ethanol ("A33"), ESI [M+H]$^+$=350.1, can be prepared analogously to formula A1.

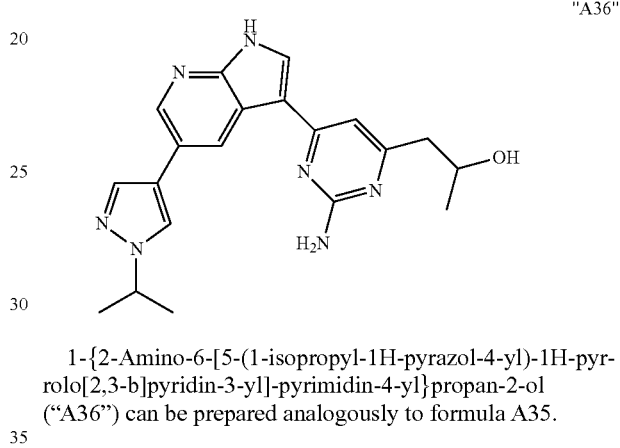

1-{2-Amino-6-[5-(1-isopropyl-1H-pyrazol-4-yl)-1H-pyrrolo[2,3-b]pyridin-3-yl]-pyrimidin-4-yl}propan-2-ol ("A36") can be prepared analogously to formula A35.

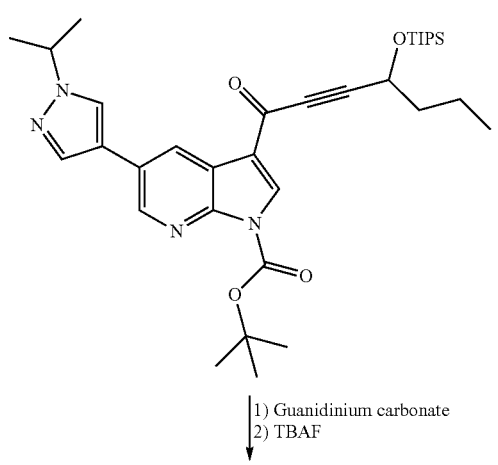

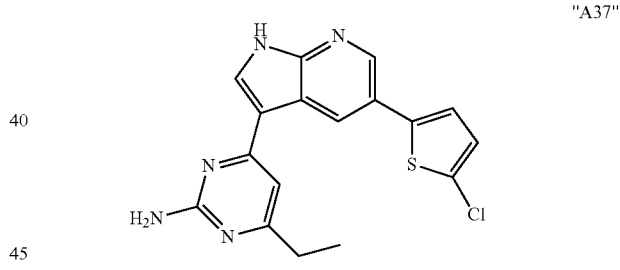

4-[5-(5-Chlorothiophen-2-yl)-1H-pyrrolo[2,3-b]pyridin-3-yl]-6-ethylpyrimidin-2-ylamine ("A37") can be prepared analogously to formula A1.

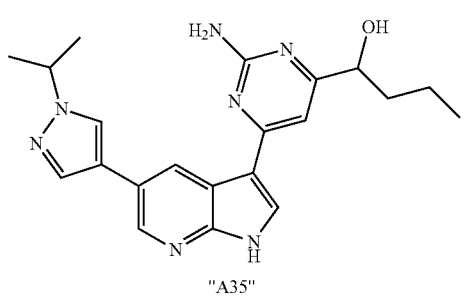

1-{2-Amino-6-[5-(1-isopropyl-1H-pyrazol-4-yl)-1H-pyrrolo[2,3-b]pyridin-3-yl]-pyrimidin-4-yl}butan-1-ol ("A35"), ESI [M+H]J=392.1, 1H-NMR (d6-DMSO, 400 MHz): δ=0.74 (t, J=7.3 Hz, 3H), 1.26 (m, 2H), 1.32 (d, J=6.6 Hz, 6H), 1.41 (m, 1H), 1.55 (m, 1H), 4.15 (q, J=3.9 Hz, 1H), 4.37 (m, 1H), 5.05 (s, 1H), 6.39 (s, 2H), 6.97 (s, 1H), 7.89 (s, 1H), 8.13 (m, 2H), 8.41 (d, J=1.9 Hz, 1H), 8.87 (d, J=1.8 Hz, 1H), 11.93 (s, 1H) ppm.

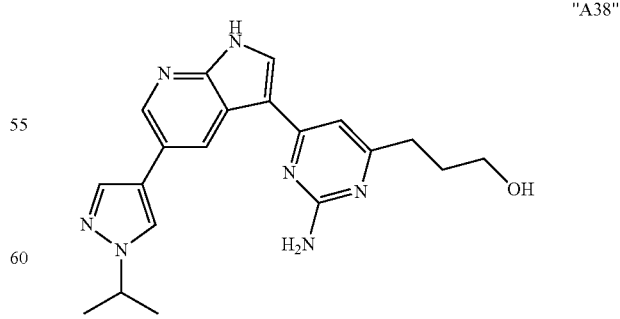

3-{2-Amino-6-[5-(1-isopropyl-1H-pyrazol-4-yl)-1H-pyrrolo[2,3-b]pyridin-3-yl]-pyrimidin-4-yl}propan-1-ol ("A38"), ESI [M+H]$^+$=378, can be prepared analogously to formula A35.

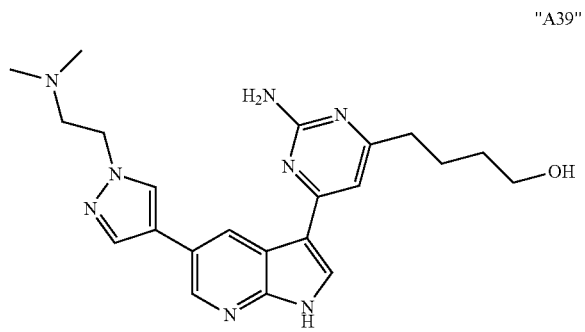 [SMILES: CN(C)CCn1cc(-c2cnc3[nH]cc(-c4cc(CCCCO)nc(N)n4)c3c2)cn1]

4-(2-Amino-6-{5-[1-(2-dimethylaminoethyl)-1H-pyrazol-4-yl]-1H-pyrrolo-[2,3-b]pyridin-3-yl}pyrimidin-4-yl)butan-1-ol ("A39"), ESI [M+H]=421.2, can be prepared analogously to formula A35.

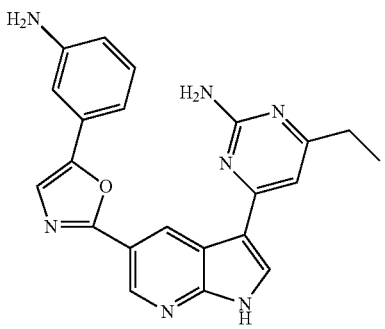

4-{5-[5-(3-Aminophenyl)oxazol-2-yl]-1H-pyrrolo[2,3-b]pyridin-3-yl}-6-ethylpyrimidin-2-ylamine ("A42"), ESI [M+H]⁺=398.2, can be prepared analogously to formula A27.

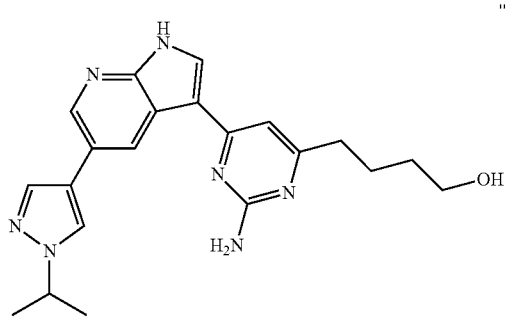

4-{2-Amino-6-[5-(1-isopropyl-1H-pyrazol-4-yl)-1H-pyrrolo[2,3-b]pyridin-3-yl]-pyrimidin-4-yl}butan-1-ol ("A40"), ESI [M+H]⁺=392, can be prepared analogously to formula A35.

4-[5-(1-Isopropyl-1H-pyrazol-4-yl)-1H-pyrrolo[2,3-b]pyridin-3-yl]-6-[2-(4-methylpiperazin-1-yl)ethyl]pyrimidin-2-ylamine ("A43"), ESI [M+H]⁺=446.2, can be prepared analogously to formula A35.

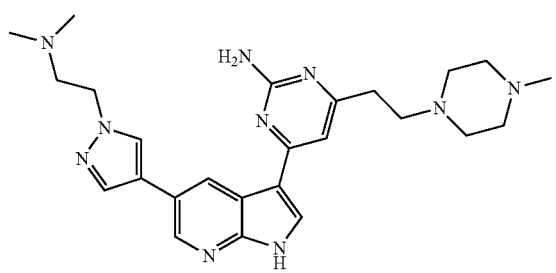

4-{5-[1-(2-Dimethylaminoethyl)-1H-pyrazol-4-yl]-1H-pyrrolo[2,3-b]pyridin-3-yl}-6-[2-(4-methylpiperazin-1-yl)ethyl]pyrimidin-2-ylamine ("A41"), ESI [M+H]=475.2, can be prepared analogously to formula A35.

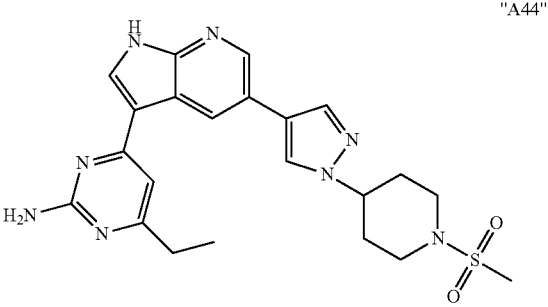 [SMILES: CCc1cc(-c2c[nH]c3ncc(-c4cnn(C5CCN(S(C)(=O)=O)CC5)c4)cc23)nc(N)n1]

4-Ethyl-6-{5-[1-(1-methanesulfonylpiperidin-4-yl)-1H-pyrazol-4-yl]-1H-pyrrolo[2,3-b]pyridin-3-yl}pyrimidin-2-ylamine ("A44"), ESI [M+H]⁺=467.1, can be prepared analogously to formula A1.

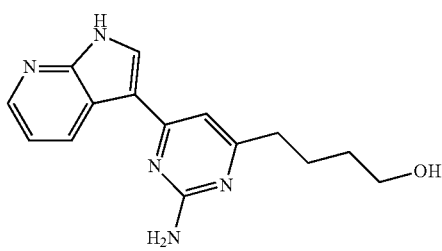

"A45"

4-[2-Amino-6-(1H-pyrrolo[2,3-b]pyridin-3-yl)pyrimidin-4-yl]butan-1-ol ("A45"), ESI [M+H]$^+$=284, can be prepared analogously to formula A35.

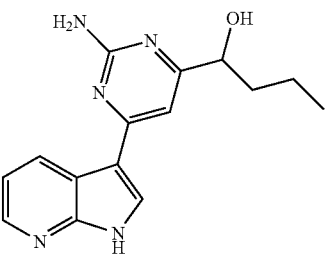

"A48"

1-[2-Amino-6-(1H-pyrrolo[2,3-b]pyridin-3-yl)pyrimidin-4-yl]butan-1-ol ("A48"), ESI [M+H]$^+$=409, can be prepared analogously to formula A35.

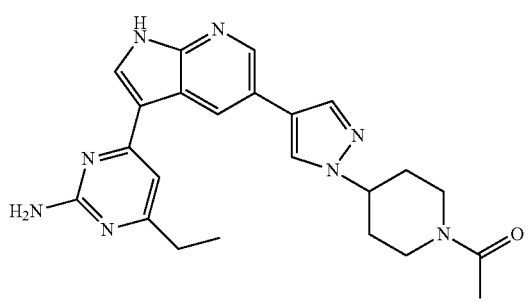

"A46"

1-(4-{4-[3-(2-Amino-6-ethylpyrimidin-4-yl)-1H-pyrrolo[2,3-b]pyridin-5-yl]-pyrazol-1-yl}piperidin-1-yl)ethanone ("A46"), ESI [M+H]=431, can be prepared analogously to formula A1.

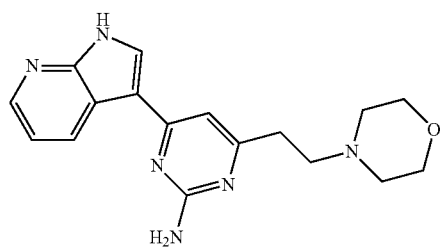

"A49"

4-(2-Morpholin-4-ylethyl)-6-(1H-pyrrolo[2,3-b]pyridin-3-yl)pyrimidin-2-ylamine ("A49"), ESI [M+H]=325, can be prepared analogously to formula A35.

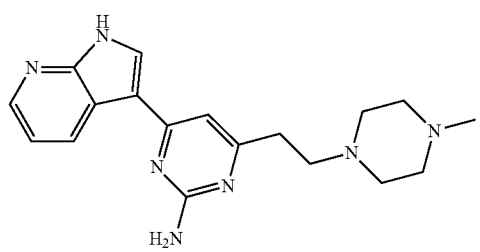

"A50"

4-[2-(4-Methylpiperazin-1-yl)ethyl]-6-(1H-pyrrolo[2,3-b]pyridin-3-yl)pyrimidin-2-ylamine ("A50"), ESI [M+H]$^+$=338.

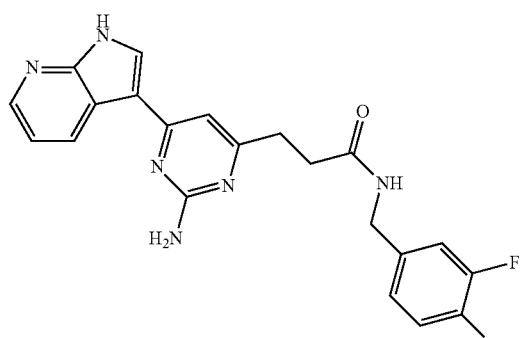

"A47"

3-[2-Amino-6-(1H-pyrrolo[2,3-b]pyridin-3-yl)pyrimidin-4-yl]-N-(3,4-difluorobenzyl)propionamide ("A47"), ESI [M+H]$^+$=409.

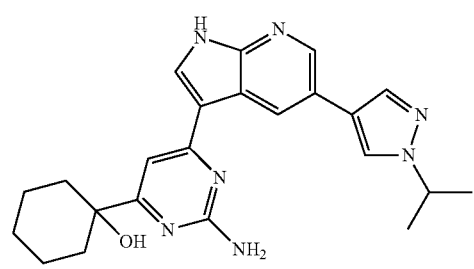

"A53"

1-{2-Amino-6-[5-(1-isopropyl-1H-pyrazol-4-yl)-1H-pyrrolo[2,3-b]pyridin-3-yl]-pyrimidin-4-yl}cyclohexanol ("A53"), ESI [M+H]$^+$=418, can be prepared analogously to formula A35.

1H-NMR (d6-DMSO, 500 MHz): δ=1.24 (m, 2H), 1.51 (m, 9H), 1.70 (m, 3H), 1.89 (m, 2H), 4.54 (m, 1H), 4.90 (s, 1H), 6.54 (s, 2H), 7.28 (s, 1H), 8.05 (s, 1H), 8.29 (d, J=18.0, 2H), 8.57 (s, 1H), 9.02 (s, 1H), 12.09 (s, 1H) ppm.

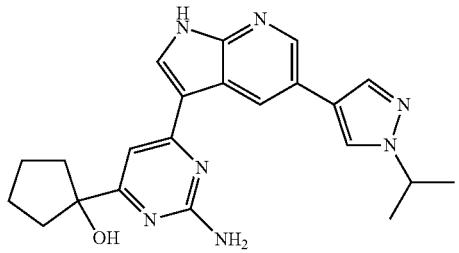

"A54"

1-{2-Amino-6-[5-(1-isopropyl-1H-pyrazol-4-yl)-1H-pyrrolo[2,3-b]pyridin-3-yl]-pyrimidin-4-yl}cyclopentanol ("A54"), ESI [M+H]$^+$=404, can be prepared analogously to formula A35.

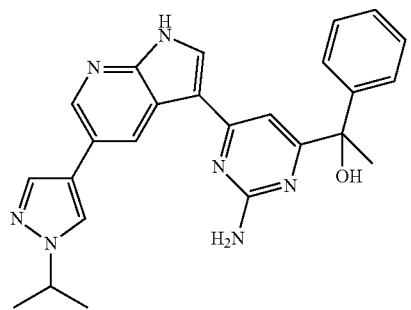

"A55"

1-{2-Amino-6-[5-(1-isopropyl-1H-pyrazol-4-yl)-1H-pyrrolo[2,3-b]pyridin-3-yl]-pyrimidin-4-yl}-1-phenylethanol ("A55"), ESI [M+H]=440.1.
1H-NMR in DMSO shift in [ppm]: 12.20 (s, 1H, NH), 9.00 (s, 1H), 8.55 (s, 1H), 8.31 (s, 2H), 8.05 (s, 1H), 7.57 (m, 2H), 7.25 (m, 3H), 7.16 (m, 1H), 6.60 (s, NH), 4.55 (h, J=8 Hz, 1H), 1.84 (s, 3H), 1.5 (d, J=8 Hz, 6H)

EXAMPLE 60-73

The following compounds can be synthesised by the person skilled in the art analogously to above synthesis schemes or Example 1-4, 17, 25, 32, or 74:

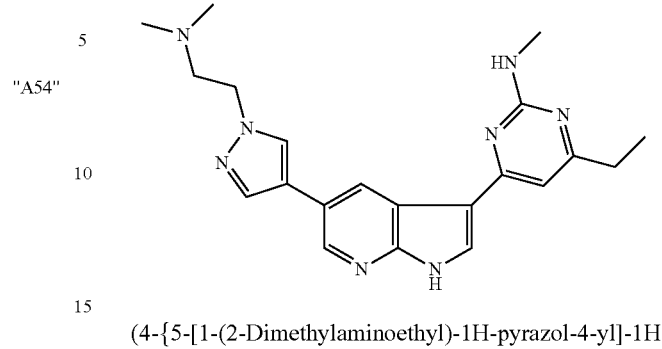

"A61"

(4-{5-[1-(2-Dimethylaminoethyl)-1H-pyrazol-4-yl]-1H-pyrrolo[2,3-b]pyridin-3-yl}-6-ethylpyrimidin-2-yl)methylamine ("A61"), ESI [M+H]+=391.3

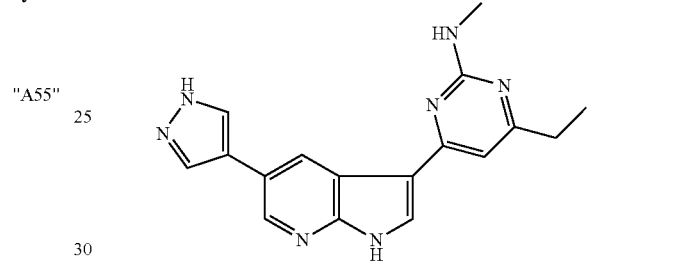

"A62"

{4-Ethyl-6-[5-(1H-pyrazol-4-yl)-1H-pyrrolo[2,3-b]pyridin-3-yl]pyrimidin-2-yl}-methylamine ("A62"), ESI [M+H]+=320.4

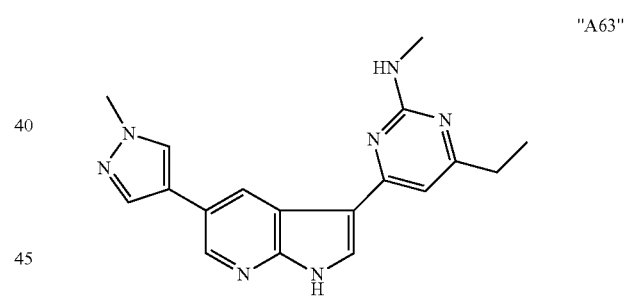

"A63"

{4-Ethyl-6-[5-(1-methyl-1H-pyrazol-4-yl)-1H-pyrrolo[2,3-b]pyridin-3-yl]-pyrimidin-2-yl}methylamine ("A63"), ESI [M+H]+=334.4

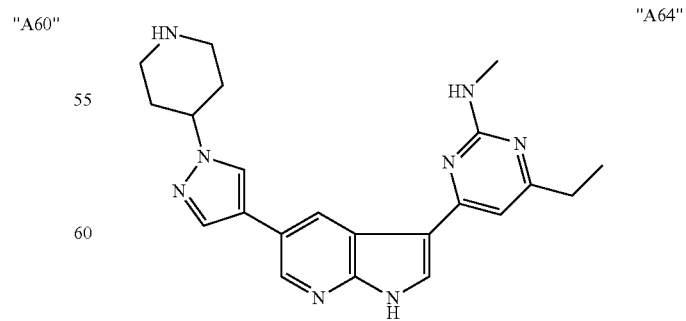

"A60"

{4-Ethyl-6-[5-(1-isopropyl-1H-pyrazol-4-yl)-1H-pyrrolo[2,3-b]pyridin-3-yl]-pyrimidin-2-yl}methylamine ("A60"), ESI [M+H]+=362.4

"A64"

{4-Ethyl-6-[5-(1-piperidin-4-yl-1H-pyrazol-4-yl)-1H-pyrrolo[2,3-b]pyridin-3-yl]pyrimidin-2-yl}methylamine ("A64"), ESI [M+H]+=403.5

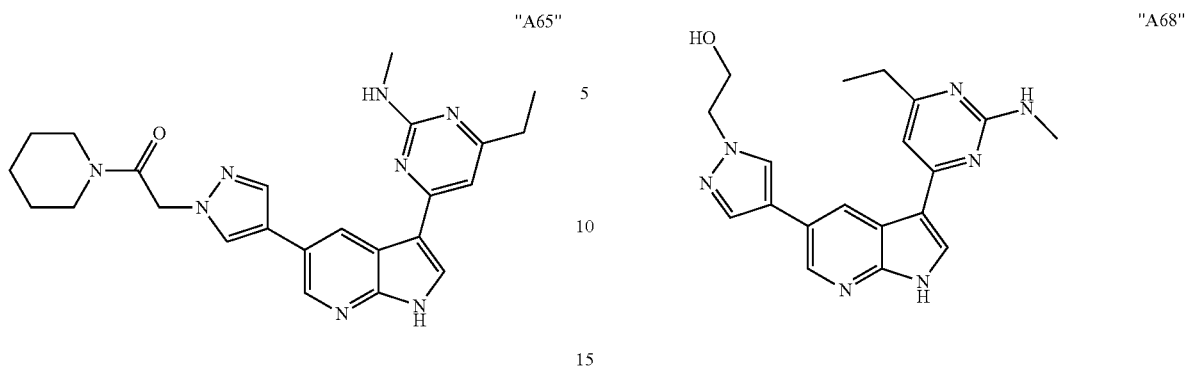

2-{4-[3-(6-Ethyl-2-methylaminopyrimidin-4-yl)-1H-pyrrolo[2,3-b]pyridin-5-yl]-pyrazol-1-yl}-1-piperidin-1-ylethanone ("A65"), ESI [M+H]+=445.2

2-{4-[3-(6-Ethyl-2-methylaminopyrimidin-4-yl)-1H-pyrrolo[2,3-b]pyridin-5-yl]-pyrazol-1-yl}ethanol ("A68"), ESI [M+H]+=364.4

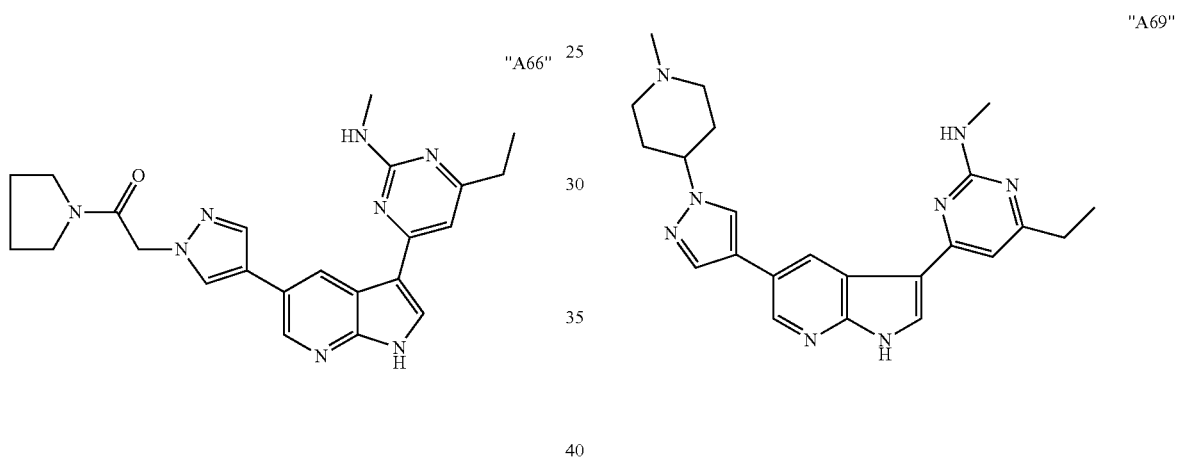

2-{4-[3-(6-Ethyl-2-methylaminopyrimidin-4-yl)-1H-pyrrolo[2,3-b]pyridin-5-yl]-pyrazol-1-yl}-1-pyrrolidin-1-ylethanone ("A66"), ESI [M+H]+=431.5

(4-Ethyl-6-{5-[1-(1-methylpiperidin-4-yl)-1H-pyrazol-4-yl]-1H-pyrrolo[2,3-b]-pyridin-3-yl}pyrimidin-2-yl)methylamine ("A69"),

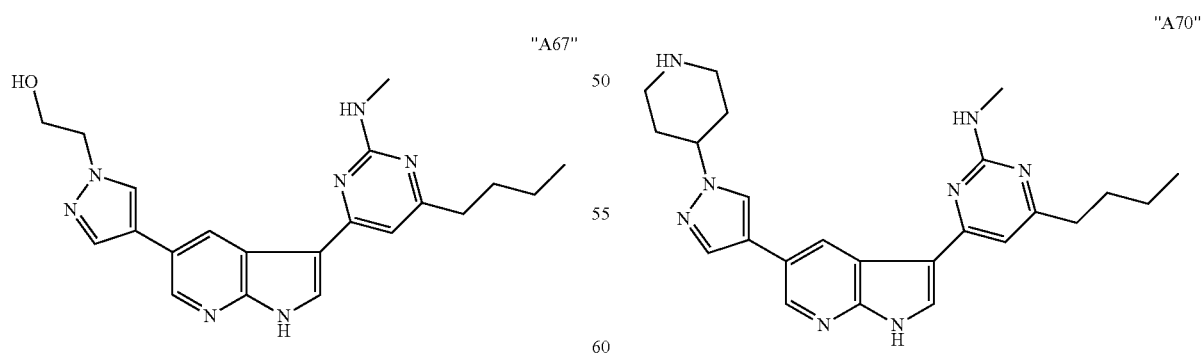

2-{4-[3-(6-Butyl-2-methylaminopyrimidin-4-yl)-1H-pyrrolo[2,3-b]pyridin-5-yl]-pyrazol-1-yl}ethanol ("A67"), ESI [M+H]+=392.4

{4-Butyl-6-[5-(1-piperidin-4-yl-1H-pyrazol-4-yl)-1H-pyrrolo[2,3-b]pyridin-3-yl]pyrimidin-2-yl}methylamine ("A70"), ESI [M+H]+=431.44

"A71"

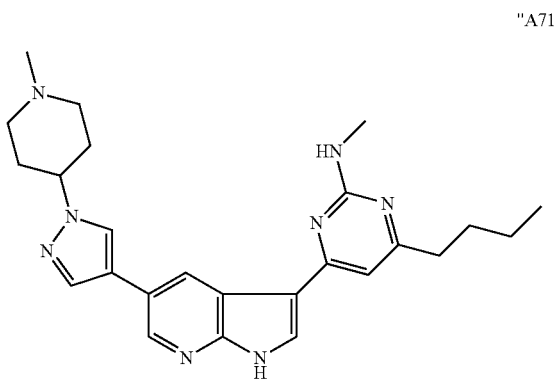

(4-Butyl-6-{5-[1-(1-methylpiperidin-4-yl)-1H-pyrazol-4-yl]-1H-pyrrolo[2,3-b]-pyridin-3-yl}pyrimidin-2-yl)methylamine ("A71"),

"A72"

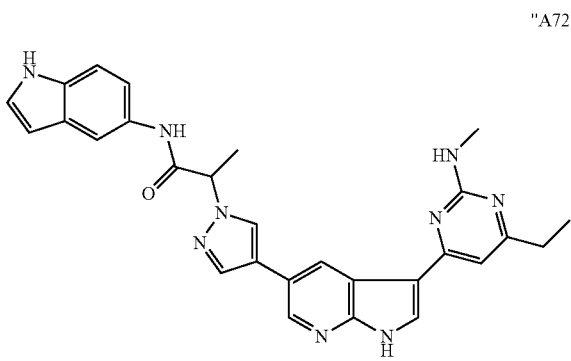

2-{4-[3-(6-Ethyl-2-methylaminopyrimidin-4-yl)-1H-pyrrolo[2,3-b]pyridin-5-yl]-pyrazol-1-yl}-N-(1H-indol-5-yl)propionamide ("A72"), ESI [M+H]+=506

"A73"

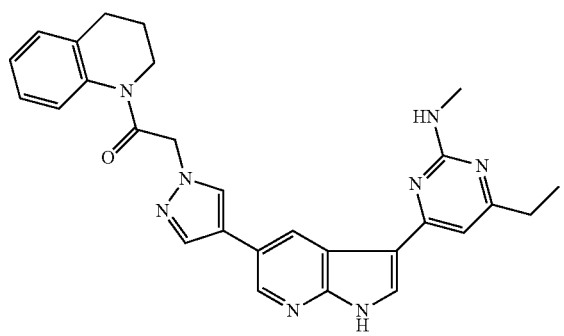

1-(3,4-Dihydro-2H-quinolin-1-yl)-2-{4-[3-(6-ethyl-2-methylaminopyrimidin-4-yl)-1H-pyrrolo[2,3-b]pyridin-5-yl]pyrazol-1-yl}ethanone ("A73"), ESI [M+H]+=493.4

EXAMPLE 74-114

The following substances can be prepared using corresponding starting materials in accordance with the following general scheme.

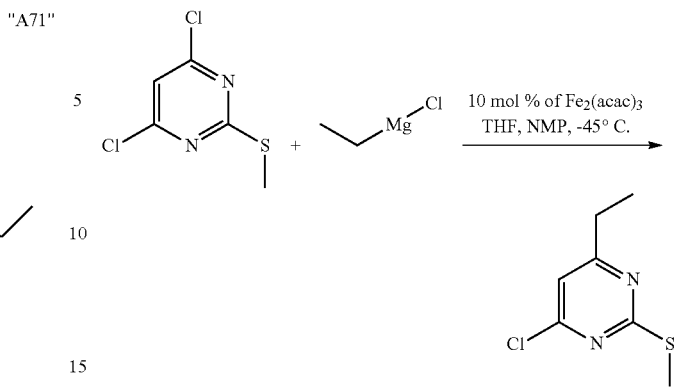

4,6-Dichloro-2-methylsulfanylpyrimidine (1.5 g, 7.7 mmol) and iron(III) acetylacetonate (272 mg, 0.7 mmol) are dissolved in THF/NMP (15 ml/1 ml), and the red reaction solution is cooled to −45° C. using a dry-ice/ethanol bath. The ethylmagnesium chloride solution (2.9 ml, 8.4 mmol, 25% in THF) is then added, and the reaction is stirred at −45° C. for 60 min. The cooling bath is removed, and the reaction is stirred further at RT. The reaction solution is acidified using 1N HCl and extracted three times with ethyl acetate. The combined organic phases is dried using sodium sulfate, filtered off and evaporated to dryness. The crude product is chromatographed on Si60 (eluent: PE/EA 20/1) The product is obtained as colourless oil (270 mg, 0.001 mol, 18%).

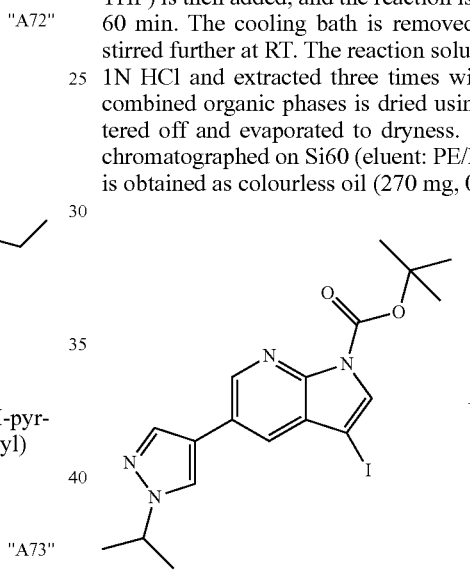

E9

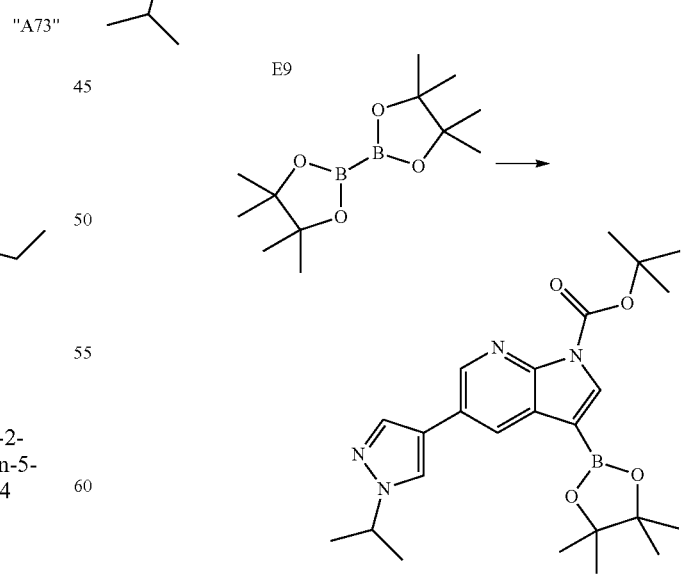

E19

Bis(pinacolato)diboron (5.03 g, 19.89 mmol), potassium acetate (3.84 g, 39.13 mmol) and palladium(II)/dppf complex (0.542 g, 0.663 mmol) are initially introduced in a one-necked flask, and a solution of E9 (1.76 g, 3.89 mmol) in DMF (20 ml) is then added. The reaction is stirred at 80° C. under nitrogen for 3 h.

The reaction is terminated, cooled to RT. EA is added to the black reaction solution, the insoluble residue is filtered off with suction and rinsed with EA. The filtrate is transferred into a separating funnel and extracted rapidly twice with water. The organic phase is dried using sodium sulfate, filtered off and evaporated to dryness. The crude product is chromatographed on Si60 (eluent: PE/EA 1/1) The product E19 is obtained as brown oil (1.75 g, 0.004 mol, 58%)

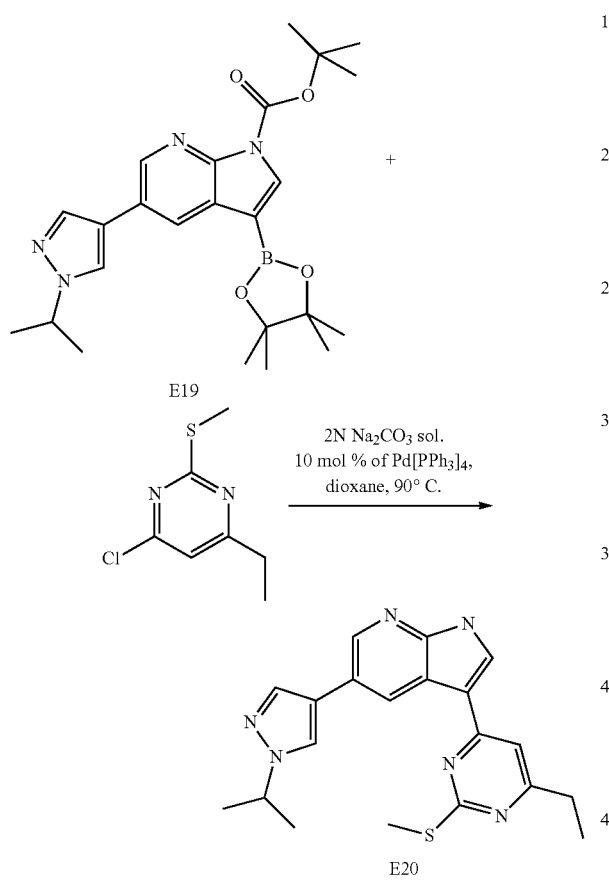

E19 (0.887 g, 1.43 mmol) and 4-chloro-6-ethyl-2-methyl-sulfanyl-p-yrimidine (0.270 g, 1.43 mmol) are dissolved in dioxane (5 ml), the Pd[PPh3]4 was added, and the brown reaction solution was flushed with nitrogen for 5 minutes. The sodium carbonate solution (3.5 ml, 2M) is then added, and the reaction is stirred at 90° C. for 60 min. The reaction is cooled to RT, EA is added, and the mixture is extracted three times with water. The organic phase is dried using sodium sulfate, filtered off and evaporated to dryness. HCl/dioxane is added to the brown oily residue (780 mg). The mixture is treated in an ultrasound bath for 5 minutes and subsequently stirred at RT for 1 h. The precipitate is filtered off with suction and rinsed with dioxane. The filtrate is discarded. 100 mg of the crude product are dissolved in ACN/water and Rp18 chromatographed (Chromolith-prep RP-18e 100-25, eluent A: water+0.1% of TFA, eluent B: acetonitrile+0.1% of TFA, gradient: 99:1-->1:99 in 15 min., flow rate: 30 ml/min). The product is obtained as yellow solid (25 mg, 0.072 mmol, 5%)

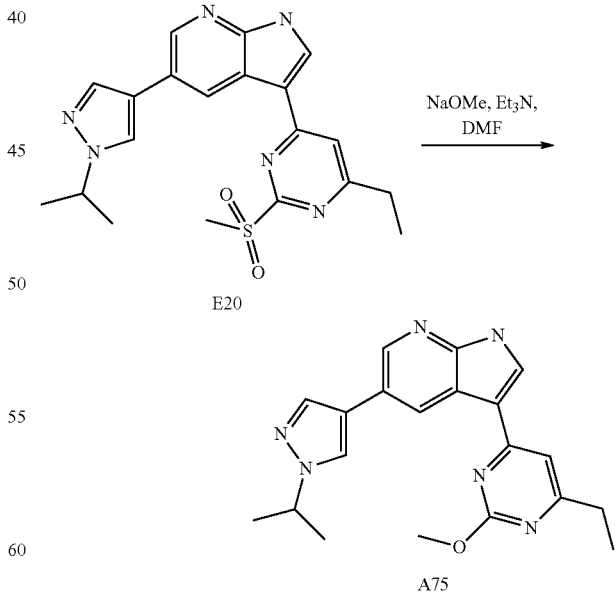

E20 (0.379 g, 0.721 mmol) is suspended in acetic acid (6 ml), sodium perborate trihydrate (0.222 g, 1.442 mmol) is added, and the reaction is stirred at RT for 2 h and then at 40° C. for 2 h.

The reaction is cooled to RT, and water is added, the aqueous phase is extracted three times with EA. The combined organic phases are dried using sodium sulfate, filtered off and evaporated to dryness. 100 mg of the crude product is Rp chromatographed (Chromolith-prep RP-18e 100-25, eluent A: water+0.1% of TFA, eluent B: acetonitrile+0.1% of TFA, gradient: 99:1-->1:99 in 15 min., flow rate: 30 ml/min). The product is obtained as yellow solid (5 mg, 0.007 mmol, 1%)

A76 (210 mg, 0.200 mmol) is dissolved in DMF (3 ml), triethylamine (0.1 ml, 0.721 mmol) and subsequently sodium methoxide (50 mg, 0.926 mmol) are added, and the mixture is stirred overnight at RT.

EA is added to the reaction solution, which is subsequently extracted three times with water. The organic phase is dried using sodium sulfate, filtered off and evaporated to dryness.

The crude product is Rp-chromatographed (Chromolith-prep RP-18e 100-25, eluent A: water+0.1% of TFA, eluent B: acetonitrile+0.1% of TFA, gradient: 99:1-->1:99 in 15 min., flow rate: 30 ml/min). The product is obtained as yellow solid (8 mg, 0.022 mmol, 11%).

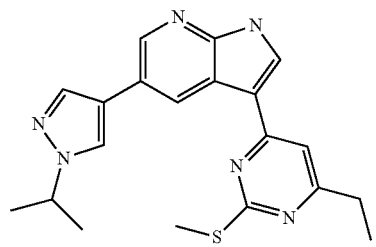

"E20"

3-(6-Ethyl-2-methylsulfanylpyrimidin-4-yl)-5-(1-isopropyl-1H-pyrazol-4-yl)-1H-pyrrolo[2,3-b]pyridine ("A127"), ESI [M+H]=379

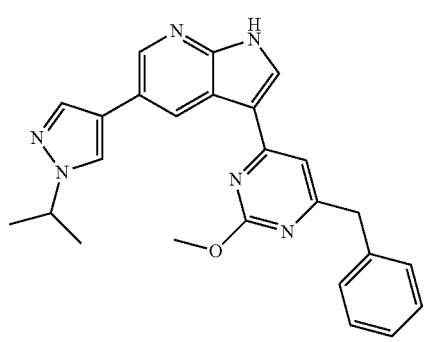

"A74"

3-(6-Benzyl-2-methoxypyrimidin-4-yl)-5-(1-isopropyl-1H-pyrazol-4-yl)-1H-pyrrolo[2,3-b]pyridine ("A74"), ESI [M+H]=425

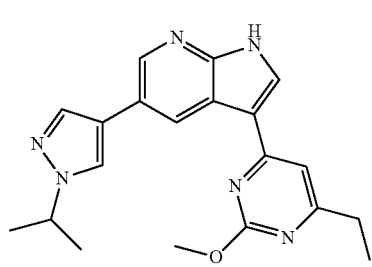

"A75"

3-(6-Ethyl-2-methoxypyrimidin-4-yl)-5-(1-isopropyl-1H-pyrazol-4-yl)-1H-pyrrolo[2,3-b]pyridine ("A75"), ESI [M+H]=363.3, 1H-NMR (d6-DMSO, 400 MHz): δ=1.27 (t, J=4 Hz, 3H), 1.45 (m, 6H), 2.39 (m, 2H), 4.06 (s, 3H), 4.55 (m, 1H), 7.50 (s, 1H), 7.86 (s, 1H), 8.25 (s, 1H), 8.51 (m, 1H), 8.59 (m, 1H), 8.90 (m, 1H), 12.35 (1H, br) ppm

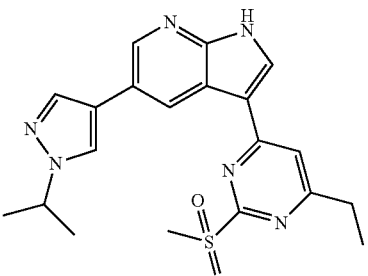

"A76"

3-(6-Ethyl-2-methanesulfonylpyrimidin-4-yl)-5-(1-isopropyl-1H-pyrazol-4-yl)-1H-pyrrolo[2,3-b]pyridine ("A76"), ESI [M+H]=411, 1H-NMR (d6-DMSO, 400 MHz): δ=1.35 (t, J=4 Hz, 3H), 1.49 (m, 6H), 2.88 (q, J=4 Hz, 2H), 3.51 (s. 3H), 4.55 (m, 1H), 7.90 (s, 1H), 8.09 (s, 1H), 8.25 (s, 1H), 8.65 (m, 1H), 8.71 (m, 1H), 8.95 (m, 1H), 12.55 (br, 1H) ppm

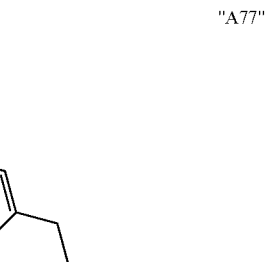

"A77"

3-(6-Ethyl-2-methylsulfanylpyrimidin-4-yl)-1H-pyrrolo[2,3-b]pyridine ("A77"), ESI [M+H]=271, 1H-NMR (d6-DMSO, 400 MHz): δ=1.25 (t, J=4 Hz, 3H), 2.62 (s, 3H), 2.68 (q, J=4 Hz, 2H), 7.25 (m, 1H), 7.50 (s, 1H), 8.3 (m, 1H), 8.55 (m, 1H), 8.79 (m, 1H), 12.4 (1H, br) ppm.

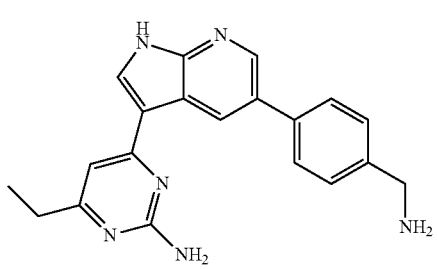

"A81"

4-[5-(4-Aminomethylphenyl)-1H-pyrrolo[2,3-b]pyridin-3-yl]-6-ethylpyrimidin-2-ylamine ("A81"), ESI [M+H]+= 345.2,

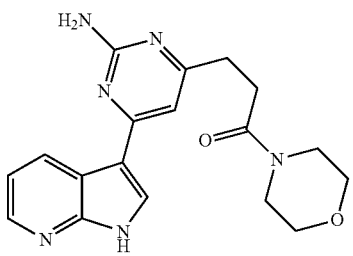

"A82"

3-[2-Amino-6-(1H-pyrrolo[2,3-b]pyridin-3-yl)pyrimidin-4-yl]-1-morpholin-4-ylpropan-1-one ("A82"), ESI [M+H]⁺=353.2,

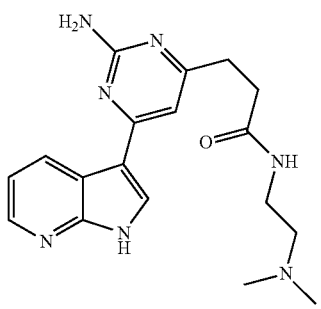

"A83"

3-[2-Amino-6-(1H-pyrrolo[2,3-b]pyridin-3-yl)pyrimidin-4-yl]-N-(2-dimethylaminoethyl)propionamide ("A83"), ESI [M+H]⁺=354.2,

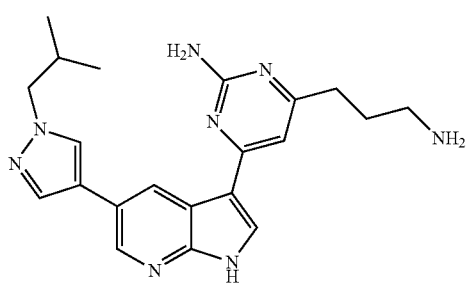

"A84"

4-(3-Aminopropyl)-6-[5-(1-isobutyl-1H-pyrazol-4-yl)-1H-pyrrolo[2,3-b]pyridin-3-yl]pyrimidin-2-ylamine ("A84"), ESI [M+H]⁺=391.2,

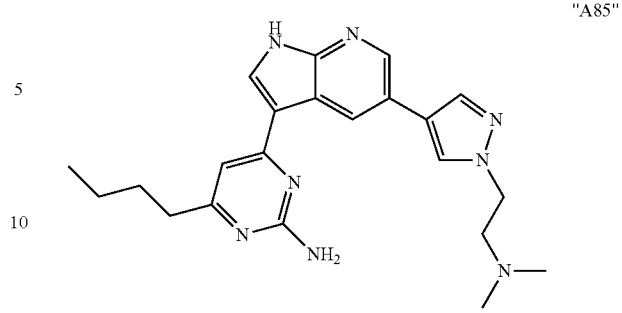

"A85"

4-Butyl-6-{5-[1-(2-dimethylaminoethyl)-1H-pyrazol-4-yl]-1H-pyrrolo[2,3-b]-pyridin-3-yl}pyrimidin-2-ylamine ("A85"), ESI [M+H]⁺=405.2,

"A86"

1-(4-{4-[3-(2-Amino-6-butylpyrimidin-4-yl)-1H-pyrrolo[2,3-b]pyridin-5-yl]-pyrazol-1-yl}piperidin-1-yl)ethanone ("A86"), ESI [M+H]⁺=459.3,
1H-NMR (d6-DMSO, 400 MHz): δ=0.95 (t, J=7.0 Hz, 3H), 1.40 (m, 2H), 1.71 (m, 2H), 1.75-2.00 (m, 2H), 2.08 (s, 3H), 2.10-2.17 (m, 1H), 2.67-2.80 (m, 3H), 3.25 (m, 2H), 3.95 (m, 2H), 4.55 (m, 1H), 7.38 (s, 1H), 8.51 (s, 1H), 8.39 (s, 1H), 8.65 (d, J=2 Hz, 1H), 8.88 (m, 1H), 9.03 (d, J=2 Hz, 1H), 12.81 (s, 1H) ppm.

"A87"

4-Butyl-6-[5-(1-piperidin-4-yl-1H-pyrazol-4-yl)-1H-pyrrolo[2,3-b]pyridin-3-yl]-pyrimidin-2-ylamine ("A87"), ESI [M+H]⁺=417.2,
1H-NMR (d6-DMSO, 400 MHz): δ=0.95 (t, J=8.0 Hz, 3H), 1.40 (m, 2H), 1.71 (m, 2H), 2.10-2.36 (m, 4H), 2.78 (d, J=8 Hz, 2H), 3.15 (m, 2H), 3.45 (m, 2H), 3.70 (br, 1H), 4.55 (m, 1H), 7.38 (s, 1H), 8.21 (s, 1H), 8.39 (s, 1H), 8.50 (m, 2H), 8.68 (d, J=2 Hz, 1H), 8.88 (m, 1H), 9.05 (d, J=2 Hz, 1H), 12.81 (s, 1H) ppm.

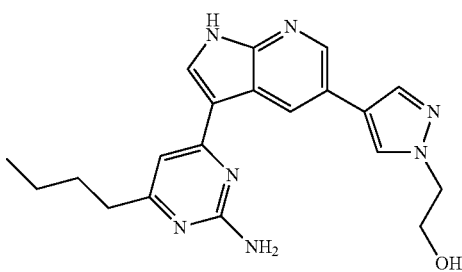

"A88"

2-{4-[3-(2-Amino-6-butylpyrimidin-4-yl)-1H-pyrrolo[2,3-b]pyridin-5-yl]pyrazol-1-yl}ethanol ("A88"), ESI [M+H]$^+$=378.2,

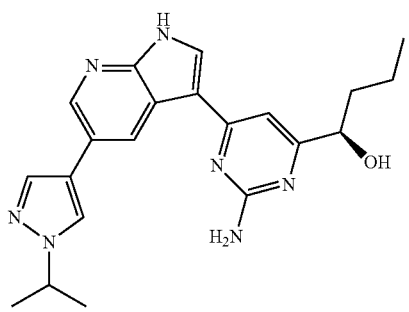

"A91"

(R)-1-{2-Amino-6-[5-(1-isopropyl-1H-pyrazol-4-yl)-1H-pyrrolo[2,3-b]pyridin-3-yl]pyrimidin-4-yl}butan-1-ol ("A91"), ESI [M+H]$^+$=392

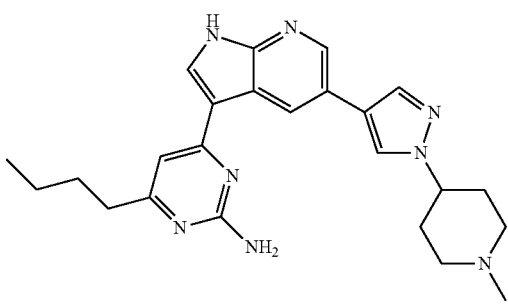

"A89"

4-Butyl-6-{5-[1-(1-methylpiperidin-4-yl)-1H-pyrazol-4-yl]-1H-pyrrolo[2,3-b]-pyridin-3-yl}pyrimidin-2-ylamine ("A89"), ESI [M+H]$^+$=431.2, 1H-NMR (d6-DMSO, 400 MHz): δ=0.95 (t, J=8.0 Hz, 3H), 1.40 (m, 2H), 1.71 (m, 2H), 2.15-2.36 (m, 4H), 2.76 (d, J=7 Hz, 2H), 2.85 (s, 3H), 3.20 (m, 2H), 3.50 (m, 2H), 4.51 (m, 1H), 7.36 (s, 1H), 8.20 (s, 1H), 8.38 (s, 1H), 8.68 (d, J=2 Hz, 1H), 8.76 (s, 1H), 9.05 (d, J=2 Hz, 1H), 12.75 (s, 1H) ppm

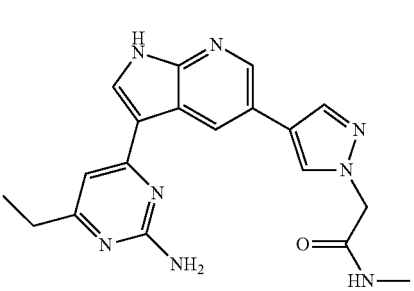

"A92"

2-{4-[3-(2-Amino-6-ethylpyrimidin-4-yl)-1H-pyrrolo[2,3-b]pyridin-5-yl]pyrazol-1-yl}-N-methylacetamide ("A92"), ESI [M+H]=377

1H-NMR (d6-DMSO, 400 MHz): δ=1.29 (t, J=8.4 Hz, 3H), 2.60-2.85 (m, 2H), 2.95 (d, J=3 Hz, 3H), 4.82-4.89 (m, 2H), 6.55 (s, 2H), 7.05 (s, 1H), 8.17 (s, 1H), 8.36 (s, 1H), 8.62 (d, J=2 Hz, 1H), 9.10 (d, J=2 Hz, 1H), 12.15 (s, 1H) ppm.

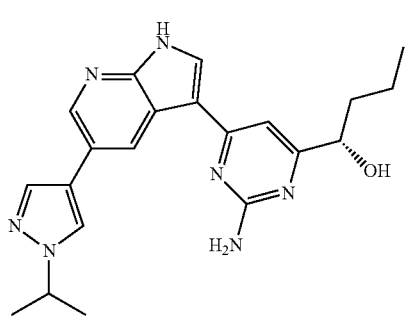

"A90"

(S)-1-{2-Amino-6-[5-(1-isopropyl-1H-pyrazol-4-yl)-1H-pyrrolo[2,3-b]pyridin-3-yl]pyrimidin-4-yl}butan-1-ol ("A90"), ESI [M+H]$^+$=392

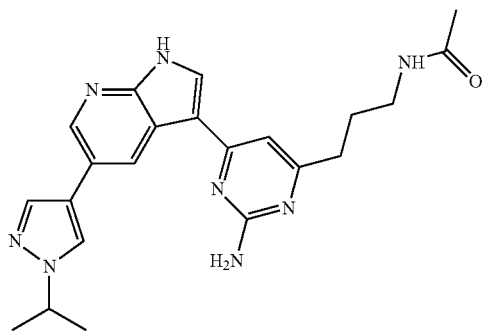

"A97"

N-(3-{2-Amino-6-[5-(1-isopropyl-1H-pyrazol-4-yl)-1H-pyrrolo[2,3-b]pyridin-3-yl]pyrimidin-4-yl}propyl)acetamide ("A97"), ESI [M+H]$^+$=419.2,

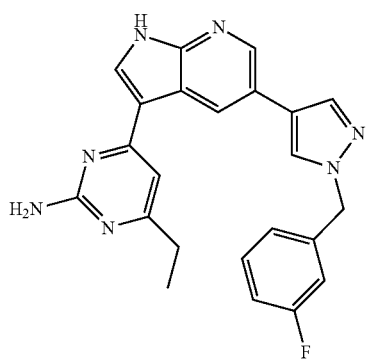

"A98"

4-Ethyl-6-{5-[1-(3-fluorobenzyl)-1H-pyrazol-4-yl]-1H-pyrrolo[2,3-b]pyridin-3-yl}pyrimidin-2-ylamine ("A98"), ESI [M+H]$^+$=414,

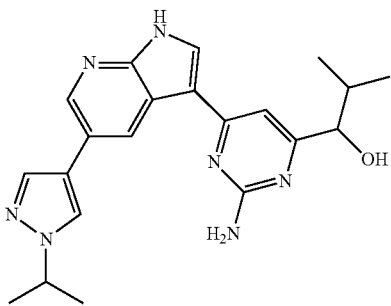

"A102"

1-{2-Amino-6-[5-(1-isopropyl-1H-pyrazol-4-yl)-1H-pyrrolo[2,3-b]pyridin-3-yl]-pyrimidin-4-yl}-2-methylpropan-1-ol ("A102"), ESI [M+H]$^+$=392.3, 1H-NMR (d6-DMSO, 500 MHz): δ=0.80 (d, J=6.7 Hz, 3H), 0.94 (d, J=6.7 Hz, 3H), 1.48 (d, J=6.5 Hz, 6H), 2.19 (m, 1H), 4.35 (d, J=4.9 Hz, 1H), 4.53 (m, 1H), 5.10 (s, 1H), 6.52 (s, 2H), 7.10 (s, 1H), 8.05 (s, 1H), 8.20 (s, 1H), 8.26 (d, J=2.9 Hz, 1H), 8.30 (s, 1H), 8.55 (d, J=2.2 Hz, 1H), 9.05 (d, J=2.1 Hz, 1H), 12.07 (s, 1H) ppm.

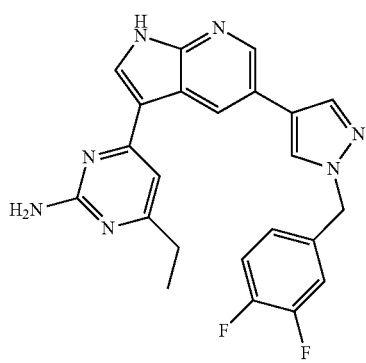

"A99"

4-{5-[1-(3,4-Difluorobenzyl)-1H-pyrazol-4-yl]-1H-pyrrolo[2,3-b]pyridin-3-yl}-6-ethylpyrimidin-2-ylamine ("A99"), ESI [M+H]$^+$=432,

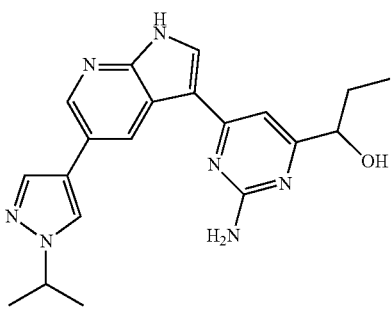

"A103"

1-{2-Amino-6-[5-(1-isopropyl-1H-pyrazol-4-yl)-1H-pyrrolo[2,3-b]pyridin-3-yl]-pyrimidin-4-yl}propan-1-ol ("A103"), ESI [M+H]$^+$=378,

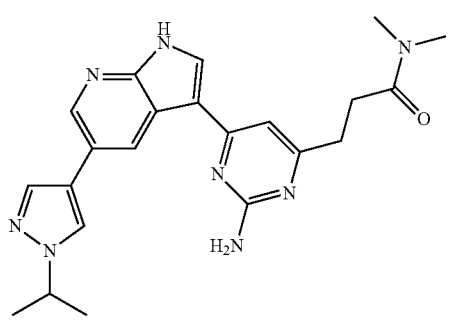

"A101"

3-{2-Amino-6-[5-(1-isopropyl-1H-pyrazol-4-yl)-1H-pyrrolo[2,3-b]pyridin-3-yl]-pyrimidin-4-yl}-N,N-dimethylpropionamide ("A101"), ESI [M+H]$^+$=419,

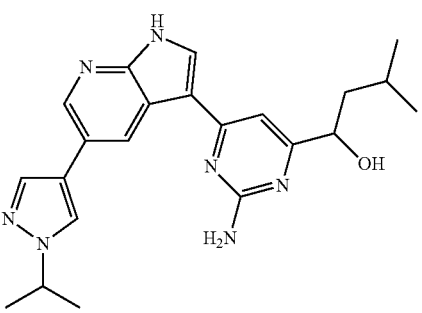

"A104"

1-{2-Amino-6-[5-(1-isopropyl-1H-pyrazol-4-yl)-1H-pyrrolo[2,3-b]pyridin-3-yl]-pyrimidin-4-yl}-3-methylbutan-1-ol ("A104"), ESI [M+H]$^+$=406.2, 1H-NMR in DMSO [ppm] 12.18 (1H, NH), 9.08 (s, 1H), 8.57 (s, 1H), 8.32 (s, 1H), 8.28 (s, 1H), 8.20 (s, 1H), 8.16 (s, 1H), 7.15 (s, 1H), 6.57 (s, 2H), 5.18 (d, 1H, J=8 Hz), 4.55 (h, 1H, J=8 Hz), 4.35 (m, 1H), 1.86 (m, 1H), 1.52 (m, 2H), 1.50 (m, 6H), 0.95 (m, 6H)

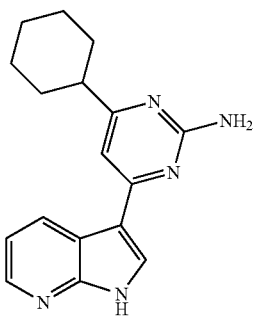

"A105"

4-Cyclohexyl-6-(1H-pyrrolo[2,3-b]pyridin-3-yl)pyrimidin-2-ylamine ("A105"), ESI [M+H]⁺=294

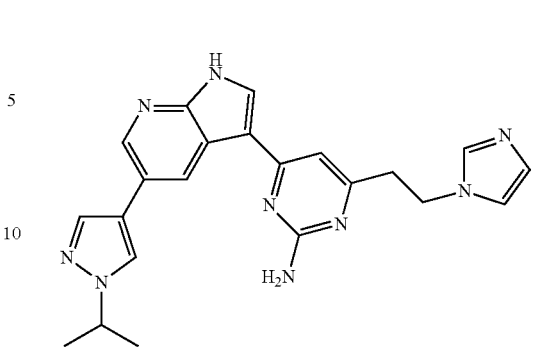

"A110"

4-(2-Imidazol-1-ylethyl)-6-[5-(1-isopropyl-1H-pyrazol-4-yl)-1H-pyrrolo[2,3-b]-pyridin-3-yl]pyrimidin-2-ylamine ("A110"), ESI [M+H]⁺=414,

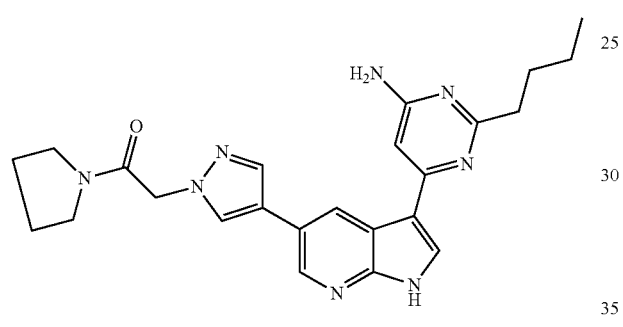

"A106"

2-{4-[3-(2-Amino-6-butylpyrimidin-4-yl)-1H-pyrrolo[2,3-b]pyridin-5-yl]pyrazol-1-yl}-1-pyrrolidin-1-ylethanone ("A106"), ESI [M+H]⁺=445.2,

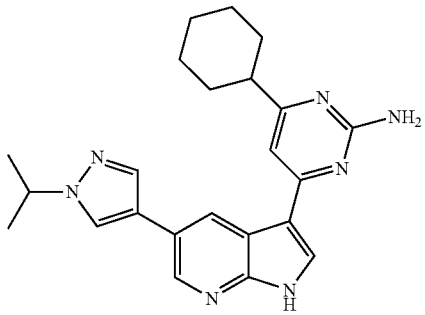

"A111"

4-Cyclohexyl-6-[5-(1-isopropyl-1H-pyrazol-4-yl)-1H-pyrrolo[2,3-b]pyridin-3-yl]pyrimidin-2-ylamine ("A111"), ESI [M+H]⁺=402

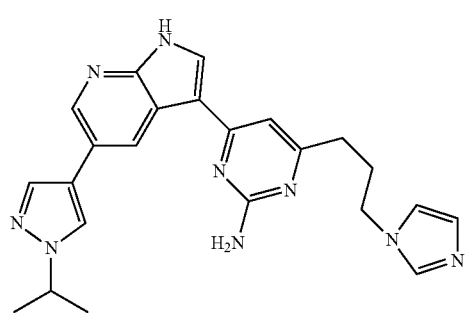

"A108"

4-(3-Imidazol-1-ylpropyl)-6-[5-(1-isopropyl-1H-pyrazol-4-yl)-1H-pyrrolo-[2,3-b]pyridin-3-yl]pyrimidin-2-ylamine ("A108"), ESI [M+H]⁺=428.2,

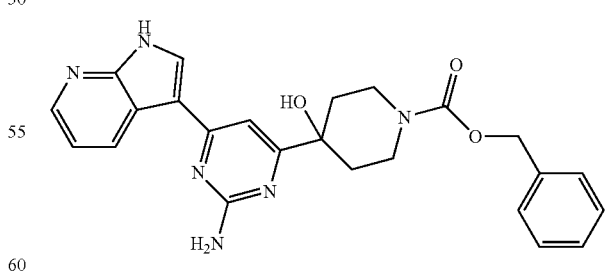

"A113"

4-[2-Amino-6-(1H-pyrrolo[2,3-b]pyridin-3-yl)pyrimidin-4-yl]-4-hydroxypiperidine-1-carboxylic acid benzyl ester ("A113"), ESI [M+H]⁺=445.2,

"A114"

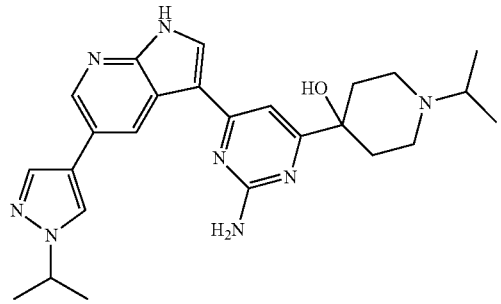

4-{2-Amino-6-[5-(1-isopropyl-1H-pyrazol-4-yl)-1H-pyrrolo[2,3-b]pyridin-3-yl]-pyrimidin-4-yl}-1-isopropylpiperidin-4-ol ("A114"), ESI [M+H]$^+$=461.2,

"A115"

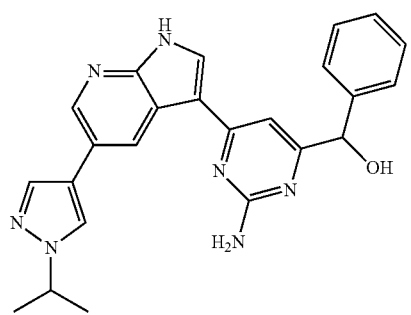

{2-Amino-6-[5-(1-isopropyl-1H-pyrazol-4-yl)-1H-pyrrolo[2,3-b]pyridin-3-yl]-pyrimidin-4-yl}phenylmethanol ("A115"), ESI [M+H]$^+$=426.7, 1H-NMR (d6-DMSO, 400 MHz): δ=1.49 (d, J=6.7 Hz, 6H), 1.76 (s, 1H), 4.56 (m, 1H), 5.75 (s, 1H), 6.69 (s, 2H), 7.13 (s, 1H), 7.55 (t, 2H), 7.60 (s, 1H), 7.96 (s, 1H), 8.15 (m, 2H), 8.36 (s, 1H), 8.66 (d, J=2.1 Hz, 1H), 8.77 (d, J=2.0 Hz, 1H), 9.09 (d, J=3.1 Hz, 1H), 12.76 (s, 1H) ppm.

"A116"

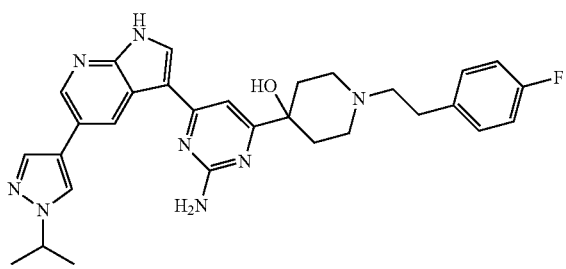

4-{2-Amino-6-[5-(1-isopropyl-1H-pyrazol-4-yl)-1H-pyrrolo[2,3-b]pyridin-3-yl]-pyrimidin-4-yl}-1-[2-(4-fluorophenyl)ethyl]piperidin-4-ol ("A116"), ESI [M+H]$^+$=541.2,

"A121"

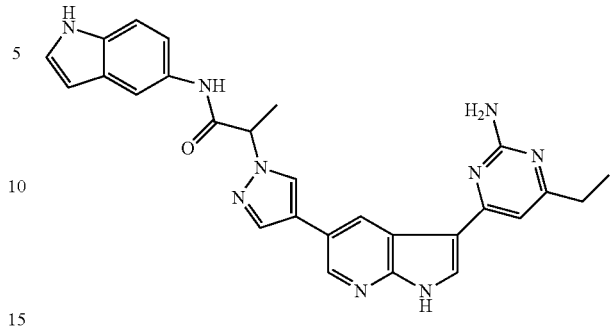

2-{4-[3-(2-Amino-6-ethylpyrimidin-4-yl)-1H-pyrrolo[2,3-b]pyridin-5-yl]pyrazol-1-yl}-N-(1H-indol-5-yl)propionamide ("A121"), ESI [M+H]$^+$=492.2,

"A122"

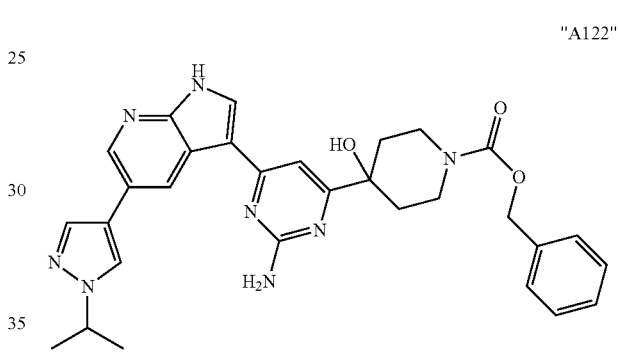

4-{2-Amino-6-[5-(1-isopropyl-1H-pyrazol-4-yl)-1H-pyrrolo[2,3-b]pyridin-3-yl]-pyrimidin-4-yl}-4-hydroxypiperidine-1-carboxylic acid benzyl ester ("A122"), ESI [M+H]$^+$=553.2,

"A123"

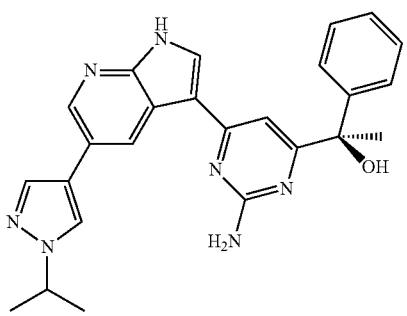

(R)-1-{2-Amino-6-[5-(1-isopropyl-1H-pyrazol-4-yl)-1H-pyrrolo[2,3-b]pyridin-3-yl]pyrimidin-4-yl}-1-phenylethanol ("A123"), ESI [M+H]$^+$=440

"A124"

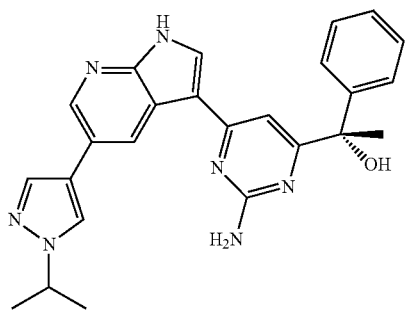

(S)-1-{2-Amino-6-[5-(1-isopropyl-1H-pyrazol-4-yl)-1H-pyrrolo[2,3-b]pyridin-3-yl]pyrimidin-4-yl}-1-phenylethanol ("A124"), ESI [M+H]$^+$=440

"A125"

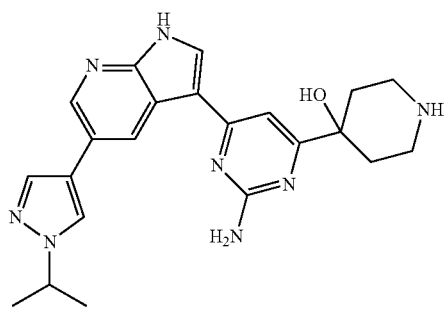

4-{2-Amino-6-[5-(1-isopropyl-1H-pyrazol-4-yl)-1H-pyrrolo[2,3-b]pyridin-3-yl]-pyrimidin-4-yl}piperidin-4-ol ("A125"), ESI [M+H]$^+$=419.2,

"A128"

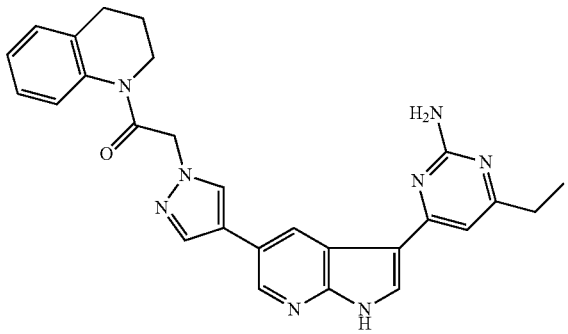

2-{4-[3-(2-Amino-6-ethylpyrimidin-4-yl)-1H-pyrrolo[2,3-b]pyridin-5-yl]pyrazol-1-yl}-1-(3,4-dihydro-2H-quinolin-1-yl)ethanone ("A128"), ESI [M+H]$^+$=479.2, PDK1

$IC_{50}$ of compounds according to the invention

| Compound No. | $IC_{50}$ cells A2780 (ovary) |
|---|---|
| "A2" | A |
| "A3" | A |
| "A4" | B |
| "A5" | A |
| "A6" | B |
| "A7" | A |
| "A8" | B |
| "A55" | A |
| "A59" | A |
| "A91" | A |
| "A90" | A |
| "A102" | B |
| "A123" | A |
| "A124" | A |

| | $IC_{50}$ PDK1 |
|---|---|
| "A1" | A |
| "A2" | A |
| "A3" | A |
| "A4" | A |
| "A5" | A |
| "A6" | A |
| "A7" | A |
| "A8" | A |
| "A9" | A |
| "A10" | A |
| "A11" | A |
| "A29" | A |
| "A30" | A |
| "A31" | A |
| "A32" | A |
| "A33" | A |
| "A34" | A |
| "A35" | A |
| "A36" | A |
| "A37" | B |
| "A38" | A |
| "A39" | A |
| "A40" | A |
| "A41" | A |
| "A42" | B |
| "A43" | A |
| "A44" | A |
| "A45" | B |
| "A46" | A |
| "A48" | B |
| "A49" | B |
| "A50" | B |
| "A51" | A |
| "A52" | A |
| "A53" | A |
| "A54" | A |
| "A55" | A |
| "A58" | A |
| "A59" | A |
| "A60" | A |
| "A61" | A |
| "A62" | A |
| "A63" | A |
| "A64" | A |
| "A65" | A |
| "A66" | A |
| "A67" | A |
| "A68" | A |
| "A60" | A |
| "A70" | A |
| "A71" | A |
| "A72" | A |
| "A73" | A |
| "A74" | B |
| "A75" | A |
| "A81" | A |
| "A82" | B |
| "A83" | B |
| "A84" | A |
| "A85" | A |
| "A86" | A |
| "A87" | A |
| "A88" | A |
| "A89" | A |
| "A90" | A |
| "A91" | A |
| "A97" | A |

-continued

| Compound | Value |
|---|---|
| "A98" | A |
| "A99" | A |
| "A101" | A |
| "A102" | A |
| "A103" | A |
| "A104" | A |
| "A105" | A |
| "A106" | A |
| "A108" | A |
| "A110" | A |
| "A111" | A |
| "A113" | B |
| "A114" | A |
| "A115" | B |
| "A116" | A |
| "A121" | A |
| "A122" | A |
| "A123" | A |
| "A124" | A |
| "A125" | B |
| "A128" | A |

$IC_{50}$: 10 nM-1 µM = A
1 µM-10 µM = B

Method for the Cellular Testing of PDK1 Kinase Inhibitors in PC3 Cells.

The cellular assay for the determination of the PDK1 kinase activity is carried out as a Luminex assay in the 96-well format. PC3 cells are sown at 20,000 cells per well in 100 µl of medium (45% of RPMI1460/45% of Ham's F12/10% of FCS) and incubated on the following day for 30 min with a serial dilution of the test substance (7 concentrations) under serum-free conditions. The cells are subsequently lysed using 90 µl of lysis buffer (20 mM tris/HCl pH 8.0, 150 mM NaCl, 1% of NP40, 10% of glycerol, 1% of phosphatase inhibitor I, 1% of phosphatase inhibitor II, 0.1% of protease inhibitor cocktail III, 0.01% of benzonase) per well, and the lysates are separated off from insoluble cell constituents by means of centrifugation through a 96-well filter plate (0.65 µm). The lysates are incubated overnight at 4° C. with shaking with Luminex beads to which an anti-total PKB antibody is coupled. The detection is carried out on the following day by addition of a phospho-T308-PKB antibody and a species-specific peroxidase-labelled secondary antibody. The detection of phospho-T308-PKB is carried out by measurement in a Luminex100 instrument by determination of 100 events per cavity in a measurement time of 60 sec. As pharmacological blank, the signals obtained from cells which have been treated with 10 µM staurosporin are subtracted from all other batches. The control value used for maximum phosphorylation of PKB on T308 are the signals from cells which have only been treated with the solvent (0.3% of DMSO). The values of the batches treated with test substance are calculated therefrom as percentage of control, and IC50 values are determined by means of RS1.

| Compound No. | IC50 [PC3 P-PKB Thr308] |
|---|---|
| "A1" | C |
| "A2" | C |
| "A3" | C |
| "A4" | B |
| "A5" | B |
| "A6" | C |
| "A7" | C |
| "A8" | B |
| "A9" | C |
| "A10" | B |
| "A11" | C |
| "A29" | C |
| "A30" | C |
| "A31" | C |
| "A32" | C |
| "A33" | C |
| "A34" | C |
| "A35" | B |
| "A36" | C |
| "A37" | C |
| "A38" | C |
| "A39" | C |
| "A40" | B |
| "A41" | C |
| "A42" | C |
| "A43" | C |
| "A44" | B |
| "A46" | C |
| "A48" | C |
| "A49" | C |
| "A50" | C |
| "A51" | C |
| "A52" | C |
| "A53" | C |
| "A54" | C |
| "A55" | A |
| "A58" | B |
| "A59" | A |
| "A81" | B |
| "A85" | B |
| "A86" | B |
| "A87" | B |
| "A88" | B |
| "A89" | B |
| "A90" | B |
| "A91" | A |
| "A97" | C |
| "A98" | B |
| "A99" | C |
| "A101" | C |
| "A102" | B |
| "A103" | C |
| "A104" | B |
| "A105" | C |
| "A106" | B |
| "A108" | C |
| "A110" | C |
| "A111" | B |
| "A113" | B |
| "A114" | C |
| "A115" | C |
| "A116" | C |
| "A121" | B |
| "A122" | C |
| "A123" | A |
| "A124" | A |
| "A125" | C |
| "A128" | B |

$IC_{50}$: 10 nM-1 µM = A
1 µM-10 µM = B
10 µM-20 µM = C

The following examples relate to medicaments:

EXAMPLE A

Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

EXAMPLE C

Solution

A solution is prepared from 1 g of an active ingredient of the formula I, 9.38 g of $NaH_2PO_4.2H_2O$, 28.48 g of $Na_2HPO_4.12\,H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

---

The invention claimed is:

1. A compound of formula I

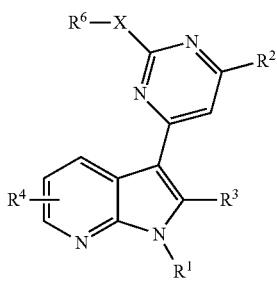

wherein
R¹ denotes H or A,
R² denotes A, Hal, CN, (CH₂)ₙCONH(CH₂)ₚAr, —C(OH)R⁵—Ar, —[C(R⁵)₂]ₙ—Ar, —[C(R⁵)₂]ₙ-Het, —[C(R⁵)₂]ₙ-cycloalkyl, —NR⁵A, —NR⁵Ar, NR⁵Het, —[C(R⁵)₂]ₘN(R⁵)₂, 1-hydroxycyclopentan-1-yl or 1-hydroxycyclohexan-1-yl,
R³ denotes H, R⁵, —[C(R⁵)₂]ₙ—Ar, —[C(R⁵)₂]ₙ-Het, or —[C(R⁵)₂]ₙ-cycloalkyl,
R⁴ denotes H, Het-, Ar—, —R⁵, —OR⁵, —[C(R⁶)₂]ₙC(O)N(R⁶)₂, CO-Het or O(CH₂)ₚHet¹,
R⁵ denotes H, A or cycloalkyl,
R⁶ denotes H or A',
A' denotes unbranched or branched alkyl having 1-10 C atoms, in which 1-7 H atoms are each optionally replaced by F,
cycloalkyl denotes a cyclic alkyl having 3-7 C atoms, which is optionally substituted by alkyl having 1-6 C atoms,
A denotes unbranched or branched alkyl having 1-10 C atoms, in which one or two CH and/or CH₂ groups are each optionally replaced by N, O, S atoms and/or by —CH═CH— groups and/or in addition 1-7 H atoms are each optionally replaced by F,
X denotes NH, O, S or SO₂,
Ar denotes phenyl which is unsubstituted or mono-, di- or trisubstituted by Hal, A, OR⁵, N(R⁵)₂, NO₂, CN, COOR⁵, CON(R⁵)₂, NR⁵COA, NR⁵SO₂A, COR⁵, SO₂N(R⁵)₂ and/or S(O)ₚA,
Het denotes a mono- or bicyclic saturated, unsaturated or aromatic heterocycle having 1 to 4 N, and/or O and/or S atoms which is unsubstituted or mono- or disubstituted by Hal, A, OR⁵, (CH₂)ₚN(R⁵)₂, NO₂, CN, (CH₂)ₚCOOR⁵, (CH₂)ₚCON(R⁵)₂, NR⁵COA, (CH₂)ₚHet¹, (CH₂)ₚCOHet¹, NR⁵SO₂A, COR⁵, SO₂NR⁵ and/or S(O)ₚA,
Het¹ denotes a saturated heterocycle having 1 to 4 N, O, and or S atoms which is unsubstituted or mono- or disubstituted by A, S(O)ₚA and/or COA,
Hal denotes F, Cl, Br or I,
m denotes 1, 2, 3 or 4,
n denotes 0, 1, 2, 3 or 4,
p denotes 0, 1 or 2,
or a pharmaceutically usable salts, tautomers and stereoisomers thereof, including mixtures thereof in all ratios.

2. A compound according to claim 1, in which R¹ and R³ denotes H, and pharmaceutically usable salts, tautomers and stereoisomers thereof, including mixtures thereof in all ratios.

3. A compound according to claim 1, in which R² denotes ethyl, aminopropyl, morpholin-4-ylmethyl, piperazin-1-ylmethyl, dimethylaminomethyl, methylaminomethyl, 3-dimethylaminopropyl, 3-methylaminopropyl, 1-hydroxycyclopentan-1-yl, 1-hydroxycyclohexan-1-yl, morpholin-4-ylpropyl, 1-(morpholin-4-yl)-1-oxopropanyl, 1-[(2-dimethylaminoethyl)amino]-1-oxopropanyl, 3-aminopropanyl, 1 hydroxybutyl, 1-[(3,4-difluorobenzyl)amino]-1-oxopropanyl, methylamino, 3-acetamidopropyl, 2-(dimethylaminocarbonyl)ethyl, 1-hydroxy-2-methylpropyl, 1-hydroxypropyl, 1-hydroxy-3-methylbutyl, cyclohexyl, propyl, butyl, 3-imidazolepropyl, 2-imidazolethyl, 1-(benzyloxycarbonyl)-4-hydroxypiperidin-4-yl, 1-isopropyl-4-hydroxypiperidin-4-ylm, 1-hydroxy-1-phenylmethyl, 1-[2-(4-fluorophenyl)-ethyl]-4-hydroxypiperidin-4-yl, 4-hydroxypiperidin-4-yl or 1-phenyl-1-hydroxypropyl,
and pharmaceutically usable salts, tautomers and stereoisomers thereof, including mixtures thereof in all ratios.

4. A compounds according to claim 1, in which R⁴ denotes H, 1-(tetrahydrofuran-2-ylmethyl)-1H-pyrazolyl, methyl-(2-pyrazol-1-ylethyl)amino, dimethyl-(3-pyrazol-1-ylpropyl)amino, dimethyl-(2-pyrazol-1-ylethyl)amino, 1-methyl-4-pyrazol-1-ylpiperidinyl, 4-pyrazol-1-ylpiperidinyl, 1-phenylpiperazinyl, 1-(2-pyrrolidin-1-ylethyl)-1H-pyrazolyl, 4-(2-pyrazolyl-1-ylethyl)morpholinyl, 1-pyrrolidin-3-ylmethyl-1H-pyrazolyl, 3-[N-(2-dimethylaminoethyl)aminocarbonyl]phenyl, 4-methylpiperazine-1-carbonyl, morpholine-4-carbonyl, N-(4-dimethylaminobutyl)aminocarbonyl, 2-dimethylaminoethoxy, piperidin-4-ylmethoxy, C-piperidin-4-ylmethylamino, CH₃NH(CH₂)₄NH—, (CH₃)₂N(CH₂)₄NH—, 2-(tetrahydrofuran-2-ylmethyl)oxazolyl, 2-(tetrahydrofuran-2-ylmethyl)-1H-imidazolyl, 1-(tetrahydrofuran-2-ylmethyl)-1H-imidazolyl, 1-benzyl-1H-1,2,3-triazolyl 5-phenyloxazolyl, 4-aminomethylphenyl, 1-(1-acetylpiperidin-4-yl)pyrazol-4-yl, 1-piperidin-4-ylpyrazol- 4-yl), 1-(2-hydroxyethyl)pyrazol-4-yl), 1-(1-methylpiperidin-4-yl)pyrazol-4-yl, 2-isopropylpyrazol-4-yl, 1-(2-oxo-2-methyl-aminoethyl) pyrazol-4-yl, 1-[2-dimethylaminoethyl]pyrazol-4-yl, pyrazolyl, 1-methylpyrazol-4-yl, 1-(3-fluorobenzyl)pyrazol-4-yl, 1-(3,4-difluorobenzyl)pyrazol-4-y, 1-[1-(piperidin-1-yl)-acetyl]pyrazol-4-yl, 1-[1-(pyrrolidin-1-yl)acetyl]pyrazol-4-yl, 1-[3-(indol-5-ylamino)-3-oxo-propan-2-yl]pyrazol-4yl or 1-(3,4-dihydro-2H-quinolin-1-ylcarbonylmethyl)pyrazol-4-yl, and pharmaceutically usable salts, tautomers and stereoisomers thereof, including mixtures thereof in all ratios.

5. A compound according to claim 1, in which A denotes unbranched or branched alkyl having 1-8 C atoms, in which one or two CH and/or $CH_2$ groups may be replaced by N, or O atoms and/or by —CH═CH— groups and/or in addition 1-7 H atoms may be replaced by F, and pharmaceutically usable salts, tautomers and stereoisomers thereof, including mixtures thereof in all ratios.

6. A compound according to claim 1, in which Ar denotes phenyl which is unsubstituted or mono- or disubstituted by $N(R^5)_2$, Hal, and/or $CON(R^5)_2$, and pharmaceutically usable salts, tautomers and stereoisomers thereof, including mixtures thereof in all ratios.

7. A compound according to claim 1, in which Het denotes a mono- or bicyclic saturated, unsaturated or aromatic heterocycle having 1 to 3 N and/or O atoms which is unsubstituted or mono-, di- or trisubstituted by A, OH, OA, Hal, $(CH_2)_p Het^1$ $(CH_2)_p N(R^5)_2$, $NO_2$, CN, $(CH_2)_p COOR^5$, $(CH_2)_p CON(R^5)_2$, $NR^5 COA$, $(CH_2)_p Het^1$, $(CH_2)_p COHet^1$ and/or ═O (carbonyl oxygen), and pharmaceutically usable salts, tautomers and stereoisomers thereof, including mixtures thereof in all ratios.

8. A compound according to claim 1, in which Het denotes dihydropyrrolyl, pyrrolidinyl, tetrahydroimidazolyl, dihydropyrazolyl, tetrahydropyrazolyl, dihydropyridyl, tetrahydropyridyl, piperidinyl, morpholinyl, hexahydropyridazinyl, hexahydropyrimidinyl, piperazinyl, 1,2,3,4-tetrahydroquinolyl, 1,2,3,4-tetrahydroisoquinolyl, 3,4-dihydrobenzo-1,4-oxazinyl, 2,3-dihydroisoindolyl, 2,3-dihydroindolyl, oxazolidinyl, isoxazolidinyl, oxadiazolidinyl, thiazolidinyl, furyl, thienyl, pyrrolyl, imidazolyl, pyrazolyl, oxazolyl, isoxazolyl, thiazolyl, pyridyl, pyrimidinyl, triazolyl, tetrazolyl, thiadiazole, pyridazinyl, pyrazinyl, indolyl, isoindolyl, benzimidazolyl, indazolyl, quinolyl or 1,3-benzodioxolyl, each of which is unsubstituted or mono-, di- or trisubstituted by A, Ar, $(CH_2)_p Het^1$, OH, OA, Hal, $(CH_2)_p N(R^5)_2$, $NO_2$, CN, $(CH_2)_p COOR^5$, $(CH_2)_p CON(R^5)_2$, $NR^5 COA$, $(CH_2)_p COHet^1$, F and/or ═O, and pharmaceutically usable salts, tautomers and stereoisomers thereof, including mixtures thereof in all ratios.

9. A compound according to claim 1, in which Het denotes dihydropyrrolyl, pyrrolidinyl, tetrahydroimidazolyl, dihydropyrazolyl, tetrahydropyrazolyl, morpholinyl, piperazinyl, imidazolyl, pyrazolyl, oxazolyl, isoxazolyl, pyridyl, pyrimidinyl or triazolyl, dihydropyridyl, tetrahydropyridyl, piperidinyl, hexahydropyridazinyl, hexahydropyrimidinyl, piperazinyl, 1,2,3,4-tetrahydroquinolyl, 1,2,3,4-tetrahydroisoquinolyl, 3,4-dihydrobenzo-1,4-oxazinyl, 2,3-dihydroisoindolyl, 2,3-dihydroindolyl, pyrazolyl, pyridyl, furyl or isooxazyl, each of which is unsubstituted or mono- or di-, or trisubstituted by A, $(CH_2)_p Het^1$, $(CH_2)_p N(R^5)_2$, $NO_2$, CN, $(CH_2)_p COOR^5$, $(CH_2)_p CON(R^5)_2$, $NR^5 COA$, $(CH_2)_p COHet^1$, F and/or ═O, and pharmaceutically usable salts, tautomers and stereoisomers thereof, including mixtures thereof in all ratios.

10. A compound according to claim 1, in which $Het^1$ denotes tetrahydrofuranyl, piperidinyl, piperazinyl, pyrrolidinyl, or morpholinyl, each of which is unsubstituted or monosubstituted by A, COA or $S(O)_p A$, and pharmaceutically usable salts, tautomers and stereoisomers thereof, including including mixtures thereof in all ratios.

11. A compound according to claim 1, in which
$R^1$ denotes H,
$R^2$ denotes ethyl, aminopropyl, morpholin-4-ylmethyl, piperazin-1-ylmethyl, dimethylaminomethyl, methylaminomethyl, 3-dimethylaminopropyl, 3-methylaminopropyl, 1-hydroxycyclopentan-1-yl, 1-hydroxycyclohexan-1-yl, morpholin-4-ylpropyl, 1-(morpholin-4-yl)-1-oxopropanyl, 1-[(2-dimethylaminoethyl) amino]-1-oxopropanyl, 3-aminopropanyl, 1hydroxybutyl, 1-[(3,4-difluorobenzyl)amino]-1-oxopropanyl, methylamino, 3-acetamidopropyl, 2-(dimethylaminocarbonyl)ethyl, 1-hydroxy-2-methylpropyl, 1-hydroxypropyl, 1-hydroxy-3-methylbutyl, cyclohexyl, propyl, butyl, 3-imidazolepropyl, 2-imidazolethyl, 1-(benzyloxycarbonyl)-4-hydroxypiperidin-4-yl, 1-isopropyl-4-hydroxypiperidin-4-ylm, 1-hydroxy-1-phenylmethyl, 1-[2-(4-fluorophenyl)-ethyl]-4-hydroxypiperidin-4-yl, 4-hydroxypiperidin-4-yl or 1-phenyl-1-hydroxypropyl,
$R^3$ denotes H,
$R^4$ denotes H, 1-(tetrahydrofuran-2-ylmethyl)-1H-pyrazolyl, methyl-(2-pyrazol-1-ylethyl)amino, dimethyl-(3-pyrazol-1-ylpropyl)amino, dimethyl-(2-pyrazol-1-ylethyl)amino, 1-methyl-4-pyrazol-1-ylpiperidinyl, 4-pyrazol-1-ylpiperidinyl, 1-phenylpiperazinyl, 1-(2-pyrrolidin-1-ylethyl)-1H-pyrazolyl, 4-(2-pyrazol-1-ylethyl)morpholinyl, 1-pyrrolidin-3-ylmethyl-1H-pyrazolyl, 3-[N-(2-dimethylaminoethyl)aminocarbonyl]phenyl, 4-methylpiperazine-1-carbonyl, morpholine-4-carbonyl, N-(4-dimethylaminobutyl)aminocarbonyl, 2-dimethylaminoethoxy, piperidin-4-ylmethoxy, C-piperidin-4-ylmethylamino, $CH_3NH(CH_2)_4NH—$, $(CH_3)_2N(CH_2)_4NH—$, 2-(tetrahydrofuran-2-ylmethyl)oxazolyl, 2-(tetrahydrofuran-2-ylmethyl)-1H-imidazolyl, 1-(tetrahydrofuran-2-ylmethyl)-1H-imidazolyl, 1-benzyl-1H-1,2,3-triazolyl 5-phenyloxazolyl, 4-aminomethylphenyl, 1-(1-acetylpiperidin-4-yl)pyrazol-4-yl, 1-piperidin-4-ylpyrazol-4-yl), 1-(2-hydroxyethyl)pyrazol-4-yl), 1-(1-methylpiperidin-4-yl)-pyrazol-4-yl, 2-isopropylpyrazol-4-yl, 1-(2-oxo-2-methylaminoethyl)pyrazol-4-yl, 1-[2-dimethylaminoethyl]pyrazol-4-yl, pyrazolyl, 1-methylpyrazol-4-yl, 1-(3-fluorobenzyl) pyrazol-4-yl, 1-(3,4-difluorobenzyl)pyrazol-4-y, 1-[1-(piperidin-1-yl)acetyl]pyrazol-4-yl, 1-[1-(pyrrolidin-1-yl)acetyl]pyrazol-4-yl, 1-[3-(indol-5-ylamino)-3-oxopropan-2-yl]-pyrazol-4yl or 1-(3,4-dihydro-2H-quinolin-1-ylcarbonylmethyl)pyrazol-4-yl,
A denotes unbranched or branched alkyl having 1-6 C atoms, in which one or two $CH_2$ groups are each optionally replaced by oxygen and/or in addition 1-7 H atoms are each optionally replaced by F,
Ar denotes phenyl which is unsubstituted or mono-, di- or trisubstituted by $N(R^5)_2$, Hal and/or $CON(R^5)_2$
Het denotes dihydropyrrolyl, pyrrolidinyl, tetrahydroimidazolyl, dihydropyrazolyl, tetrahydropyrazolyl, morpholinyl, piperazinyl, imidazolyl, pyrazolyl, oxazolyl, isoxazolyl, pyridyl, pyrimidinyl or triazolyl, dihydropyridyl, tetrahydropyridyl, piperidinyl, hexahydropyridazinyl, hexahydropyrimidinyl, piperazinyl, 1,2,3,4-tetrahydroquinolyl, 1,2,3,4-tetrahydroisoquinolyl, 3,4-dihydrobenzo-1,4-oxazinyl, 2,3-dihydroisoindolyl, 2,3-dihydroindolyl, pyrazolyl, pyridyl, furyl or isooxazyl, each of which is unsubstituted or mono-, di- or trisubstituted by A, (CH$_2$)$_p$Het$^1$, (CH$_2$)$_p$N(R$^5$)$_2$, NO$_2$, CN, (CH$_2$)$_p$COOR$^5$, (CH$_2$)$_p$CON(R$^5$)$_2$, NR$^5$COA, (CH$_2$)$_p$COHet$^1$, F and/or =O, n denotes 0, 1, 2, 3 or 4 and Het$^1$ denotes tetrahydrofuranyl, piperidinyl, piperazinyl, pyrrolidinyl, or morpholinyl, each of which is unsubstituted or monosubstituted by A, COA or S(O)$_p$A, and pharmaceutically usable salts, tautomers and stereoisomers thereof, including mixtures thereof in all ratios.

12. A compound according to claim 1, wherein said compound is selected from:

4-{5-[1-(2-dimethylaminoethyl)-1H-pyrazol-4-yl]-1H-pyrrolo[2,3-b]pyridin-3-yl}-6-ethylpyrimidin-2-ylamine, 4-ethyl-6-{(5-[1-(tetrahydrofuran-2-ylmethyl)-1H-pyrazol-4-yl]-1H-pyrrolo-[2,3-b]-pyridin-3-yl}pyrimidin-2-ylamine, 4-ethyl-6-{5-[1-(2-methylaminoethyl)-1H-pyrazol-4-yl]-1H-pyrrolo[2,3-b]pyridin-3-yl}pyrimidin-2-yl, 4-{5-[1-(3-dimethylaminopropyl)-1H-pyrazol-4-yl]-1H-pyrrolo[2,3-b]pyridin-3-yl}-6-ethylpyrimidin-2-ylamine, 4-ethyl-6-{5-[1-(1-methylpiperidin-4-yl)-1H-pyrazol-4-yl]-1H-pyrrolo[2,3-b]-pyridin-3-yl}pyrimidin-2-ylamine, 4-ethyl-6-[5-(1-piperidin-4-yl-1H-pyrazol-4-yl)-1H-pyrrolo[2,3-b]pyridin-3-yl]-pyrimidin-2-ylamine, 4-ethyl-6-{5-[1-(2-pyrrolidin-1-ylethyl)-1H-pyrazol-4-yl]-1H-pyrrolo-[2,3-b]-pyridin-3-yl}pyrimidin-2-ylamine, 4-ethyl-6-{5-[1-(2-morpholin-4-ylethyl)-1H-pyrazol-4-yl]-1H-pyrrolo[2,3-b]pyridin-3-yl}pyrimidin-2-ylamine, 4-ethyl-6-[5-(1-pyrrolidin-3-yl 1H-pyrazol-4-yl)-1H-pyrrolo[2,3-b]pyridin-3-yl]-pyrimidin-2-ylamine, 4-ethyl-6-[5-(6-piperazin-1-ylpyridin-3-yl)-1H-pyrrolo[2,3-b]pyridin-3-yl]-pyrimidin-2-ylamine, 3-[3-(2-amino-6-ethylpyrimidin-4-yl)-1H-pyrrolo[2,3-b]pyridin-5-yl]-N-(2-dimethylaminoethyl)benzamide,

[3-(2-amino-6-ethylpyrimidin-4-yl)-1H-pyrrolo[2,3-b]pyridin-5-yl]-(4-methylpiperazin-1-yl)methanone,

[3-(2-amino-6-ethylpyrimidin-4-yl)-1H-pyrrolo[2,3-b]pyridin-5-yl]morpholin-4-ylmethanone, N-(4-dimethylaminobutyl)-3-(2-amino-6-ethylpyrimidin-4-yl)-1H-pyrrolo-[2,3-b]-pyridin-5-carboxamide, 4-[5-(2-dimethylaminoethoxy)-1H-pyrrolo[2,3-b]pyridin-3-yl]-6-ethylpyrimidin-2-ylamine, 4-ethyl-6-[5-(piperidin-4-ylmethoxy)-1H-pyrrolo[2,3-b]pyridin-3-yl]-pyrimidin-2-ylamine,

[3-(2-amino-6-ethylpyrimidin-4-yl)-1H-pyrrolo[2,3-b]pyridin-5-yl]piperidin-4-ylmethylamine, N-[3-(2-amino-6-ethylpyrimidin-4-yl)-1H-pyrrolo[2,3-b]pyridin-5-yl]-N'-methylbutane-1,4-diamine, N-[3-(2-amino-6-ethylpyrimidin-4-yl)-1H-pyrrolo[2,3-b]pyridin-5-yl]-N',N'-dimethylbutane-1,4-diamine, 4-(3-aminopropyl)-6-{5-[1-(2-pyrrolidin-1-ylethyl)-1H-pyrazol-4-yl]-1H-pyrrolo-[2,3-b]pyridin-3-yl}pyrimidin-2-ylamine, 4-(3-aminopropyl)-6-{5-[1-(2-morpholin-4-ylethyl)-1H-pyrazol-4-yl]-1H-pyrrolo-[2,3-b]pyridin-3-yl}pyrimidin-2-ylamine, 4-morpholin-4-ylmethyl-6-{5-[1-(2-pyrrolidin-1-ylethyl)-1H-pyrazol-4-yl]-1H-pyrrolo-[2,3-b]pyridin-3-yl}pyrimidin-2-ylamine, 4-piperazin-1-ylmethyl-6-{5-[1-(2-pyrrolidin-1-ylethyl)-1H-pyrazol-4-yl]-1H-pyrrolo-[-2,3-b]pyridin-3-yl}pyrimidin-2-ylamine, 4-ethyl-6-{5-[1-(tetrahydrofuran-2-ylmethyl)-1H-imidazol-4-yl]-1H-pyrrolo[2,3-b]-pyridin-3-yl}pyrimidin-2-ylamine, 4-[5-(1-benzyl-1H-1,2,3-triazol-4-yl)-1H-pyrrolo[2,3-b]pyridin-3-yl]-6-ethylpyrimidin-2-ylamine, 4-(3-dimethylaminopropyl)-6-{5-[1-(2-pyrrolidin-1-ylethyl)-1H-pyrazol-4-yl]-1H-pyrrolo[2,3-b]pyridin-3-yl}pyrimidin-2-ylamine, 4-ethyl-6-[5-(5-phenyloxazol-2-yl)-1H-pyrrolo[2,3-b]pyridin-3-yl]pyrimidin-2-ylamine, 2-{4-[3-(2-amino-6-ethylpyrimidin-4-yl)-1H-pyrrolo[2,3-b]pyridin-5-yl]-pyrazol-1-yl}-1-(4-methylpiperazin-1-yl)ethanone, 2-{4-[3-(2-amino-6-ethylpyrimidin-4-yl)-1H-pyrrolo[2,3-b]pyridin-5-yl]-pyrazol-1-yl}-N-(1-methylpiperidin-4-yl)acetamide, {4-[3-(2-amino-6-ethylpyrimidin-4-yl)-1H-pyrrolo[2,3-b]pyridin-5-yl]pyrazol-1-yl}-acetic acid, 2-{4-[3-(2-amino-6-ethylpyrimidin-4-yl)-1H-pyrrolo[2,3-b]pyridin-5-yl]-pyrazol-1-yl}-1-morpholin-4-ylethanone, 2-{4-[3-(2-amino-6-ethylpyrimidin-4-yl)-1H-pyrrolo[2,3-b]pyridin-5-yl]-pyrazol-1-yl}ethanol, 2-{4-[3-(2-amino-6-ethylpyrimidin-4-yl)-1H-pyrrolo[2,3-b]pyridin-5-yl]-pyrazol-1-yl}-N,N-dimethylacetamide, 1-{2-amino-6-[5-(1-isopropyl-1H-pyrazol-4-yl)-1H-pyrrolo[2,3-b]pyridin-3-yl]-pyrimidin-4-yl}butan-1-ol, 1-{2-amino-6-[5-(1-isopropyl-1H-pyrazol-4-yl)-1H-pyrrolo[2,3-b]pyridin-3-yl]-pyrimidin-4-yl}propan-2-ol, 4-[5-(5-chlorothiophen-2-yl)-1H-pyrrolo[2,3-b]pyridin-3-yl]-6-ethylpyrimidin-2-ylamine, 3-{2-amino-6-[5-(1-isopropyl-1H-pyrazol-4-yl)-1H-pyrrolo[2,3-b]pyridin-3-yl]-pyrimidin-4-yl}propan-1-ol, 4(2-amino-6-{5-[1-(2-dimethylaminoethyl)-1H-pyrazol-4-yl]-1H-pyrrolo-[2,3-b]-pyridin-3-yl}pyrimidin-4-yl)butan-1-ol, 4-{2-amino-6-[5-(1-isopropyl-1H-pyrazol-4-yl)-1H-pyrrolo[2,3-b]pyridin-3-yl]-pyrimidin-4-yl}butan-1-ol, 4-{5-[1-(2-dimethylaminoethyl)-1H-pyrazol-4-yl]-1H-pyrrolo[2,3-b]pyridin-3-yl}-6-[2-(4-methylpiperazin-1-yl)ethyl]pyrimidin-2-ylamine, 4-{5-[5-(3-aminophenyl)oxazol-2-yl]-1H-pyrrolo[2,3-b]pyridin-3-yl}-6-ethylpyrimidin-2-ylamine, 4-[5-(1-isopropyl-1H-pyrazol-4-yl)-1H-pyrrolo[2,3-b]pyridin-3-yl]-6-[2-(4-methylpiperazin-1-yl)ethyl]pyrimidin-2-ylamine, 4-ethyl-6-{5-[1-(1-methanesulfonylpiperidin-4-yl)-1H-pyrazol-4-yl]-1H-pyrrolo-[2,3-b]pyridin-3-yl}pyrimidin-2-ylamine, 4-[2-amino-6-(1H-pyrrolo[2,3-b]pyridin-3-yl)pyrimidin-4-yl]butan-1-ol, 1-(4-{4-[3-(2-amino-6-ethylpyrimidin-4-yl)-1H-pyrrolo[2,3-b]pyridin-5-yl]pyrazol-1-yl}piperidin-1-yl)ethanone, 3-[2-amino-6-(1H-pyrrolo[2,3-b]pyridin-3-yl)pyrimidin-4-yl]-N-(3,4-difluorobenzyl)-propionamide, 1-[2-amino-6-(1-pyrrolo[2,3-b]pyridin-3-yl)pyrimidin-4-yl]butan-1-ol, 4-(2-morpholin-4-ylethyl)-6-(1H-pyrrolo[2,3-b]pyridin-3-yl)pyrimidin-2-ylamine, 4-[2-(4-methylpiperazin-1-yl)ethyl]-6-(1H-pyrrolo[2,3-b]pyridin-3-yl)pyrimidin-2-ylamine, 2-{4-[3-(2-amino-6-ethylpyrimidin-4-yl)-1H-pyrrolo[2,3-b]pyridin-5-yl]pyrazol-1-yl}-N-methylacetamide, 2-{4-[3 (2-amino-6-ethylpyrimidin-4-yl)-1H-pyrrolo[2,3-b]pyridin-5-yl]-pyrazol-1-yl}-N-cyclopropylacetamide,
1-{2-amino-6-[5-(1-isopropyl-1H-pyrazol-4-yl)-1H-pyrrolo[2,3-b]pyridin-3-yl]-pyrimidin-4-yl}cyclohexanol,
1-{2-amino-6-[5-(1-isopropyl-1H-pyrazol-4-yl)-1H-pyrrolo[2,3-b]pyridin-3-yl]-pyrimidin-4-yl}cyclopentanol,
1-{2-amino-6-[5-(1-isopropyl-1H-pyrazol-4-yl)-1H-pyrrolo[2,3-b]pyridin-3-yl]-pyrimidin-4-yl}-1-phenylethanol,
4-methylaminomethyl-6-{5-[1-(2-pyrrolidin-1-ylethyl)-1H-pyrazol-4-yl]-1H-pyrrolo-[2,3-b]pyridin-3-yl}-pyrimidin-2-ylamine,
4-(3-methylaminopropyl)-6-{5-[1-(2-pyrrolidin-1-ylethyl)-1H-pyrazol-4-yl]-1H-pyrrolo[2,3-b]pyridin-3-yl}pyrimidin-2-ylamine,
2-{4-[3-(2-amino-6-butylpyrimidin-4-yl)-1H-pyrrolo[2,3-b]pyridin-5-yl]-pyrazol-1-yl}-1-piperidin-1-ylethanone,
1-{2-amino-6-[5-(1-isopropyl-1H-pyrazol-4-yl)-1H-pyrrolo[2,3-b]pyridin-3-yl]-pyrimidin-4-yl}-1-phenylpropan-1-ol,
{4-ethyl-6-[5-(1-isopropyl-1H-pyrazol-4-yl)-1H-pyrrolo[2,3-b]pyridin-3-yl]pyrimidin-2-yl}methylamine,
(4-{5-[1-(2-dimethylaminoethyl)-1H-pyrazol-4-yl]-1H-pyrrolo[2,3-b]pyridin-3-yl}-6-ethylpyrimidin-2-yl)methylamine,
{4-ethyl-6-[5-(1H-pyrazol-4-yl)-1H-pyrrolo[2,3-b]pyridin-3-yl]pyrimidin-2-yl}methylamine,
{4-ethyl-6-[5-(1-methyl-1H-pyrazol-4-yl)-1H-pyrrolo[2,3-b]pyridin-3-yl]-pyrimidin-2-yl}methylamine,
{4-ethyl-6-[5-(1 piperidin-4-yl-1H-pyrazol-4-yl)-1H-pyrrolo[2,3-b]pyridin-3-yl]-pyrimidin-2-yl}methylamine,
2-{4-[3-(6-ethyl-2-methylaminopyrimidin-4-yl)-1H-pyrrolo[2,3-b]pyridin-5-yl]-pyrazol-1-yl}-1-piperidin-1-ylethanone,
2-{4-[3-(6-ethyl-2-methylaminopyrimidin-4-yl)-1H-pyrrolo[2,3-b]pyridin-5-yl]-pyrazol-1-yl}-1-pyrrolidin-1-ylethanone,
2-{4-[3-(6-butyl-2-methylaminopyrimidin-4-yl)-1H-pyrrolo[2,3-b]pyridin-5-yl]-pyrazol-1-yl}ethanol,
2-{4-[3-(6-ethyl-2-methylaminopyrimidin-4-yl)-1H-pyrrolo[2,3-b]pyridin-5-yl]-pyrazol-1-yl}ethanol,
(4-ethyl-6-{5-[1-(1-methylpiperidin-4-yl)-1H-pyrazol-4-yl]-1H-pyrrolo[2,3-b]-pyridin-3-yl}pyrimidin-2-yl)methylamine,
{4-butyl-6-[5-(1-piperidin-4-yl-1H-pyrazol-4-yl)-1H-pyrrolo[2,3-b]pyridin-3-yl]-pyrimidin-2-yl}methylamine,
(4-butyl-6-{5-[1-(1-methylpiperidin-4-yl)-1H-pyrazol-4-yl]-1H-pyrrolo[2,3-b]-pyridin-3-yl}pyrimidin-2-yl)methylamine,
2-{4-[3-(6-ethyl-2-methylaminopyrimidin-4-yl)-1H-pyrrolo[2,3-b]pyridin-5-yl]-pyrazol-1-yl}-N-(1H-indol-5-yl)propionamide,
1-(3,4-dihydro-2H-quinolin-1-yl)-2-{4-[3-(6-ethyl-2-methylaminopyrimidin-4-yl)-1H-pyrrolo[2,3-b]pyridin-5-yl]pyrazol-1-yl}ethanone,
3-(6-benzyl-2-methoxypyrimidin-4-yl)-5-(1-isopropyl-1H-pyrazol-4-yl)-1H-pyrrolo-[2,3-b]pyridine,
3-(6-ethyl-2-methoxypyrimidin-4-yl)-5-(1-isopropyl-1H-pyrazol-4-yl)-1H-pyrrolo-[2,3-b]pyridine,
3-(6-ethyl-2-methanesulfonylpyrimidin-4-yl)-5-(1-isopropyl-1H-pyrazol-4-yl)-1H-pyrrolo[2,3-b]pyridine,
3-(6-ethyl-2-methylsulfanylpyrimidin-4-yl)-1H-pyrrolo[2,3-b]pyridine,
4-[5-(4-aminomethylphenyl)-1H-pyrrolo[2,3-b]pyridin-3-yl]-6-ethylpyrimidin-2-ylamine,
3-[2-amino-6-(1H-pyrrolo[2,3-b]pyridin-3-yl)pyrimidin-4-yl]-1-morpholin-4-ylpropan-1-one,
3-[2-amino-6-(1H-pyrrolo[2,3-b]pyridin-3-yl)pyrimidin-4-yl]-N-(2-dimethylaminoethyl)propionamide,
4-(3-aminopropyl)-6-[5-(1-isobutyl-1H-pyrazol-4-yl)-1H-pyrrolo[2,3-b]-pyridin-3-yl]-pyrimidin-2-ylamine,
4-butyl-6-{5-[1-(2-dimethylaminoethyl)-1H-pyrazol-4-yl]-1H-pyrrolo[2,3-b]-pyridin-3-yl}pyrimidin-2-ylamine,
1-(4-{4-[3-(2-amino-6-butylpyrimidin-4-yl)-1H-pyrrolo[2,3-b]pyridin-5-yl]-pyrazol-1-yl}piperidin-1-yl)ethanone,
4-butyl-6-[5-(1 piperidin-4-yl-1H-pyrazol-4-yl)-1H-pyrrolo[2,3-b]pyridin-3-yl]-pyrimidin-2-ylanine,
2-{4-[3-(2-amino-6-butylpyrimidin-4-yl)-1H-pyrrolo[2,3-b]pyridin-5-yl]-pyrazol-1-yl}ethanol,
4-butyl-6-{5-[1-(1-methylpiperidin-4-yl)-1H-pyrazol-4-yl]-1H-pyrrolo[2,3-b]-pyridin-3-yl}pyrimidin-2-ylamine,
(S)-1-{2-amino-6-[5-(1-isopropyl-1H-pyrazol-4-yl)-1H-pyrrolo[2,3-b]pyridin-3-yl]-pyrimidin-4-yl}butan-1-ol,
R)-1-{2-amino-6-[5-(1-isopropyl-1H-pyrazol-4-yl)-1H-pyrrolo[2,3-b]pyridin-3-yl]-pyrimidin-4-yl}butan-1-ol,
2-{4-[3-(2-amino-6-ethylpyrimidin-4-yl)-1H-pyrrolo[2,3-b]pyridin-5-yl]-pyrazol-1-yl}-N-methylacetamide,
N-(3-{2-amino-6-[5-(1-isopropyl-1H-pyrazol-4-yl)-1H-pyrrolo[2,3-b]pyridin-3-yl]-pyrimidin-4-yl}propyl)acetamide,
4-ethyl-6-{5-[1-(3-fluorobenzyl)-1H-pyrazol-4-yl]-1H-pyrrolo[2,3-b]pyridin-3-yl}-pyrimidin-2-ylamine ("A98"),
4-{5-[1-(3,4-difluorobenzyl)-1H-pyrazol-4-yl]-1H-pyrrolo[2,3-b]pyridin-3-yl}-6-ethylpyrimidin-2-ylamine ("A99"),
3-{2-amino-6-[5-(1-isopropyl-1H-pyrazol-4-yl)-1H-pyrrolo[2,3-b]pyridin-3-yl]-pyrimidin-4-y}-N,N-dimethylpropionamide,
1-{2-amino-6-[5-(1-isopropyl-1H-pyrazol-4-yl)-1H-pyrrolo[2,3-b]pyridin-3-yl]-pyrimidin-4-yl}-2-methylpropan-1-ol,
1-{2-amino-6-[5-(1-isopropyl-1H-pyrazol-4-yl)-1H-pyrrolo[2,3-b]pyridin-3-yl]-pyrimidin-4-yl}propan-1-ol,
1-{2-amino-6-[5-(1-isopropyl-1H-pyrazol-4-yl)-1H-pyrrolo[2,3-b]pyridin-3-yl]-pyrimidin-4-yl}-3-methylbutan-1-ol,
4-cyclohexyl-6-(1H-pyrrolo[2,3-b]pyridin-3-yl)pyrimidin-2-ylamine,
2-{4-[3-(2-amino-6-butylpyrimidin-4-yl)-1H-pyrrolo[2,3-b]pyridin-5-yl]-pyrazol-1-yl}-1-pyrrolidin-1-ylethanone,
4-(3-imidazol-1-ylpropyl)-6-[5-(1-isopropyl-1H-pyrazol-4-yl)-1H-pyrrolo-[2,3-b]-pyridin-3-yl]pyrimidin-2-ylamine,
4-(2-imidazol-1-ylethyl)-6-[5-(1-isopropyl-1H-pyrazol-4-yl)-1H-pyrrolo[2,3-b]-pyridin-3-yl]pyrimidin-ylamine-2-ylamine,
4-cyclohexyl-6-[5-(1-isopropyl-1H-pyrazol-4-yl)-1H-pyrrolo[2,3-b]pyridin-3-yl]-pyrimidin-2-ylamine,
4-[2-amino-6-(1H-pyrrolo[2,3-b]pyridin-3-yl)pyrimidin-4-yl]-4-hydroxypiperidine-1-carboxylic acid benzyl ester,
4-{2-amino-6-[5-(1-isopropyl-1H-pyrazol-4-yl)-1H-pyrrolo[2,3-b]pyridin-3-yl]-pyrimidin-4-yl}-1-isopropylpiperidin-4-ol, {2-amino-6-[5-(1-isopropyl-1H-pyrazol-4-yl)-1H-pyrrolo[2,3-b]pyridin-3-yl]-pyrimidin-4-yl}phenylmethanol, 4-{2-amino-6-[5-(1-isopropyl-1H-pyrazol-4-yl)-1H-pyrrolo[2,3-b]pyridin-3-yl]-pyrimidin-4-yl}-1-[2-(4-fluorophenyl)ethyl]piperidin-4-ol, 2-{4-[3-(2-amino-6-ethylpyrimidin-4-yl)-1H-pyrrolo[2,3-b]pyridin-5-yl]-pyrazol-1-yl}-N-(1H-indol-5-yl)propionamide, 4-{2-amino-6-[5-(1-isopropyl-1H-pyrazol-4-yl)-1H-pyrrolo[2,3-b]pyridin-3-yl]-pyrimidin-4-yl}-4-hydroxypiperidine-1-carboxylic acid benzyl ester, (R)-1-{2-amino-6-[5-(1-isopropyl-1H-pyrazol-4-yl)-1H-pyrrolo[2,3-b]pyridin-3-yl]-pyrimidin-4-yl}-1-phenylethanol, (S)-1-{2-amino-6-[5-(1-isopropyl-1H-pyrazol-4-yl)-1H-pyrrolo[2,3-b]pyridin-3-yl]-pyrimidin-4-yl}-1-phenylethanol, 4-{2-amino-6-[5-(1-isopropyl-1H-pyrazol-4-yl)-1H-pyrrolo[2,3-b]pyridin-3-yl]-pyrimidin-4-yl}piperidin-4-ol, or 2-{4-[3-(2-amino-6-ethylpyrimidin-4-yl)-1H-pyrrolo[2,3-b]pyridin-5-yl]-pyrazol-1-yl}-1-(3,4-dihydro-2H-quinolin-1-yl)ethanone, and pharmaceutically usable salts, tautomers and stereoisomers thereof, including mixtures thereof in all ratios.

13. A process for the preparation of a compound according to claim 1 and pharmaceutically usable salts, tautomers and stereoisomers thereof, said process comprising:

a) reacting a compound of formula II

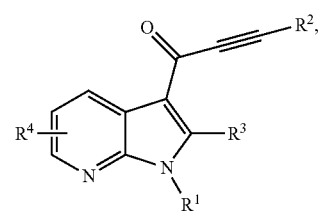

in which $R^1$ denotes an indole-protecting group,
$R^2$, $R^3$ and $R^4$ have the meanings indicated in claim 1,
with guanidine,
and simultaneously or subsequently cleaving off the indole-protecting group, or
b) converting a radical $R^2$ in a compound of the formula I into another $R^2$ by
  i) cleaving off an amino-protecting group,
  ii) cleaving an imide to give an amine, or
  iii) carrying out an alkylation, and/or
converting a base or acid of formula I into one of its salts.

14. A pharmaceutical composition comprising at least one compound of the formula I according to claim 1 and/or pharmaceutically usable salts, tautomers and stereoisomers thereof, including mixtures thereof in all ratios, and at least one optionally excipient and/or adjuvant.

15. A compound according to claim 1, wherein X is NH.
16. A compound according to claim 1, wherein X is O.
17. A compound according to claim 1, wherein X is S.
18. A compound according to claim 1, wherein X is $SO_2$.

* * * * *